US008541595B2

(12) United States Patent
Manley et al.

(10) Patent No.: US 8,541,595 B2
(45) Date of Patent: Sep. 24, 2013

(54) IMIDAZOISOINDOLE NEUROPEPTIDE S RECEPTOR ANTAGONISTS

(75) Inventors: Peter J. Manley, Harleysville, PA (US); Kausik K Nanda, Norristown, PA (US); B. Wesley Trotter, Newton Highlands, MA (US)

(73) Assignee: Merch Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/127,985

(22) PCT Filed: Nov. 3, 2009

(86) PCT No.: PCT/US2009/063052
§ 371 (c)(1),
(2), (4) Date: May 6, 2011

(87) PCT Pub. No.: WO2010/056567
PCT Pub. Date: May 20, 2010

(65) Prior Publication Data
US 2011/0212941 A1  Sep. 1, 2011

Related U.S. Application Data

(60) Provisional application No. 61/199,181, filed on Nov. 13, 2008.

(51) Int. Cl.
*A61K 31/4188* (2006.01)
*C07D 487/04* (2006.01)

(52) U.S. Cl.
USPC ........ 548/302.4; 540/603; 544/129; 544/139; 544/362; 544/367; 544/370; 546/17; 546/19; 546/115; 546/121; 546/139; 546/164; 546/187; 546/193; 546/199; 546/273.1; 548/215; 548/300.7

(58) Field of Classification Search
USPC ....................................... 548/302.4
See application file for complete search history.

(56) References Cited

U.S. PATENT DOCUMENTS 3,773,783 A * 11/1973 Houlihan ............... 548/302.4
2007/0213337 A1   9/2007 Wacker et al.

* cited by examiner

*Primary Examiner* — Laura L. Stockton
(74) *Attorney, Agent, or Firm* — J. Eric Thies; Gerard M. Devlin

(57) ABSTRACT

The present invention is directed to imidazoisoindole compounds which are antagonists of neuropeptide S receptors, and which are useful in the treatment or prevention of neurological and psychiatric disorders and diseases in which the neuropeptide S receptor is involved. The invention is also directed to pharmaceutical compositions comprising these compounds and the use of these compounds and compositions in the prevention or treatment of such diseases in which the neuropeptide S receptor is involved.

4 Claims, No Drawings

IMIDAZOISOINDOLE NEUROPEPTIDE S RECEPTOR ANTAGONISTS

CROSS REFERENCE TO RELATED APPLICATIONS

This application is a U.S. National Phase application under 35 U.S.C. §371 of PCT Application No. PCT/US2009/063052, filed Nov. 3, 2009, which claims priority under 35 U.S.C. §119(e) from U.S. Ser. No. 61/199,181, filed Nov. 13, 2008.

BACKGROUND OF THE INVENTION

Neuropeptide S(NPS) is an endogenous brain protein, which is believed to affect arousal, wakefulness, propensity for movement, asthma and some allergic responses, stress associated with several anxiety disorders and other physiological functions. Neuropeptide S is the endogenous ligand for the Neuropeptide S receptor (NPSR), which has also been referred to as TGR23 and vasopressin receptor-related receptor 1 (VRR1). The Neuropeptide S receptor is expressed in certain regions of the brain known to be involved in anxiety (e.g., the amygdala, thalamus and hypothalamic regions) and administration of NPS to rodents can cause increased locomotion and anxiolytic effects.

Neuropeptide S receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, dysregulated appetite control; obesity; addictive feeding behaviors; binge/purge feeding behaviors; cardiovascular diseases; diabetes; appetite, taste, eating or drinking disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; vigilance; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, and angina; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general neuropeptide S system dysfunction.

SUMMARY OF THE INVENTION

The present invention is directed to imidazoisoindole compounds which are antagonists of the neuropeptide S receptor, and which are useful in the treatment or prevention of neurological and psychiatric disorders and diseases in which neuropeptide S receptors are involved. The invention is also directed to pharmaceutical compositions comprising these compounds and the use of these compounds and compositions in the prevention or treatment of such diseases in which the neuropeptide S receptor is involved.

DETAILED DESCRIPTION OF THE INVENTION

The present invention is directed to compounds of the formula I:

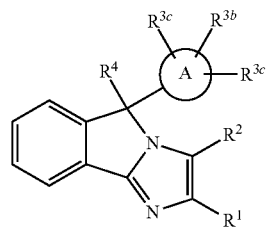

wherein:
A is phenyl or pyridyl;
$R^1$ is hydrogen or $C_{1-6}$alkyl;
$R^2$ is hydrogen or $C_{1-6}$alkyl;
$R^{3a}$, $R^{3b}$ and $R^{3c}$ are independently selected from the group consisting of:
  (1) hydrogen,
  (2) halogen,
  (3) hydroxyl,
  (4) —(C=O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from $R^{13}$,
  (5) —(C=O)$_m$—O$_n$—C$_{3-6}$cycloalkyl, where the cycloalkyl is unsubstituted or substituted with one or more substituents selected from $R^{13}$,
  (6) —(C=O)$_m$—C$_{2-4}$alkenyl, where the alkenyl is unsubstituted or substituted with one or more substituents selected from $R^{13}$,
  (7) —(C=O)$_m$—C$_{2-4}$alkynyl, where the alkynyl is unsubstituted or substituted with one or more substituents selected from $R^{13}$,
  (8) —(C=O)$_m$—O$_n$-phenyl or —(C=O)$_m$—O$_n$-napthyl, where the phenyl or naphthyl is unsubstituted or substituted with one or more substituents selected from $R^{13}$,
  (9) —(C=O)$_m$—O$_n$-heterocycle, where the heterocycle is unsubstituted or substituted with one or more substituents selected from $R^{13}$,

(10) —(C═O)$_m$—NR$^{10}$R$^{11}$, wherein R$^{10}$ and R$^{11}$ are independently selected from the group consisting of:
  (a) hydrogen,
  (b) C$_{1-6}$alkyl, which is unsubstituted or substituted with R$^{13}$,
  (c) C$_{3-6}$alkenyl, which is unsubstituted or substituted with R$^{13}$,
  (d) C$_{3-6}$alkynyl, which is unsubstituted or substituted with R$^{13}$,
  (e) C$_{3-6}$cycloalkyl which is unsubstituted or substituted with R$^{13}$,
  (f) phenyl, which is unsubstituted or substituted with R$^{13}$, and
  (g) heterocycle, which is unsubstituted or substituted with R$^{13}$,
(11) —S(O)$_2$—NR$^{10}$R$^{11}$,
(12) —S(O)$_q$—R$^{12}$, where q is 0, 1 or 2 and where R$^{12}$ is selected from the definitions of R$^{10}$ and R$^{11}$,
(13) —CO$_2$H,
(14) —CN, and
(15) —NO$_2$;
R$^4$ is —C$_{1-6}$alkyl, which is unsubstituted or substituted with one or more substituents selected from R$^5$,
wherein R$^5$ is selected from the group consisting of:
(1) halogen,
(2) hydroxyl,
(3) —(C═O)$_m$—O$_n$—C$_{1-6}$alkyl, where the alkyl is unsubstituted or substituted with one or more substituents selected from R$^{13}$,
(4) —(C═O)$_m$—O$_n$—C$_{3-6}$cycloalkyl, where the cycloalkyl is unsubstituted or substituted with one or more substituents selected from R$^{13}$,
(5) —(C═O)$_m$—C$_{2-4}$alkenyl, where the alkenyl is unsubstituted or substituted with one or more substituents selected from R$^{13}$,
(6) —(C═O)$_m$—C$_{2-4}$alkynyl, where the alkynyl is unsubstituted or substituted with one or more substituents selected from R$^{13}$,
(7) —(C═O)$_m$—O$_n$-phenyl or —(C═O)$_m$—O$_n$-napthyl, where the phenyl or naphthyl is unsubstituted or substituted with one or more substituents selected from R$^{13}$,
(8) —(C═O)$_m$—O$_n$-heterocycle, where the heterocycle is unsubstituted or substituted with one or more substituents selected from R$^{13}$,
(9) —(C═O)$_m$—NR$^{10}$R$^{11}$,
(10) —S(O)$_2$—NR$^{10}$R$^{11}$,
(11) —S(O)$_q$—R$^{12}$, and
(12) —CO$_2$H;
R$^{13}$ is selected from the group consisting of:
(1) halogen,
(2) hydroxyl,
(3) —(C═O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from R$^{14}$,
(4) —O$_n$—(C$_{1-3}$)perfluoroalkyl,
(5) —(C═O)$_m$—O$_n$—C$_{3-6}$cycloalkyl, where the cycloalkyl is unsubstituted or substituted with one or more substituents selected from R$^{14}$,
(6) —(C═O)$_m$—C$_{2-4}$alkenyl, where the alkenyl is unsubstituted or substituted with one or more substituents selected from R$^{14}$,
(7) —(C═O)$_m$—C$_{2-4}$alkynyl, where the alkynyl is unsubstituted or substituted with one or more substituents selected from R$^{14}$,
(8) —(C═O)$_m$—O$_n$-phenyl or —(C═O)$_m$—O$_n$-napthyl, where the phenyl or naphthyl is unsubstituted or substituted with one or more substituents selected from R$^{14}$,
(9) —(C═O)$_m$—O$_n$-heterocycle, where the heterocycle is unsubstituted or substituted with one or more substituents selected from R$^{14}$,
(10) —(C═O)$_m$—NR$^{15}$R$^{16}$, where R$^{15}$ and R$^{16}$ are independently selected from hydrogen and —C$_{1-6}$alkyl, which is unsubstituted or substituted with phenyl,
(11) —S(O)$_2$—NR$^{15}$R$^{16}$,
(12) —S(O)$_q$R$^{17}$, where R$^{17}$ is —C$_{1-6}$alkyl, which is unsubstituted or substituted with phenyl;
(13) —CO$_2$H,
(14) —CN, and
(15) —NO$_2$;
R$^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C═O)—C$_{1-6}$alkyl,
(7) —NH—C$_{1-6}$alkyl,
(8) phenyl,
(9) heterocycle,
(10) —CO$_2$H, and
(11) —CN;
or a pharmaceutically acceptable salt thereof.

An embodiment of the present invention includes compounds of the formula Ia:

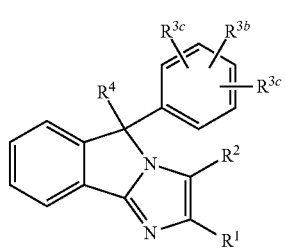

Ia wherein R$^1$, R$^2$, R$^{3a}$, R$^{3b}$, R$^{3c}$ and R$^4$ are defined herein; or a pharmaceutically acceptable salt thereof.

An embodiment of the present invention includes compounds of the formula Ib:

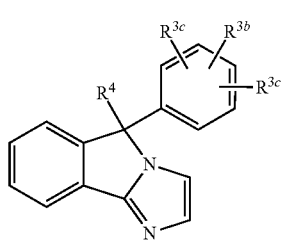

Ib wherein R$^{3a}$, R$^{3b}$, R$^{3c}$ and R$^4$ are defined herein; or a pharmaceutically acceptable salt thereof.

An embodiment of the present invention includes compounds of the formula Ic:

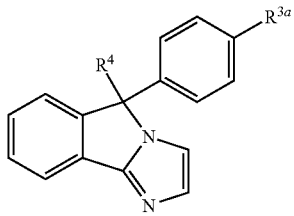

wherein $R^{3a}$ and $R^4$ are defined herein; or a pharmaceutically acceptable salt thereof.

An embodiment of the present invention includes compounds wherein $R^1$ is hydrogen or methyl. An embodiment of the present invention includes compounds wherein $R^1$ is hydrogen. An embodiment of the present invention includes compounds wherein $R^2$ is hydrogen or methyl. An embodiment of the present invention includes compounds wherein $R^2$ is hydrogen.

An embodiment of the present invention includes compounds wherein $R^{3a}$, $R^{3b}$ and $R^{3c}$ are independently selected from the group consisting of:
(1) hydrogen,
(2) halogen,
(3) —CN, and
(4) $C_{1-6}$alkyl.

An embodiment of the present invention includes compounds wherein $R^{3b}$ is hydrogen, $R^{3c}$ is hydrogen, and $R^{3a}$ is selected from the group consisting of:
(1) hydrogen,
(2) halogen,
(3) —CN, and
(4) $C_{1-6}$alkyl.

An embodiment of the present invention includes compounds wherein $R^{3b}$ is hydrogen, $R^{3c}$ is hydrogen, and $R^{3a}$ is in the 3-position of the phenyl ring and is selected from the group consisting of:
(1) hydrogen,
(2) halogen,
(3) —CN.

An embodiment of the present invention includes compounds wherein $R^{3b}$ is hydrogen, $R^{3c}$ is hydrogen, and $R^{3a}$ is in the 3-position of the phenyl ring and is halogen.

An embodiment of the present invention includes compounds wherein $R^{3b}$ is hydrogen, $R^{3c}$ is hydrogen, and $R^{3a}$ is in the 3-position of the phenyl ring and is selected from the group consisting of:
(1) fluoro,
(2) chloro, and
(3) bromo.

An embodiment of the present invention includes compounds wherein $R^4$ is selected from the group consisting of:
(1) —CH$_2$-phenyl, where the phenyl is unsubstituted or substituted with one or more substituents selected from $R^{13}$,
(2) —CH$_2$-pyridyl, where the pyridyl is unsubstituted or substituted with one or more substituents selected from $R^{13}$,
(3) —CH$_2$—C$_{3-6}$cycloalkyl, where the cycloalkyl is unsubstituted or substituted with one or more substituents selected from $R^{13}$,
(4) —CH$_2$-tetrahydrofuranyl or CH$_2$-tetrahydropyranyl, where the tetrahydrofuranyl or tetrahydropyranyl is unsubstituted or substituted with one or more substituents selected from $R^{13}$,
(5) —CH$_2$CH$_2$—(C=O)-heterocycle, where the heterocycle is unsubstituted or substituted with one or more substituents selected from $R^{13}$,
(6) —CH$_2$—(C=O)-heterocycle, where the heterocycle is unsubstituted or substituted with one or more substituents selected from $R^{13}$, and
(7) —CH$_2$CH$_2$—(C=O)—NR$^{15}$R$^{16}$, where $R^{15}$ and $R^{16}$ are independently selected from hydrogen and —C$_{1-6}$alkyl, which is unsubstituted or substituted with phenyl.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual enantiomers or diastereomers thereof.

The subject compounds are useful in a method of antagonizing neuropeptide S receptor activity in a patient such as a mammal in need of such inhibition comprising the administration of an effective amount of the compound. The present invention is directed to the use of the compounds disclosed herein as antagonists of neuropeptide S receptor activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing neuropeptide S receptor activity or treating the disorders and diseases noted herein in humans and animals.

The subject treated in the present methods is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as Neuropeptide S receptor agonists and/or antagonists may be readily determined without undue experimentation by methodology well known in the art, including the "FLIPR $Ca^{2+}$ Flux Assay" (Hodder et al., J Biomol Screen., 9(5):417-26, 2004). In a typical experiment the Neuropeptide S receptor agonistic and antagonistic activity of the compounds of the present invention were determined in accordance with the following experimental method. For intracellular calcium measurements, Chinese hamster ovary (CHO) cells expressing the human Neuropeptide S receptor A gene (NPSrA) (T. Laitinen et al., Science 304:300, 2004), are grown in Dulbecco's Modification of Eagle's Medium (DMEM) containing 4 mM L-glutamine, 0.5 g/ml G418, 100 uM non-essential amino acids (glycine, L-alanine, L-asparagine, L-aspartic acid, L-glutamic acid, L-proline, and L-serine), 1 mM sodium pyruvate, 25 mM Hepes, pH 7.4, 100

U/ml penicillin, 100 ug/ml streptomycin and 10% fetal bovine serum (FBS). The cells are seeded at 15,000 cells/well into black 384-well clear bottom sterile plates coated with poly-D-lysine (BectonDickinson Labware). DMEM is from MediaTech Inc., FBS is from Hyclone Inc., and the remaining reagents were from GIBCO-Invitrogen Corp. The seeded plates are incubated for 24 hours at 37° C. and 5% $CO_2$. Human Neuropeptide S (Y-L. Xu et al., Neuron 43:487, 2004) as the agonist is prepared as a 400 nM stock solution in assay buffer pH 7.4 (HBSS containing 20 mM Hepes, 250 uM probenecid, 0.1% (w/v) bovine serum albumin fraction V (BSA) and 800 uM TR40 (Zhang et al., J Biomol Screening 8:571-77, 2003)). Test compounds for the first addition are prepared as 10 mM stock solutions in DMSO, then are serially tirated in DMSO, diluted into assay buffer and transferred into 384-well plates, giving 5× compound concentrations from 50 uM in assay buffer plus 0.1% BSA, 800 uM TR40, and 2.5% DMSO. Human Neuropeptide S is used as a positive control at a 5× concentration of 100 nM. After 24 hours of growth, cells are washed 3 times with 100 ul wash buffer (assay buffer without TR40 or BSA), leaving 30 ul each time. Then 10 ul of 4× dye loading buffer is added, resulting in a 40 ul volume of assay buffer plus 2.5 uM Fluo-4 AM ester, 0.02% pluronic acid, 0.1% BSA and 800 uM TR40. Cells are incubated in dye loading buffer for 60 min (37° C., 5% $CO_2$). After 60 minutes, plates are transferred to the Fluorescent Imaging Plate Reader (FLIPR, Molecular Devices), where 10 ul of the 5× compound plate are added to the 40 ul existing volume. Fluorescence is measured for each well at 1 second intervals for 1 minute then 6 second intervals for 3 minutes; and each fluorescence peak maximum is compared to the fluorescence peak maximum induced by 20 nM ($EC_{100}$) human Neuropeptide S. For each tested compound, an $EC_{50}$ value (the effective concentration of compound needed to produce 50% of the NPS control response) is determined. After the initial 4 minute FLIPR read, 16.67 ul of 4×NPS agonist is immediately added to the 50 ul existing well volume, giving a final concentration of NPS at its $EC_{80}$ of 3 nM. Fluorescence is measured for each well at 1 second intervals for 1 minute then 6 second intervals for 3 minutes; and each fluorescence peak maximum is compared to the fluorescence peak maximum induced by 3 nM NPS with 0.5% DMSO in assay buffer in place of test compound. For each tested antagonist, $IC_{50}$ value (the concentration of compound needed to inhibit 50% of the agonist response) is determined. The intrinsic Neuropeptide S receptor agonist and antagonist activity of a compound which may be used in the present invention may be determined by these assays.

One skilled in the art can appreciate that the potentiator activity of test compounds can also be determined by similar experimental methods by adding Neuropeptide S at its $EC_{20}$ concentration of 0.05 nM in the second addition, and determining if compounds sensitized the cells to NPS by measuring any increase in the FLIPR response.

In particular, the compounds of the following examples had activity in agonizing and/or antagonizing the human Neuropeptide S receptor in the aforementioned assays, generally with an $IC_{50}$ of less than about 10 uM. Many of compounds within the present invention had activity in agonizing and/or antagonizing the human Neuropeptide S receptor in the aforementioned assays with an $IC_{50}$ of less than about 100 nM. Additional data is provided herein. Such a result is indicative of the intrinsic activity of the compounds in use as agonists and/or antagonists of human Neuropeptide S receptor. The present invention also includes compounds within the generic scope of the invention which possess activity as agonists of the Neuropeptide S receptor.

The Neuropeptide S receptor has been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with neuropeptide S receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociateive disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, dependence, withdrawal or relapse from substances including alcohol, amphetamines, cannabis, cocaine, hallucinogens, inhalants, morphine, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in specific embodiments the present invention provides methods for: enhancing the quality of sleep; augmenting sleep maintenance; increasing REM sleep; increasing stage 2 sleep; decreasing fragmentation of sleep patterns; treating insomnia and all types of sleep disorders; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling dysthymic, mood, psychotic and anxiety disorders; treating or controlling depression, including major depression and major dperession disorder; treating or controlling bipolar disorder; or treating, controlling, ameliorating or reducing the risk of schizophrenia, in a mammalian patient in need thereof which comprises administering to the patient a therapeutically effective amount of a compound of the present invention.

The subject compounds are further useful in a method for the prevention, treatment, control, amelioration, or reducation of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of neuropeptide S receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day. The compounds may be administered before bedtime. For example, the compounds may be administered about 1 Hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in conbination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other neuropeptide S antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, include, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-$NH_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activator receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fabric acid derivatives, such as Atromid®, Lopid® and Tricor®, and the like, and PPARα agonists as described in WO 97/36579; (g) PPARδ agonists, such as those disclosed in WO97/28149; (h) PPAR α/δ agonists, such as muraglitazar, and the compounds disclosed in U.S. Pat. No. 6,414,002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163, 255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-0B, Hoffman La Roche) and recombinant methionyl human leptin (Amgen); (31) leptin derivatives; (32) BRS3 (bombesin receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) a minorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide, (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; GABAA inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other neuropeptide S receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptble salts thereof.

In another embodiment, the subject compound may be employed in combination with an anoretic agent such as a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; i-Pr: isopropyl; t-Bu: tert-butyl; Ar: aryl; Ph: phenyl; Bn: benzyl; Ac: acetyl; THF: tetrahydrofuran; DEAD: diethylazodicarboxylate; DIPEA: N,N-diisopropylethylamine; NMM: N-methylmorpholine; DMAP: 4-dimthylaminopyridine; DMSO: dimethylsulfoxide; EDC: N-(3-Dimethylaminopropyl)-N'-ethylcarbodiimide; HOBT: hydroxybenzotriazole hydrate; Boc: tert-butyloxy carbonyl; TEA: triethylamine; DCM: dichloromethane; DCE: dichloroethane; BSA: bovine serum albumin; TFA: trifluoroacetic acid; DMF: N,N-dimethylformamide; MTBE: methyl tert-butyl ether; $SOCl_2$: thionyl chloride; CDI: carbonyl diimidazole; PyClu: 1-(chloro-1-pyrrolidinylmethylene)-pyrrolidinium hexafluorophosphate; dba: dibenzylideneacetone; S-Phos: 2-dicyclohexylphosphino-2',6'-dimethoxybiphenyl; dppf: 1,1'-bis-(diphenylphosphino)ferrocene; rt: room temperature; HPLC: high performance liquid chromatography. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

SCHEME I

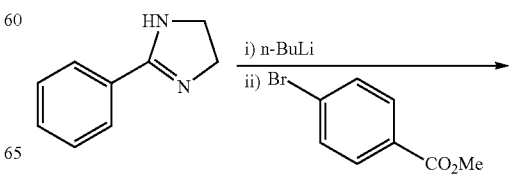

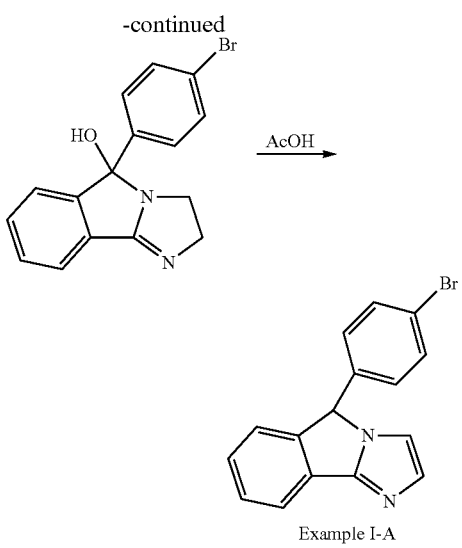

EXAMPLE I-A

Step 1: 5-(4-bromophenyl)-2,5-dihydro-3H-imidazo[2,1-a]isoindol-5-ol

To a solution of 2-phenyll midazoline (16.5 g) in THF (100 mL) was added a solution of n-BuLi (93 mL, 2.5 M in hexane) slowly so that the internal reaction temperature did not rise above 30° C. (an ice bath was used when necessary). A tan solid precipitated. The reaction mixture was then heated at 50° C. for 3 h. After cooling to room temperature a solution of methyl 4-bromobenzoate (26.7 g) in THF (60 mL) was added and was stirred overnight. The heterogeneous reaction mixture was then cooled to 0° C. and aqueous saturated $NH_4Cl$ (58 mL) was added to it. Precipitated solid was then collected by filtration, washed with water (1×). This solid was then taken in EtOH (500 mL), heated at 90° C. for 1 h and then cooled to 0° C. The solid was collected by filtration and dried under vacuum to give title compound as a white solid. Mass. found $(M+H)^+$, 329.0.

Step 2, Example I-A: 5-(4-bromophenyl)-5H-imidazo[2,1-a]isoindole

A solution of 5-(4-bromophenyl)-2,5-dihydro-3H-imidazo[2,1-a]isoindol-5-ol (20.5 g) in AcOH (210 mL) was heated at 125° C. under nitrogen for 6.5 h. The reaction mixture was the cooled to room temperature and concentrated. The resulting residue was partitioned between EtOAc and saturated aqueous $NaHCO_3$ solution. Aqueous layer was extracted with EtOAc (2×). Combined organic layers were washed with brine, dried over $Na_2SO_4$ and concentrated. Flash chromatography using a linear gradient of 0-4% MeOH in EtOAc-hexanes (1:1, v/v) afforded title compound as a light yellow solid. Mass. found $(M+H)^+$, 311.0.

SCHEME II

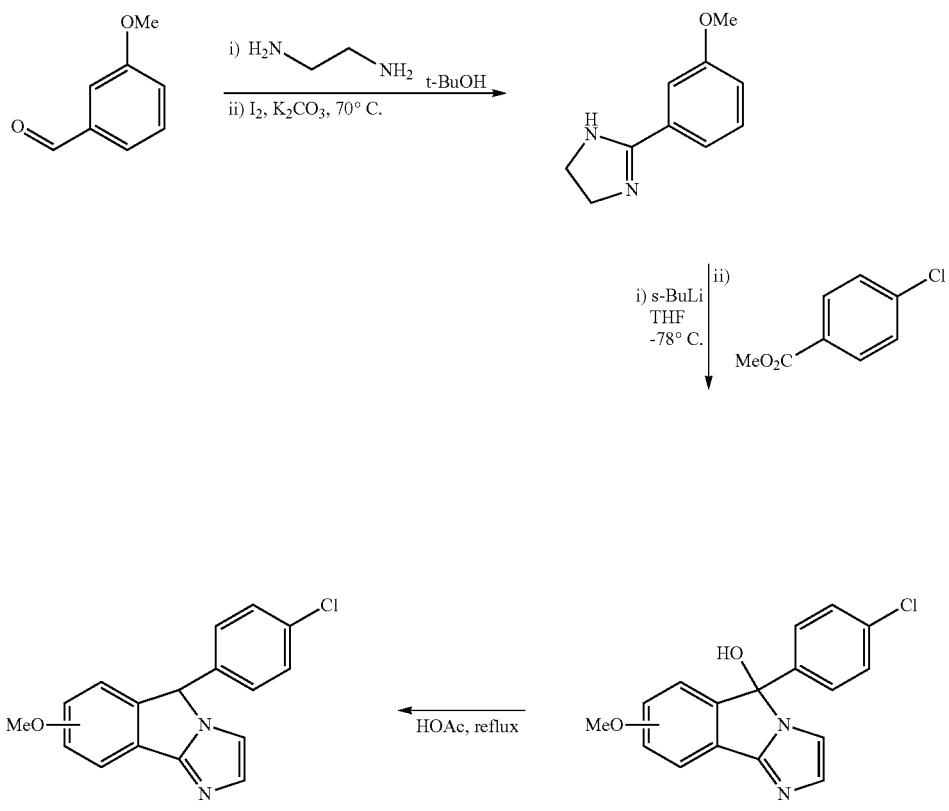

Examples II-A and II-B

EXAMPLES II-A AND II-B

Step 1:
2-(3-methoxyphenyl)-4,5-dihydro-1H-imidazole

To a solution of 3-methoxybenzaldehyde (0.895 ml) in t-BuOH (30 ml) was added ethylenediamine (0.546 ml) at room temperature. After 30 min $K_2CO_3$ (3.05 g) and $I_2$ (2.330 g) were added then the mixture was heated to 70° C. After 4 h the mixture was diluted with saturated aqueous $Na_2SO_3$ and extracted with $CHCl_3$ (3x). The combined organic layers were dried ($Na_2SO_4$), filtered, and concentrated. Flash column chromatography (gradient, 0-10% $MeOH/CHCl_3$ saturated with $NH_3$) gave 2-(3-methoxyphenyl)-4,5-dihydro-1H-imidazole as a pale yellow oil which solidified under vacuum (1.05 g): $^1$H-NMR (500 MHz, $CDCl_3$) δ 7.38 (m, 2 H), 7.32 (t, J=8.3 Hz, 1 H), 7.01 (m, 1 H), 6.90 (br, 1 H), 3.78 (s, 3 H), 3.59 (br, 2 H), 2.50 (t, J=1.71 Hz, 2 H).

Step 2: To a solution of 2-(3-methoxyphenyl)-4,5-dihydro-1H-imidazole (1.05 g, 5.96 mmol) in THF (20 ml) was added s-BuLi (10.6 ml, 14.84 mmol) slowly at −78° C. After 2 hr methyl 4-chlorobenzoate (1.525 g, 8.94 mmol) was added all at once as a solid. After 5 min the cooling bath was removed and the mixture was allowed to warm to RT. After 2 hr AcOH (5 ml, 87 mmol) was added and the mixture concentrated. The crude material was carried on immediately to the next step.

Step 3, Examples II-A and II-B: 5-(4-chlorophenyl)-6-methoxy-5H-imidazo[2,1-a]isoindole and 5-(4-chlorophenyl)-8-methoxy-5H-imidazo[2,1-a]isoindole The crude material from step 2 was taken up in AcOH (20 ml) then heated to reflux. After 16 hr the mixture was concentrated. The residue was taken up in saturated aqueous $NaHCO_3$ and extracted with $CH_2Cl_2$ (3x). The combined organic layers were dried ($Na_2SO_4$), filtered, and concentrated. Flash column chromatography (50% EtOAc/hexanes) gave 5-(4-chlorophenyl)-6-methoxy-5H-imidazo[2,1-a] isoindole as a pale yellow solid (892 mg): $^1$H-NMR (400 MHz, $CDCl_3$) δ 7.50 (d, J=7.5 Hz, 1 H), 7.42 (t, J=8.06 Hz, 2 H), 7.27 (m, 3 H), 7.04 (m, 2 H), 6.94 (d, J=1.28 Hz, 1 H), 6.81 (d, J=8.15 Hz, 1 H), 5.94 (s, 1 H), 3.71 (s, 3 H) and 5-(4-chlorophenyl)-8-methoxy-5H-imidazo[2,1-a]isoindole as an orange foam (207 mg): $^1$H-NMR (400 MHz, $CDCl_3$) δ 7.41 (d, J=2.38 Hz, 1 H), 7.34 (m, 2 H), 7.25 (m, 1 H), 7.09-7.03 (m, 3 H), 6.98 (s, 1 H), 6.82 (dd, J=2.47 and 5.95 Hz, 1 H), 5.86 (s, 1 H), 3.87 (s, 3 H).

SCHEME III

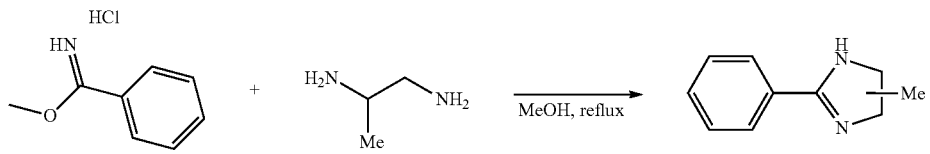

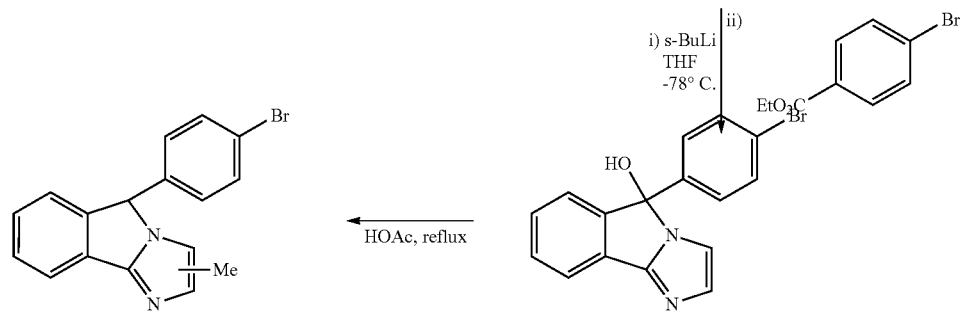

Examples III-A and III-B

EXAMPLES III-A AND III-B

Step 1:
4-methyl-2-phenyl-4,5-dihydro-1H-imidazole

To a solution of benzimidic acid methyl ester hydrochloride (1 g) in MeOH (25 ml) was added 1,2-diaminopropane (545 μL) then the mixture was heated to reflux. After 16 h the mixture was cooled to room temperature and concentrated. The residue was taken up in MeOH then passed through Dowex 1x2-400 ion exchange resin (prewashed with 1M NaOH, $H_2O$, MeOH) washing with MeOH. The filtrate was concentrated. Flash column chromatography (gradient, 0-10% $MeOH/CHCl_3$ saturated with $NH_3$) gave 4-methyl-2-phenyl-4,5-dihydro-1H-imidazole as a white solid (1.04 g) which was sufficiently pure for use in the next step. $^1$H-NMR (400 MHz, $CDCl_3$) δ 7.84 (m, 2 H), 7.55-7.38 (m, 3 H), 4.16 (m, 1 H), 3.95 (dd, J=9.98 and 1.83 Hz, 1 H), 3.40 (m, 1 H), 1.32 (d, J=6.41 Hz, 3 H).

Step 2: To a solution of 4-methyl-2-phenyl-4,5-dihydro-1H-imidazole (250 mg) in dry THF (5 ml) was added s-BuLi (2.45 mL, 3.43 mmol) slowly at −78° C. After 2 h ethyl 4-bromobenzoate (0.31 mL) was added. The cooling bath was removed and the mixture allowed to warm to room temperature. After 1 h the mixture was diluted with brine and extracted with dichloromethane (3x). The combined organic layers were dried ($Na_2SO_4$), filtered, and concentrated. The residue was triturated with $Et_2O$ to give a white solid (469 mg) which was sufficiently pure for use in the next step.

Step 3, Examples III-A and III-B: 5-(4-bromophenyl)-2-methyl-5H-imidazo[2,1-a]isoindole and 5-(4-bromophenyl)-3-methyl-5H-imidazo[2,1-a]isoindole The crude solid from step 2 (469 mg) was taken up in AcOH (5 ml) then heated to 125° C. After 4 h the mixture was cooled to room temperature and concentrated. The residue was taken up in saturated aqueous NaHCO$_3$ and extracted with CH$_2$Cl$_2$ (3×). The combined organic layers were dried (Na$_2$SO$_4$), filtered, and concentrated. Flash column chromatography (40% EtOAc/hexanes) gave 5-(4-bromophenyl)-2-methyl-5H-imidazo[2,1-a]isoindole as an off-white solid (286 mg): $^1$H-NMR (500 MHz, CDCl$_3$) δ 7.82 (d, J=7.57 Hz, 1 H), 7.48 (m, 2 H), 7.41 (t, J=7.57 Hz, 1 H), 7.20 (m, 2 H), 7.00 (m, 2 H), 6.72 (s, 1 H), 5.83 (s, 1 H), 2.34 (s, 3 H) and 5-(4-bromophenyl)-3-methyl-5H-imidazo[2,1-a]isoindole as an off-white solid (115 mg, 26%): $^1$H-NMR (500 MHz, CDCl$_3$) δ 7.82 (d, J=7.56 Hz, 1 H), 7.47 (m, 2 H), 7.41 (t, J=7.47 Hz, 1 H), 7.24 (m, 1 H), 7.16 (m, 1 H), 7.01 (m, 1 H), 6.94 (s, 1 H), 5.83 (s, 1 H), 1.98 (s, 3 H).

mide (3 mL) was added and continued to stir at −40° C. for 40 minutes. The reaction was then quenched with aqueous saturated NH$_4$Cl and partitioned between aqueous saturated NH$_4$Cl and EtOAc. Aqueous layer was extracted with EtOAc (2×). Combined organic layers were dried over Na$_2$SO$_4$ and concentrated. The resulting yellow solid was recrystallized from hot EtOAc to yield title compound as a white solid. HRMS. Found, 401.0647; calcd for (M+H)$^+$, 401.0648. $^1$HNMR (500 MHz, CDCl$_3$): δ 7.62 (d, J=7.1 Hz, 1H), 7.50 (d, J=8.6 Hz, 2H), 7.36 (dd, J=7.1, 0.9 Hz, 1H), 7.33-7.27 (m, 2H), 7.24 (s, 1H), 7.15 (d, J=8.3 Hz, 2H), 7.03 (t, J=7.8 Hz, 1H), 6.95 (t, J=7.8 Hz, 2H), 6.91 (s, 1H), 6.56 (d, J=7.6 Hz, 2H), 3.78 (s, 2H).

Step 2, Example IV-2: 4-(5-benzyl-5H-imidazo[2,1-a]isoindol-5-yl)benzonitrile

A r.b. flask containing 5-benzyl-5-(4-bromophenyl)-5H-imidazo[2,1-a]isoindole (115 mg), Zn(CN)$_2$ (67 mg), zinc powder (2 mg), [Pd$_2$(dba)$_3$] (13 mg) and dppf (16 mg) was

SCHEME IV

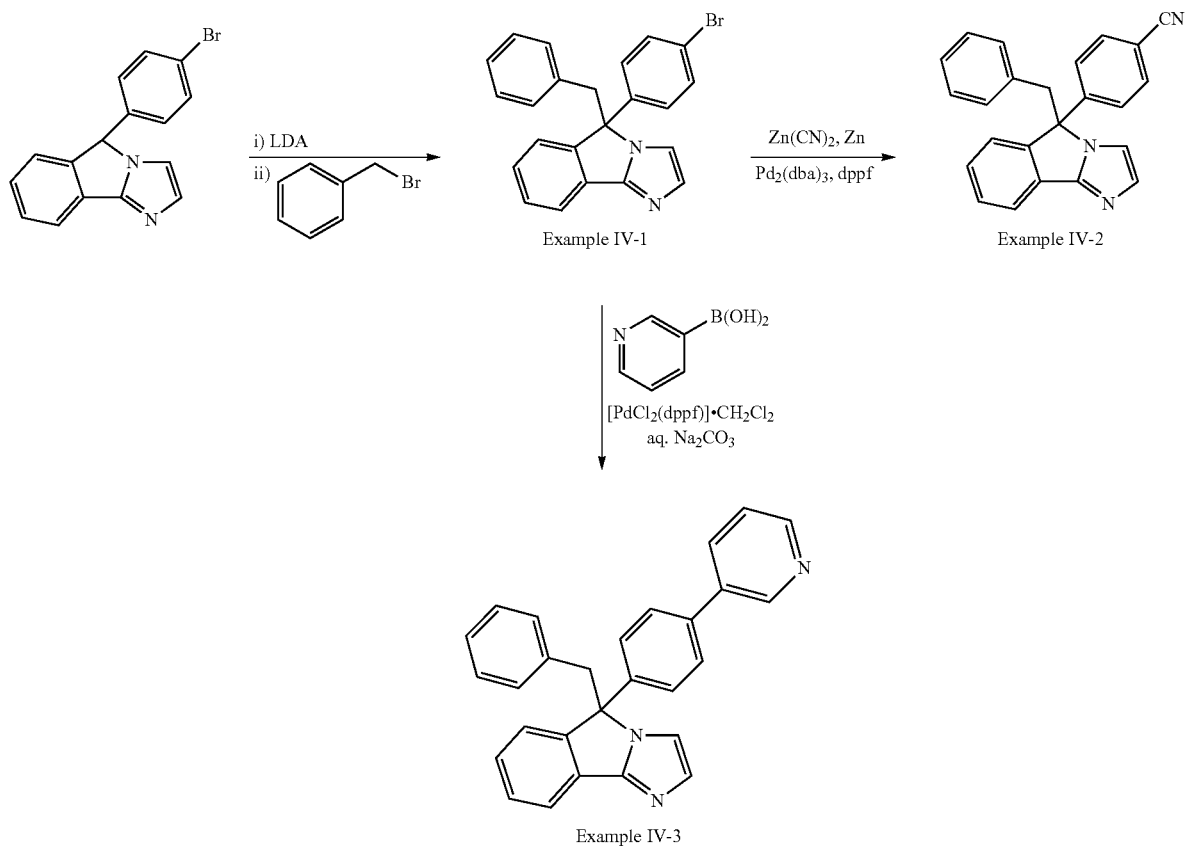

Example IV-1

Example IV-2

Example IV-3

EXAMPLES IV-1, IV-2 AND IV-3

Step 1, Example IV-1: 5-benzyl-5-(4-bromophenyl)-5H-imidazo[2,1-a]isoindole

To a solution of 5-(4-bromophenyl)-5H-imidazo[2,1-a]isoindole (5 g) in THF (100 mL) at −78° C. was added LAD solution (21.42 mL, 1.5 M in cyclohexane). After stirring for 15 minutes benzylbromide was added and the reaction mixture was stirred at −40° C. After 20 minutes more benzylbropurged with Ar. DMA (3 mL) was added to this mixture and heated at 120° C. for 4.5 h. After cooling to room temperature the reaction mixture was diluted with EtOAc. Organic layer was washed with 2(N) aqueous NH$_4$OH (1×) and brine (1×), dried over Na$_2$SO$_4$ and concentrated. Purification by reversed phase HPLC (21×100 mm Phenomenex Gemini, 15-85% MeCN/water containing 0.05% NH$_4$OH over 20 min at 20 mL/min) afforded the title compound as a white solid. HRMS. Found, 348.1497; calcd for (M+H)$^+$, 348.1495. $^1$H NMR (500 MHz, CDCl$_3$): δ 7.69-7.63 (m, 3H), 7.40-7.29 (m, 6H), 7.05 (t, J=7.6 Hz, 1H), 6.97 (t, J=7.6 Hz, 2H), 6.90 (d, J=1.5 Hz, 1H), 6.57 (d, J=7.3 Hz, 2H), 3.81 (s, 2H).

Step 3, Example IV-3: 5-benzyl-5-(4-pyridin-3-ylphenyl)-5H-imidazo[2,1-a]isoindole To a mixture of 5-benzyl-5-(4-bromophenyl)-5H-imidazo[2,1-a]isoindole (30 mg), 3-pyridylboronic acid (18 mg) and [PdCl$_2$(dppf)].CH$_2$Cl$_2$ (6 mg) was added THF (2 mL) followed by aqueous Na$_2$CO$_3$ (0.112 mL, 2 M). The reaction vessel was then sealed and heated at 150° C. under microwave irradiation for 20 minutes. The reaction mixture was then diluted with EtOAc and the organic layer was collected and concentrated. Purification by reversed phase HPLC (21×100 mm Phenomenex Gemini, 5-40% MeCN/water containing 0.1% TFA over 20 min at 20 mL/min) afforded the title compound as a white solid. HRMS. Found, 400.1805; calcd for (M+H)$^+$, 400.1808. $^1$H NMR (500 MHz, CDCl$_3$): δ 8.84 (d, J=1.9 Hz, 1H), 8.61 (dd, J=4.9, 1.5 Hz, 1 H), 7.86-7.84 (m, 1 H), 7.65-7.58 (m, 3H), 7.45-7.26 (m, 7H), 7.05-7.03 (m, 1H), 6.99-6.95 (m, 3H), 6.60 (d, J=7.3 Hz, 2H), 3.89-3.83 (m, 2H).

The following compounds were prepared using the experimental procedure described above for Scheme III.

| STRUCTURE | Chemical name | Mass found |
|---|---|---|
|  | 5-benzyl-5-(4-bromophenyl)-2-methyl-5H-imidazo[2,1-a]isoindole | 415.0796 |
|  | 5-(4-bromophenyl)-2-methyl-5-(tetrahydro-2H-pyran-4-ylmethyl)-5H-imidazo[2,1-a]isoindole | 423.1059 |
|  | 5-(4-bromophenyl)-3-methyl-5-(tetrahydro-2H-pyran-4-ylmethyl)-5H-imidazo[2,1-a]isoindole | 423.106 |
| 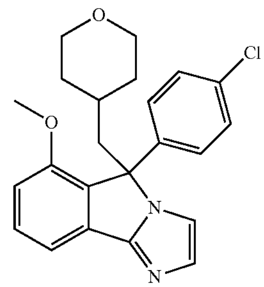 [SMILES: COc1cccc2c1C(CC1CCOCC1)(c1ccc(Cl)cc1)n1ccnc1-2] | 5-(4-chlorophenyl)-6-methoxy-5-(tetrahydro-2H-pyran-4-ylmethyl)-5H-imidazo[2,1-a]isoindole | 395.1511 |
|  | 5-benzyl-5-(4-bromophenyl)-5H-imidazo[2,1-a]isoindole | 401.0647 |
| 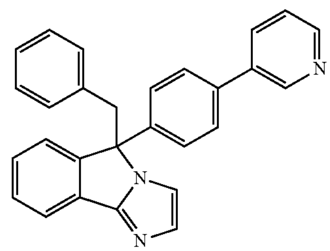 [SMILES: c1ccc(CC2(c3ccc(-c4cccnc4)cc3)c3ccccc3-c3nccn32)cc1] | 5-benzyl-5-(4-pyridin-3-ylphenyl)-5H-imidazo[2,1-a]isoindole | 400.1805 |
| 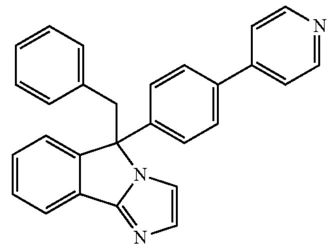 [SMILES: c1ccc(CC2(c3ccc(-c4ccncc4)cc3)c3ccccc3-c3nccn32)cc1] | 5-benzyl-5-(4-pyridin-4-ylphenyl)-5H-imidazo[2,1-a]isoindole | 400.1804 |
| 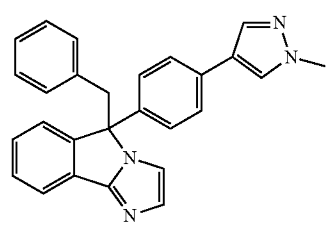 [SMILES: Cn1cc(-c2ccc(C3(Cc4ccccc4)c4ccccc4-c4nccn43)cc2)cn1] | 5-benzyl-5-[4-(1-methyl-1H-pyrazol-4-yl)phenyl]-5H-imidazo[2,1-a]isoindole | 403.1913 |
|  | 5-benzyl-5-(4-bromophenyl)-5H-imidazo[2,1-a]isoindole | 401.0648 |

-continued

| STRUCTURE | Chemical name | Mass found |
|---|---|---|
| 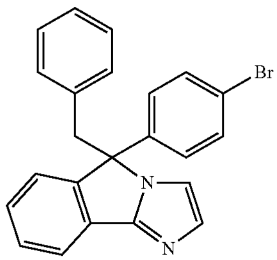 [SMILES: Brc1ccc(C2(Cc3ccccc3)c3ccccc3-c3nccn32)cc1] | 5-benzyl-5-(4-bromophenyl)-5H-imidazo[2,1-a]isoindole | 401.0647 |
| | 5-benzyl-5-[4-(1,3-thiazol-5-yl)phenyl]-5H-imidazo[2,1-a]isoindole | 406.137 |
| 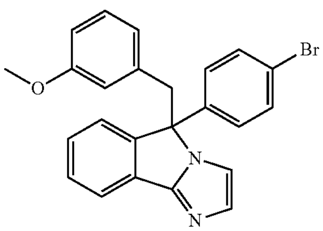 [SMILES: COc1cccc(CC2(c3ccc(Br)cc3)c3ccccc3-c3nccn32)c1] | 5-(4-bromophenyl)-5-(3-methoxybenzyl)-5H-imidazo[2,1-a]isoindole | 431.0753 |
| 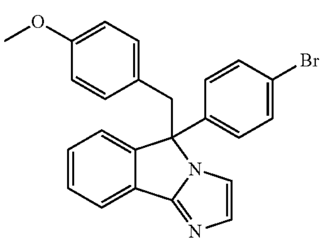 [SMILES: COc1ccc(CC2(c3ccc(Br)cc3)c3ccccc3-c3nccn32)cc1] | 5-(4-bromophenyl)-5-(4-methoxybenzyl)-5H-imidazo[2,1-a]isoindole | 431.0756 |
| 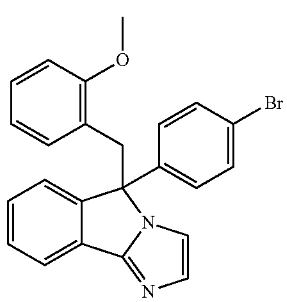 [SMILES: COc1ccccc1CC1(c2ccc(Br)cc2)c2ccccc2-c2nccn21] | 5-(4-bromophenyl)-5-(2-methoxybenzyl)-5H-imidazo[2,1-a]isoindole | 431.0754 |
| 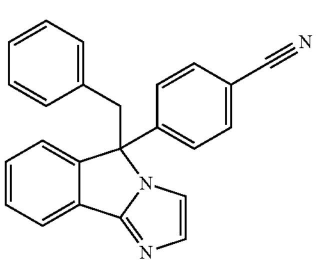 [SMILES: N#Cc1ccc(C2(Cc3ccccc3)c3ccccc3-c3nccn32)cc1] | 4-(5-benzyl-5H-imidazo[2,1-a]isoindole-5-yl)benzonitrile | 348.1497 |

-continued

| STRUCTURE | Chemical name | Mass found |
|---|---|---|
| 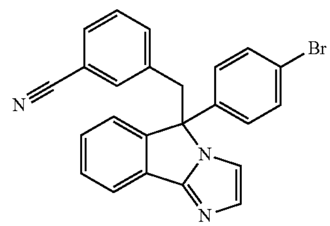 [SMILES: N#Cc1cccc(CC2(c3ccc(Br)cc3)c3ccccc3-c3nccn32)c1] | 3-{[5-(4-bromophenyl)-5H-imidazo[2,1-a]isoindole-5-yl]methyl}benzonitrile | 426.0603 |
| 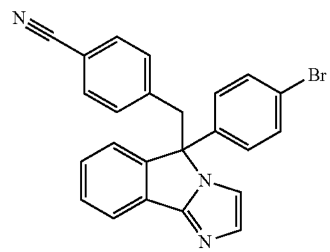 [SMILES: N#Cc1ccc(CC2(c3ccc(Br)cc3)c3ccccc3-c3nccn32)cc1] | 4-{[5-(4-bromophenyl)-5H-imidazo[2,1-a]isoindole-5-yl]methyl}benzonitrile | 426.0605 |
| 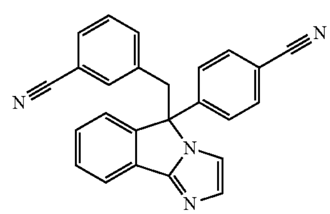 [SMILES: N#Cc1ccc(C2(Cc3cccc(C#N)c3)c3ccccc3-c3nccn32)cc1] | 3-{[5-(4-cyanophenyl)-5H-imidazo[2,1-a]isoindole-5-yl]methyl}benzonitrile | 373.1452 |
| | 4-(5-benzyl-5H-imidazo[2,1-a]isoindol-5-yl)benzonitrile | 348.1496 |
| | 4-(5-benzyl-5H-imidazo[2,1-a]isoindol-5-yl)benzonitrile | 348.1496 |
| 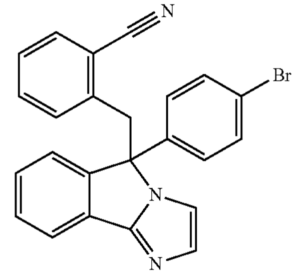 [SMILES: N#Cc1ccccc1CC1(c2ccc(Br)cc2)c2ccccc2-c2nccn21] | 2-{[5-(4-bromophenyl)-5H-imidazo[2,1-a]isoindol-5-yl]methyl}benzonitrile | 426.0607 |

| STRUCTURE | Chemical name | Mass found |
|---|---|---|
| 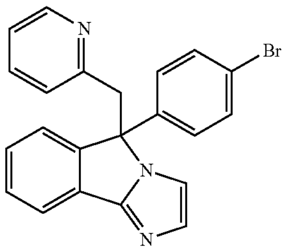 [SMILES: Brc1ccc(C2(Cc3ccccn3)c3ccccc3-c3nccn32)cc1] | 5-(4-bromophenyl)-5-(pyridin-2-ylmethyl)-5H-imidazo[2,1-a]isoindole | 402.0605 |
| 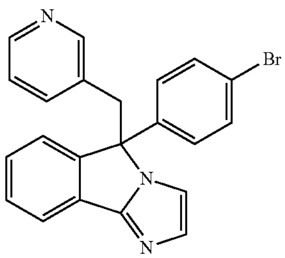 [SMILES: Brc1ccc(C2(Cc3cccnc3)c3ccccc3-c3nccn32)cc1] | 5-(4-bromophenyl)-5-(pyridin-3-ylmethyl)-5H-imidazo[2,1-a]isoindole | 402.0602 |
| 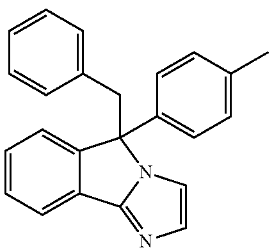 [SMILES: Cc1ccc(C2(Cc3ccccc3)c3ccccc3-c3nccn32)cc1] | 5-benzyl-5-(4-methylphenyl)-5H-imidazo[2,1-a]isoindole | 337.1689 |
| 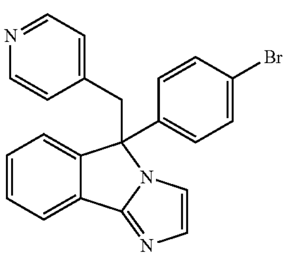 [SMILES: Brc1ccc(C2(Cc3ccncc3)c3ccccc3-c3nccn32)cc1] | 5-(4-bromophenyl)-5-(pyridin-4-ylmethyl)-5H-imidazo[2,1-a]isoindole | 402.0596 |
| 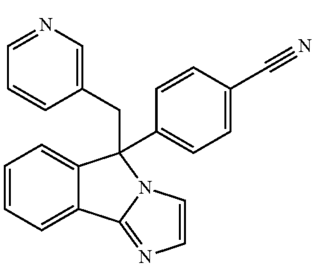 [SMILES: N#Cc1ccc(C2(Cc3cccnc3)c3ccccc3-c3nccn32)cc1] | 4-[5-(pyridin-3-ylmethyl)-5H-imidazo[2,1-a]isoindol-5-yl]benzonitrile | 349.1441 |
| 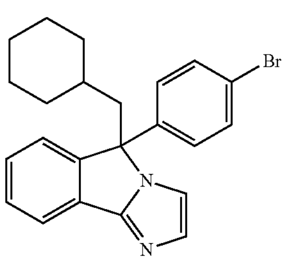 [SMILES: Brc1ccc(C2(CC3CCCCC3)c3ccccc3-c3nccn32)cc1] | 5-(4-bromophenyl)-5-(cyclohexylmethyl)-5H-imidazo[2,1-a]isoindole | 407.1129 |
| | 5-(4-bromophenyl)-5-(cyclobutylmethyl)-5H-imidazo[2,1-a]isoindole | 379.0813 |
| | 4-[5-(cyclohexylmethyl)-5H-imidazo[2,1-a]isoindol-5-yl]benzonitrile | 354.1971 |
| | 5-(4-bromophenyl)-5-(cyclopentylmethyl)-5H-imidazo[2,1-a]isoindole | 393.0971 |
| | 5-(4-bromophenyl)-5-(2-methylpropyl)-5H-imidazo[2,1-a]isoindole | 367.0815 |
| | 5-(4-bromophenyl)-5-(2-cyclohexylethyl)-5H-imidazo[2,1-a]isoindole | 421.129 |
| | 4-[5-(cyclopentylmethyl)-5H-imidazo[2,1-a]isoindol-5-yl]benzonitrile | 340.1811 |

| STRUCTURE | Chemical name | Mass found |
|---|---|---|
| 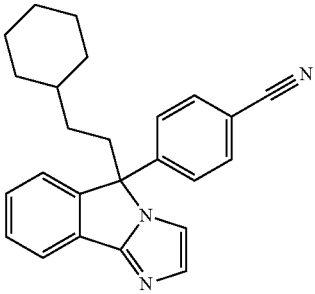 [SMILES: N#Cc1ccc(C2(CCC3CCCCC3)c3ccccc3-c3nccn32)cc1] | 4-[5-(2-cyclohexylethyl)-5H-imidazo[2,1-a]isoindol-5-yl]benzonitrile | 368.2125 |
| 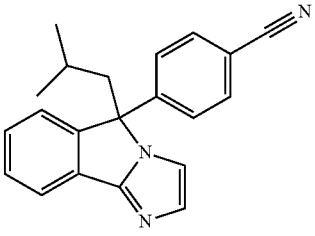 [SMILES: CC(C)CC1(c2ccc(C#N)cc2)c2ccccc2-c2nccn21] | 4-[5-(2-methylpropyl)-5H-imidazo[2,1-a]isoindol-5-yl]benzonitrile | 314.1657 |
| 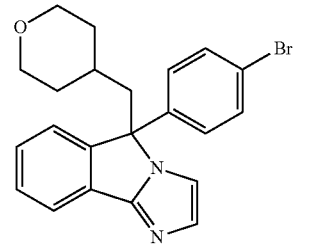 [SMILES: Brc1ccc(C2(CC3CCOCC3)c3ccccc3-c3nccn32)cc1] | 5-(4-bromophenyl)-5-(tetrahydro-2H-pyran-4-ylmethyl)-5H-imidazo[2,1-a]isoindole | 409.0922 |
| 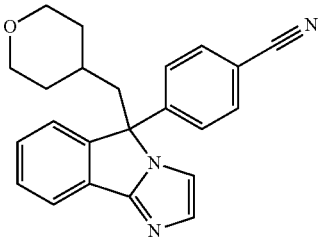 [SMILES: N#Cc1ccc(C2(CC3CCOCC3)c3ccccc3-c3nccn32)cc1] | 4-[5-(tetrahydro-2H-pyran-4-ylmethyl)-5H-imidazo[2,1-a]isoindol-5-yl]benzonitrile | 356.1764 |
| 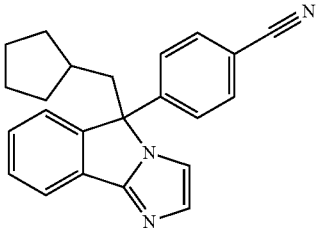 [SMILES: N#Cc1ccc(C2(CC3CCCC3)c3ccccc3-c3nccn32)cc1] | 4-[5-(cyclopentyl-methyl)-5H-imidazo[2,1-a]isoindol-5-yl]benzonitrile | 340.1814 |
| 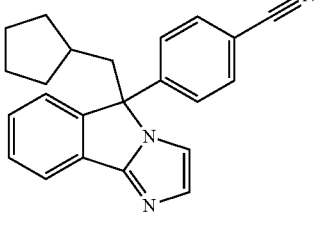 | 4-[5-(cyclopentyl-methyl)-5H-imidazo[2,1-a]isoindol-5-yl]benzonitrile | 340.1813 |
| 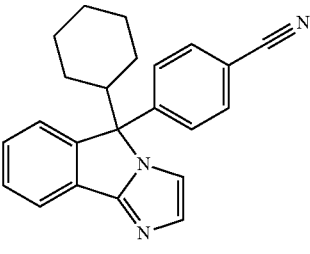 [SMILES: N#Cc1ccc(C2(C3CCCCC3)c3ccccc3-c3nccn32)cc1] | 4-(5-cyclohexyl-5H-imidazo[2,1-a]isoindol-5-yl)benzonitrile | 340.1812 |
| 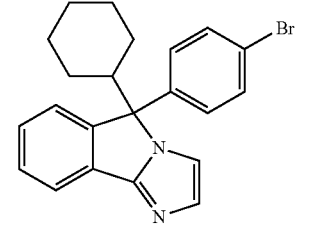 [SMILES: Brc1ccc(C2(C3CCCCC3)c3ccccc3-c3nccn32)cc1] | 5-(4-bromophenyl)-5-cyclohexyl-5H-imidazo[2,1-a]isoindole | 393.0975 |
| 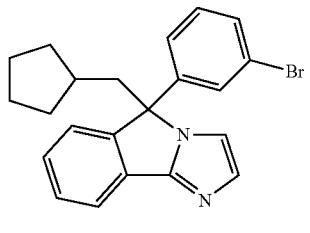 [SMILES: Brc1cccc(C2(CC3CCCC3)c3ccccc3-c3nccn32)c1] | 5-(3-bromophenyl)-5-(cyclopentyl-methyl)-5H-imidazo[2,1-a]isoindole | 393.0959 |
| 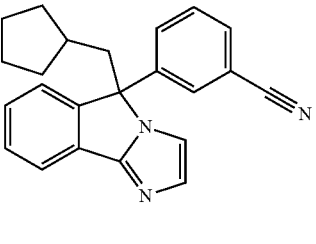 [SMILES: N#Cc1cccc(C2(CC3CCCC3)c3ccccc3-c3nccn32)c1] | 3-[5-(cyclopentyl-methyl)-5H-imidazo[2,1-a]isoindol-5-yl]benzonitrile | 340.1804 |
| 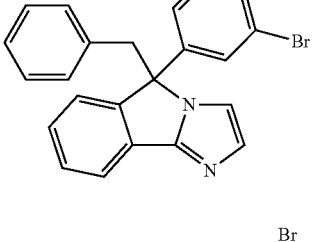 | 5-benzyl-5-(3-bromophenyl)-5H-imidazo[2,1-a]isoindole | 401.0649 |
| 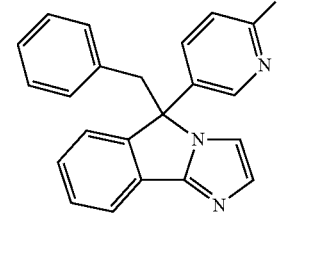 | 5-benzyl-5-(6-bromopyridin-3-yl)-5H-imidazo[2,1-a]isoindole | 402.0601 |

| STRUCTURE | Chemical name | Mass found |
|---|---|---|
| 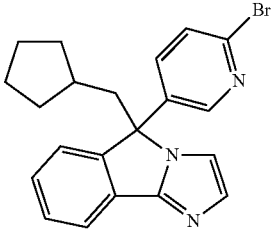 [SMILES: Brc1ccc(C2(CC3CCCC3)c3ccccc3-c3nccn32)cn1] | 5-(6-bromopyridin-3-yl)-5-(cyclopentyl-methyl)-5H-imidazo[2,1-a]isoindole | 394.0914 |
| 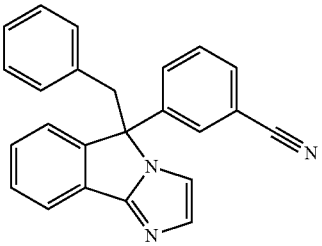 [SMILES: N#Cc1cccc(C2(Cc3ccccc3)c3ccccc3-c3nccn32)c1] | 3-(5-benzyl-5H-imidazo[2,1-a]isoindol-5-yl)benzonitrile | 348.1494 |
| 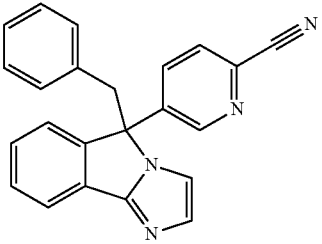 [SMILES: N#Cc1ccc(C2(Cc3ccccc3)c3ccccc3-c3nccn32)cn1] | 5-(5-benzyl-5H-imidazo[2,1-a]isoindol-5-yl)pyridine-2-carbonitrile | 349.1444 |
| 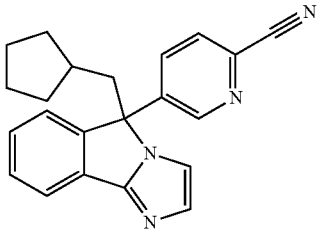 [SMILES: N#Cc1ccc(C2(CC3CCCC3)c3ccccc3-c3nccn32)cn1] | 5-[5-(cyclopentyl-methyl)-5H-imidazo[2,1-a]isoindol-5-yl]pyridine-2-carbonitrile | 341.1758 |
| 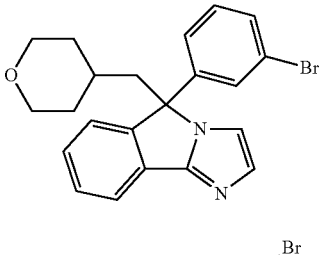 | 5-(3-bromophenyl)-5-(tetrahydro-2H-pyran-4-ylmethyl)-5H-imidazo[2,1-a]isoindole | 409.0909 |
| 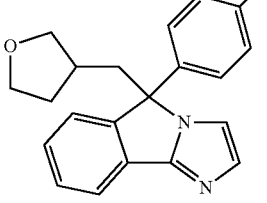 | 5-(4-bromophenyl)-5-(tetrahydrofuran-3-ylmethyl)-5H-imidazo[2,1-a]isoindole | 395.0755 |
| 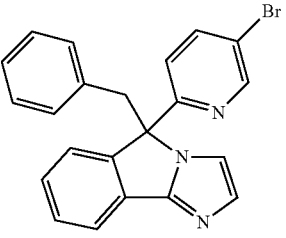 [SMILES: Brc1ccc(C2(Cc3ccccc3)c3ccccc3-c3nccn32)nc1] | 5-benzyl-5-(5-bromopyridin-2-yl)-5H-imidazo[2,1-a]isoindole | 402.0601 |
| 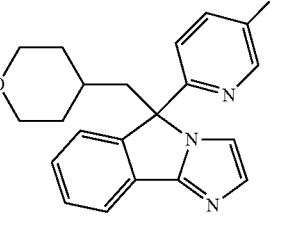 | 5-(5-bromopyridin-2-yl)-5-(tetrahydro-2H-pyran-4-ylmethyl)-5H-imidazo[2,1-a]isoindole | 410.0862 |
| 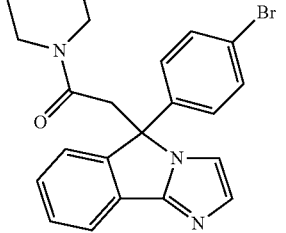 | 5-(4-bromophenyl)-5-(2-oxo-2-piperidin-1-ylethyl)-5H-imidazo[2,1-a]isoindole | 436.1024 |
| 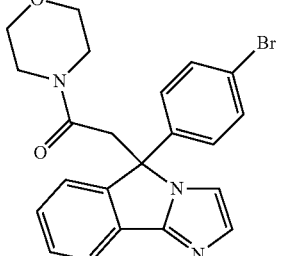 | 5-(4-bromophenyl)-5-(2-morpholin-4-yl-2-oxoethyl)-5H-imidazo[2,1-a]isoindole | 438.082 |
| 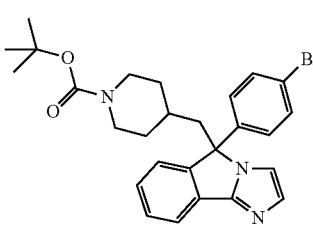 | tert-butyl 4-{[5-(4-bromophenyl)-5H-imidazo[2,1-a]isoindol-5-yl]methyl}piperidine-1-carboxylate | 508.1617 |
| 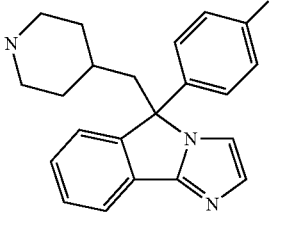 | 5-(4-bromophenyl)-5-(piperidin-4-ylmethyl)-5H-imidazo[2,1-a]isoindole | 408.1076 |

| STRUCTURE | Chemical name | Mass found |
|---|---|---|
| 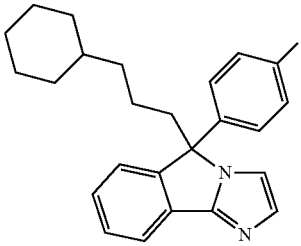 | 5-(4-bromophenyl)-5-(3-cyclohexylpropyl)-5H-imidazo[2,1-a]isoindole | 435.144 |
| 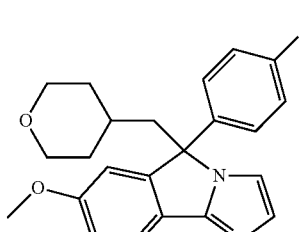 | 5-(4-chlorophenyl)-7-methoxy-5-(tetrahydro-2H-pyran-4-ylmethyl)-5H-imidazo[2,1-a]isoindole | 395.1528 |
| 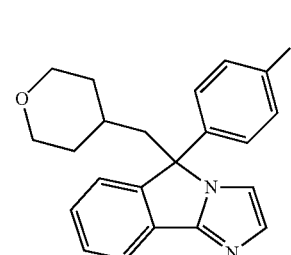 | 5-(4-chlorophenyl)-5-(tetrahydro-2H-pyran-4-ylmethyl)-5H-imidazo[2,1-a]isoindole | 365.1402 |
| 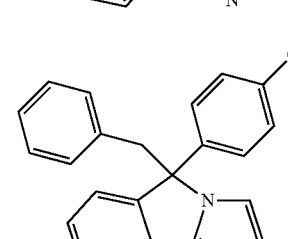 | 5-benzyl-5-(4-chlorophenyl)-5H-imidazo[2,1-a]isoindole | 357.1142 |
| 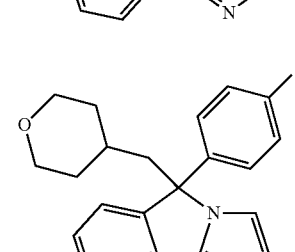 | 5-(4-fluorophenyl)-5-(tetrahydro-2H-pyran-4-ylmethyl)-5H-imidazo[2,1-a]isoindole | 349.1698 |
| 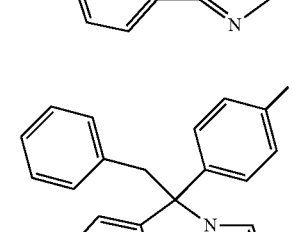 | 5-benzyl-5-(4-fluorophenyl)-5H-imidazo[2,1-a]isoindole | 341.1435 |

| STRUCTURE | Chemical name | Mass found |
|---|---|---|
| 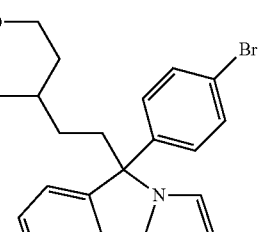 | 5-(4-bromophenyl)-5-[2-(tetrahydro-2H-pyran-4-yl)ethyl]-5H-imidazo[2,1-a]isoindole | 423.1067 |
| 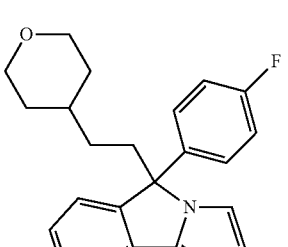 | 5-(4-fluorophenyl)-5-[2-(tetrahydro-2H-pyran-4-yl)ethyl]-5H-imidazo[2,1-a]isoindole | 363.1853 |
| 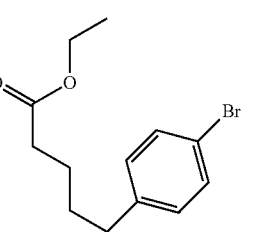 | ethyl 4-[5-(4-bromophenyl)-5H-imidazo[2,1-a]isoindol-5-yl]butanoate | 425.0853 |
| 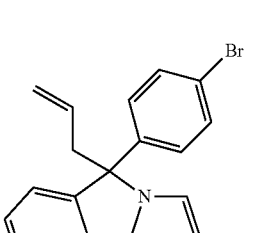 | 5-(4-bromophenyl)-5-prop-2-en-1-yl-5H-imidazo[2,1-a]isoindole | 351.0473 |
| 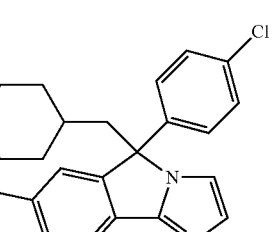 | 5-(4-chlorophenyl)-7-methoxy-5-(tetrahydro-2H-pyran-4-ylmethyl)-5H-imidazo[2,1-a]isoindole | 395.1531 |

-continued

| STRUCTURE | Chemical name | Mass found |
|---|---|---|
| 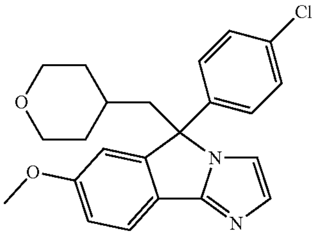 [SMILES: COc1ccc2c(c1)C(CC1CCOCC1)(c1ccc(Cl)cc1)n1ccnc1-2] | 5-(4-chlorophenyl)-7-methoxy-5-(tetrahydro-2H-pyran-4-ylmethyl)-5H-imidazo[2,1-a]isoindole | 395.153 |
| 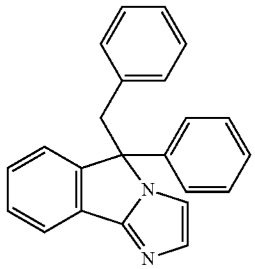 [SMILES: c1ccc(CC2(c3ccccc3)c3ccccc3-c3nccn32)cc1] | 5-benzyl-5-phenyl-5H-imidazo[2,1-a]isoindole | 322.147 |
| 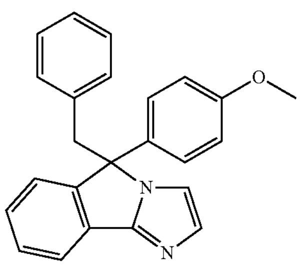 [SMILES: COc1ccc(C2(Cc3ccccc3)c3ccccc3-c3nccn32)cc1] | 5-benzyl-5-(4-methoxyphenyl)-5H-imidazo[2,1-a]isoindole | 353.17 |
| 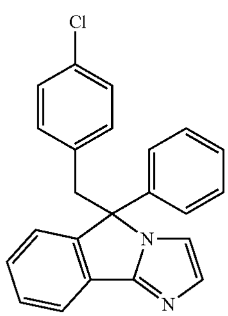 [SMILES: Clc1ccc(CC2(c3ccccc3)c3ccccc3-c3nccn32)cc1] | 5-(4-chlorobenzyl)-5-phenyl-5H-imidazo[2,1-a]isoindole | 357.17 |

-continued

| STRUCTURE | Chemical name | Mass found |
|---|---|---|
| 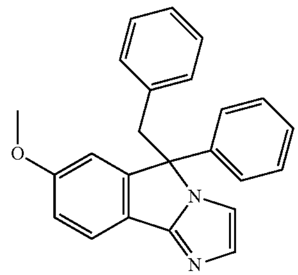 [SMILES: COc1ccc2c(c1)C(Cc1ccccc1)(c1ccccc1)n1ccnc1-2] | 5-benzyl-7-methoxy-5-phenyl-5H-imidazo[2,1-a]isoindole | 353.33 |
| 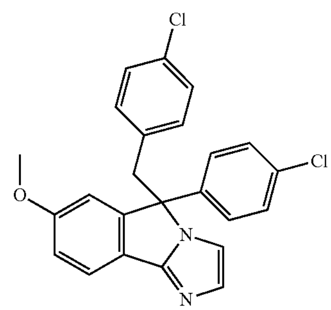 [SMILES: COc1ccc2c(c1)C(Cc1ccc(Cl)cc1)(c1ccc(Cl)cc1)n1ccnc1-2] | 5-(4-chlorobenzyl)-5-(4-chlorophenyl)-7-methoxy-5H-imidazo[2,1-a]isoindole | 421.09 |
| 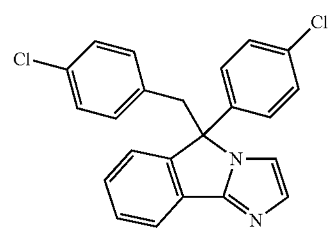 [SMILES: Clc1ccc(CC2(c3ccc(Cl)cc3)c3ccccc3-c3nccn32)cc1] | 5-(4-chlorobenzyl)-5-(4-chlorophenyl)-5H-imidazo[2,1-a]isoindole | 391.32 |

SCHEME V

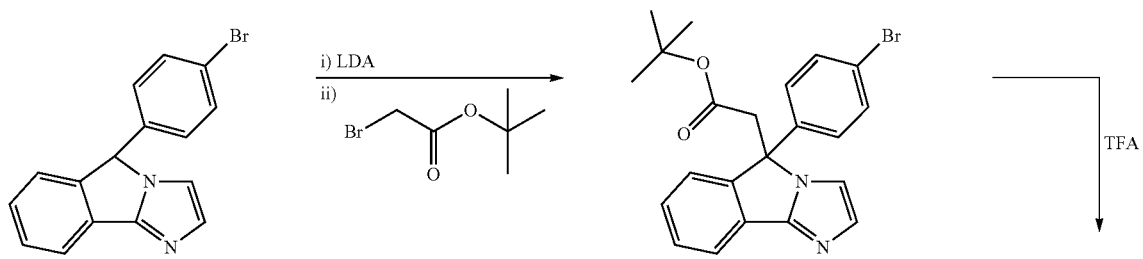

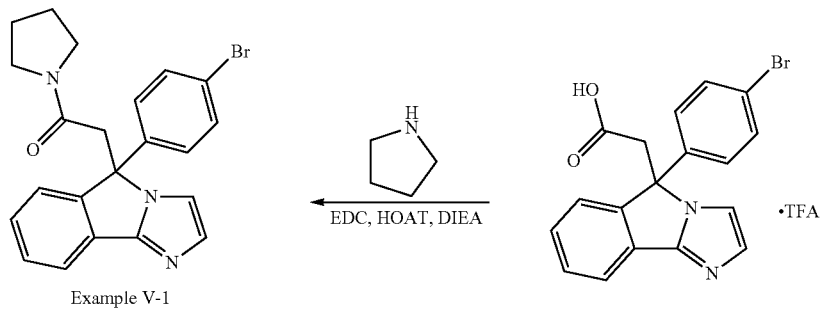

Example V-1

EXAMPLE V-I

Step 1: Tert-butyl[5-(4-bromophenyl)-5H-imidazo[2,1-a]isoindol-5-yl]acetate

To a solution of 5-(4-bromophenyl)-5H-imidazo[2,1-a]isoindole (3.17 g) in THF (60 mL) at −78° C. was added LAD solution (10.19 mL, 1.5 M in cyclohexane) drop wise. After stirring for 5 minutes tert-butyl bromoacetate was added, cooling bath was removed and the reaction mixture was stirred at room temperature. After 1.5 h the reaction was quenched with aqueous saturated $NH_4Cl$ and layers were separated. Aqueous layer was extracted with EtOAc (2×). Combined organic layers were dried over $Na_2SO_4$ and concentrated. Flash chromatography using a linear gradient of 1-50% EtOAc in hexanes afforded title compound as a white solid. Mass. found $(M+H)^+$, 427.0.

Step 2: 5-(4-bromophenyl)-5-(carboxymethyl)-5H-imidazo[2,1-a]isoindol-1-ium trifluoroacetate To a solution of tert-butyl[5-(4-bromophenyl)-5H-imidazo[2,1-a]isoindol-5-yl]acetate (3.22 g) in $CH_2Cl_2$ (10 mL) was added trifluoroacetic acid (10 mL). The reaction mixture was concentrated after stirring at room temperature for 6 h. The viscous material was dissolved in MeCN-water and lyophilized to a sticky solid. This material when dissolved and concentrated from toluene (3×) afforded the title compound as a white solid. Mass. found $(M+H)^+$, 371.0.

Step 5, Example V-1: 5-(4-bromophenyl)-5-(2-oxo-2-pyrrolidin-1-ylethyl)-5H-imidazo[2,1-a]isoindole To a mixture of EDC (49.2 mg) and HOAT (17.5 mg) was added a solution of 5-(4-bromophenyl)-5-(carboxymethyl)-5H-imidazo[2,1-a]isoindol-1-ium trifluoroacetate (62 mg) and Hunig's base (0.134 mL) in DMF (1 mL) followed by pyrrolidine (22.8 mg). The reaction mixture was stirred overnight at room temperature and was then purified by reversed phase HPLC (21×100 mm Phenomenex Gemini, 15-70% MeCN/water containing 0.05% $NH_4OH$ over 20 min at 20 mL/min) to give title compound as a white solid. HRMS. Found, 422.0873; calcd for $(M+H)^+$, 422.0863. $^1$H NMR (500 MHz, $CDCl_3$): δ 7.84 (d, J=7.60 Hz, 1 H); 7.47 (d, J=1.30 Hz, 1 H); 7.42-7.39 (m, 3 H); 7.29-7.26 (m, 3 H); 6.91 (dd, J=21.03, 8.48 Hz, 2 H); 3.71 (d, J=16.82 Hz, 1 H); 3.42 (t, J=6.89 Hz, 2 H); 3.34 (dt, J=9.85, 6.85 Hz, 1 H); 3.18 (dt, J=9.89, 6.80 Hz, 1 H); 2.86 (d, J=16.81 Hz, 1 H); 1.95-1.79 (m, 4 H).

The following compounds were prepared using the experimental procedure described above for Scheme V.

| STRUCTURE | Chemical name | Mass found |
|---|---|---|
| 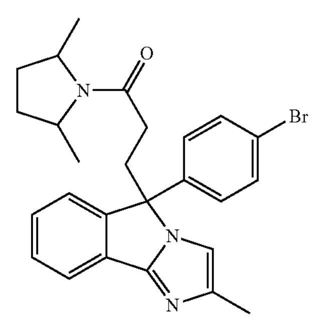 [SMILES: Cc1cn2c(n1)-c1ccccc1C2(CCC(=O)N1C(C)CCC1C)c1ccc(Br)cc1] | 5-(4-bromophenyl)-5-[3-(2,5-dimethylpyrrolidin-1-yl)-3-oxopropyl]-2-methyl-5H-imidazo[2,1-a]isoindole | 478.1484 |

-continued

| STRUCTURE | Chemical name | Mass found |
|---|---|---|
| 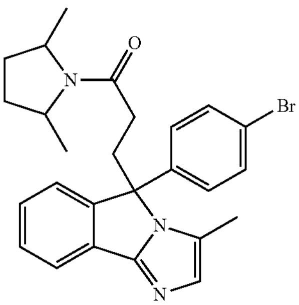 [SMILES: Cc1cnc2n1C(CCC(=O)N1C(C)CCC1C)(c1ccc(Br)cc1)c1ccccc1-2] | 5-(4-bromophenyl)-5-[3-(2,5-dimethylpyrrolidin-1-yl)-3-oxopropyl]-3-methyl-5H-imidazo[2,1-a]isoindole | 478.1487 |
| 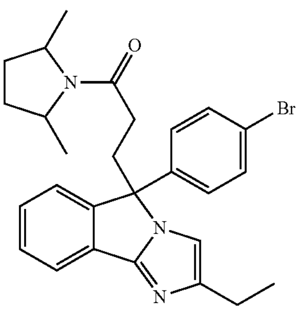 [SMILES: CCc1cn2c(n1)-c1ccccc1C2(CCC(=O)N1C(C)CCC1C)c1ccc(Br)cc1] | 5-(4-bromophenyl)-5-[3-(2,5-dimethylpyrrolidin-1-yl)-3-oxopropyl]-2-ethyl-5H-imidazo[2,1-a]isoindole | 492.1632 |
| 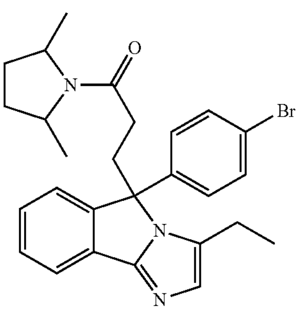 [SMILES: CCc1cnc2n1C(CCC(=O)N1C(C)CCC1C)(c1ccc(Br)cc1)c1ccccc1-2] | 5-(4-bromophenyl)-5-[3-(2,5-dimethylpyrrolidin-1-yl)-3-oxopropyl]-3-ethyl-5H-imidazo[2,1-a]isoindole | 492.1632 |
| 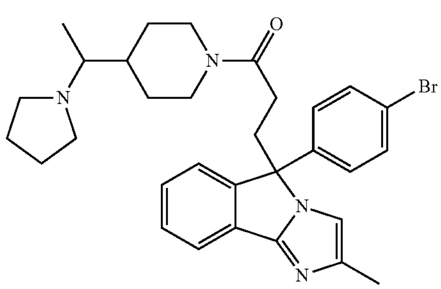 [SMILES: Cc1cn2c(n1)-c1ccccc1C2(CCC(=O)N1CCC(C(C)N2CCCC2)CC1)c1ccc(Br)cc1] | 5-(4-bromophenyl)-2-methyl-5-{3-oxo-3-[4-(1-pyrrolidin-1-ylethyl)piperidin-1-yl]propyl}-5H-imidazo[2,1-a]isoindole | 561.2213 |
| 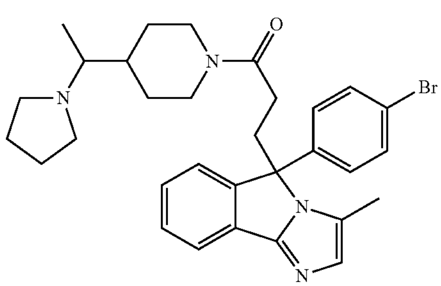 [SMILES: Cc1cnc2n1C(CCC(=O)N1CCC(C(C)N3CCCC3)CC1)(c1ccc(Br)cc1)c1ccccc1-2] | 5-(4-bromophenyl)-3-methyl-5-{3-oxo-3-[4-(1-pyrrolidin-1-ylethyl)piperidin-1-yl]propyl}-5H-imidazo[2,1-a]isoindole | 561.2212 |

-continued

| STRUCTURE | Chemical name | Mass found |
|---|---|---|
| 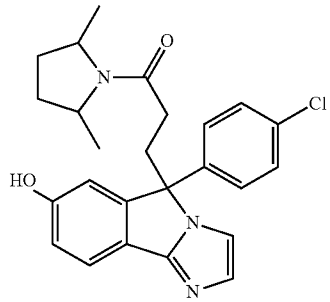 [SMILES: CC1CCC(C)N1C(=O)CCC1(c2ccc(Cl)cc2)c2cc(O)ccc2-c2nccn21] | 5-(4-chlorophenyl)-5-[3-(2,5-dimethylpyrrolidin-1-yl)-3-oxopropyl]-5H-imidazo[2,1-a]isoindol-7-ol | 436.1778 |
| 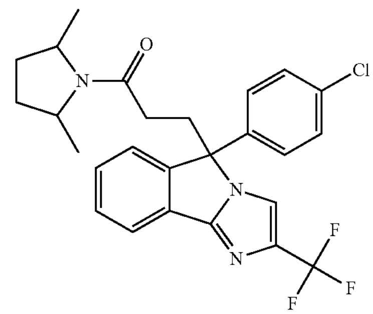 [SMILES: CC1CCC(C)N1C(=O)CCC1(c2ccc(Cl)cc2)c2ccccc2-c2nc(C(F)(F)F)cn21] | 5-(4-chlorophenyl)-5-[3-(2,5-dimethylpyrrolidin-1-yl)-3-oxopropyl]-2-(trifluoromethyl)-5H-imidazo[2,1-a]isoindole | 488.17 |
| 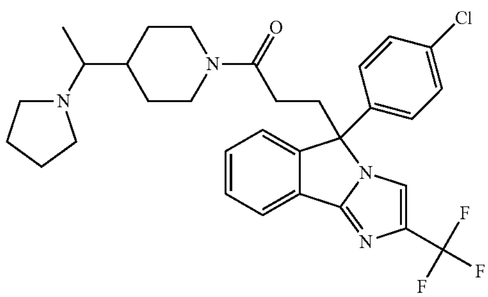 [SMILES: CC(C1CCN(C(=O)CCC2(c3ccc(Cl)cc3)c3ccccc3-c3nc(C(F)(F)F)cn32)CC1)N1CCCC1] | 5-(4-chlorophenyl)-5-{3-oxo-3-[4-(1-pyrrolidin-1-ylethyl)piperidin-1-yl]propyl}-2-(trifluoromethyl)-5H-imidazo[2,1-a]isoindole | 571.2437 |
| 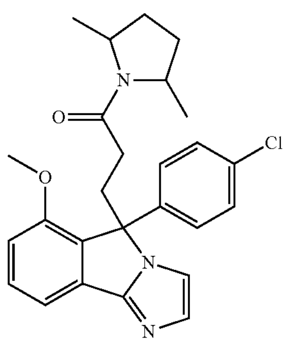 [SMILES: COc1cccc2c1C(CCC(=O)N1C(C)CCC1C)(c1ccc(Cl)cc1)n1ccnc1-2] | 5-(4-chlorophenyl)-5-[3-(2,5-dimethylpyrrolidin-1-yl)-3-oxopropyl]-6-methoxy-5H-imidazo[2,1-a]isoindole | 450.1935 |
| 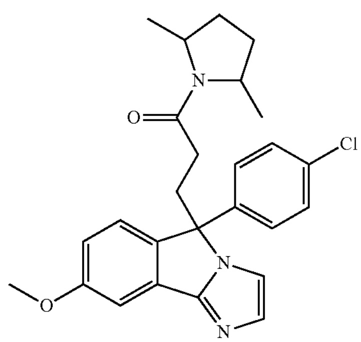 [SMILES: COc1ccc2c(c1)-c1nccn1C2(CCC(=O)N1C(C)CCC1C)c1ccc(Cl)cc1] | 5-(4-chlorophenyl)-5-[3-(2,5-dimethylpyrrolidin-1-yl)-3-oxopropyl]-8-methoxy-5H-imidazo[2,1-a]isoindole | 450.1934 |

| STRUCTURE | Chemical name | Mass found |
|---|---|---|
| 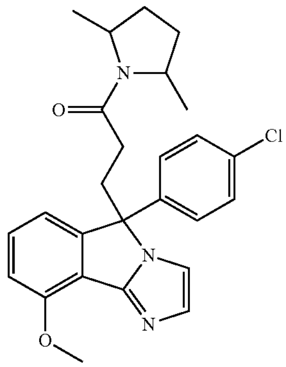 [SMILES: COc1cccc2c1-c1nccn1C2(CCC(=O)N1C(C)CCC1C)c1ccc(Cl)cc1] | 5-(4-chlorophenyl)-5-[3-(2,5-dimethylpyrrolidin-1-yl)-3-oxopropyl]-9-methoxy-5H-imidazo[2,1-a]isoindole | 450.1935 |
| | 3-[5-(4-chlorophenyl)-6-methoxy-5H-imidazo[2,1-a]isoindol-5-yl]-N,N-diethylpropanamide | 424.1779 |
| | 3-[5-(4-chlorophenyl)-6-methoxy-5H-imidazo[2,1-a]isoindol-5-yl]-N,N-diethylpropanamide | 424.1783 |
| | 3-[5-(4-chlorophenyl)-6-methoxy-5H-imidazo[2,1-a]isoindol-5-yl]-N,N-diethylpropanamide | 424.1786 |
| 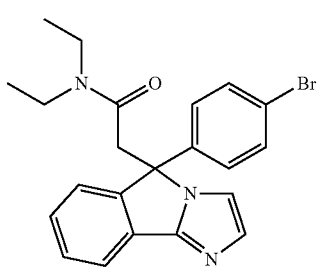 [SMILES: CCN(CC)C(=O)CC1(c2ccc(Br)cc2)c2ccccc2-c2nccn21] | 2-[5-(4-bromophenyl)-5H-imidazo[2,1-a]isoindol-5-yl]-N,N-diethylacetamide | 424.1039 |

-continued

| STRUCTURE | Chemical name | Mass found |
|---|---|---|
| 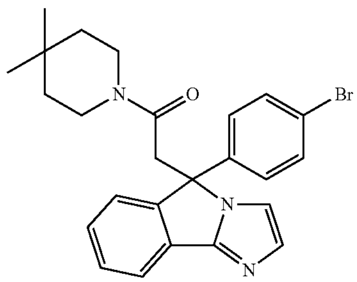 [SMILES: CC1(C)CCN(C(=O)CC2(c3ccc(Br)cc3)c3ccccc3-c3nccn32)CC1] | 5-(4-bromophenyl)-5-[2-(4,4-dimethylpiperidin-1-yl)-2-oxoethyl]-5H-imidazo[2,1-a]isoindole | 464.1356 |
| 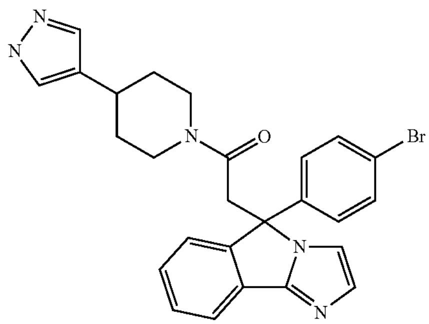 [SMILES: O=C(CC1(c2ccc(Br)cc2)c2ccccc2-c2nccn21)N1CCC(c2cn[nH]c2)CC1] | 5-(4-bromophenyl)-5-{2-oxo-2-[4-(1H-pyrazol-4-yl)piperidin-1-yl]ethyl}-5H-imidazo[2,1-a]isoindole | 502.1265 |
| 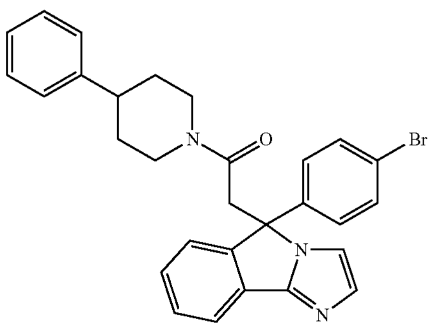 [SMILES: O=C(CC1(c2ccc(Br)cc2)c2ccccc2-c2nccn21)N1CCC(c2ccccc2)CC1] | 5-(4-bromophenyl)-5-[2-oxo-2-(4-phenylpiperidin-1-yl)ethyl]-5H-imidazo[2,1-a]isoindole | 512.1368 |
| 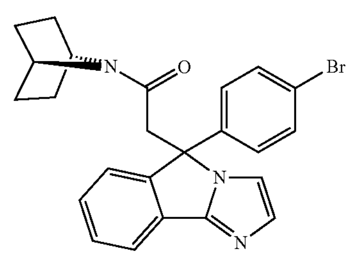 [SMILES: O=C(CC1(c2ccc(Br)cc2)c2ccccc2-c2nccn21)N1[C@H]2CC[C@@H]1CC2] | 5-{2-[(1s,4s)-7-azabicyclo[2.2.1]hept-7-yl]-2-oxoethyl}-5-(4-bromophenyl)-5H-imidazo[2,1-a]isoindole | 448.1041 |
| 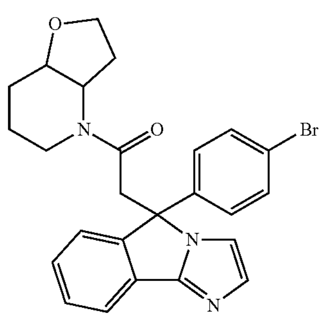 [SMILES: O=C(CC1(c2ccc(Br)cc2)c2ccccc2-c2nccn21)N1CCCC2OCCC21] | 5-(4-bromophenyl)-5-[2-(hexahydrofuro[3,2-b]pyridin-4(2H)-yl)-2-oxoethyl]-5H-imidazo[2,1-a]isoindole | 478.1151 |

-continued

| STRUCTURE | Chemical name | Mass found |
|---|---|---|
| 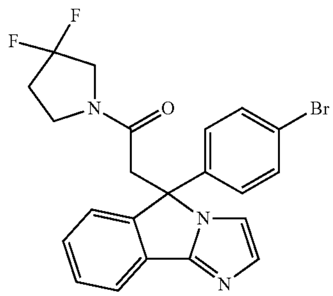 [SMILES: O=C(CC1(c2ccc(Br)cc2)c2ccccc2-c2nccn21)N1CCC(F)(F)C1] | 5-(4-bromophenyl)-5-[2-(3,3-difluoropyrrolidin-1-yl)-2-oxoethyl]-5H-imidazo[2,1-a]isoindole | 458.0699 |
| 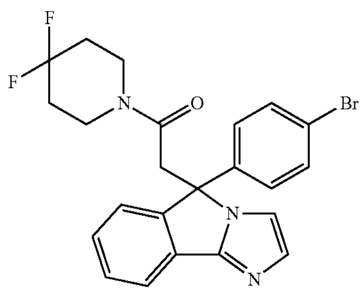 [SMILES: O=C(CC1(c2ccc(Br)cc2)c2ccccc2-c2nccn21)N1CCC(F)(F)CC1] | 5-(4-bromophenyl)-5-[2-(4,4-difluoropiperidin-1-yl)-2-oxoethyl]-5H-imidazo[2,1-a]isoindole | 472.0859 |
| 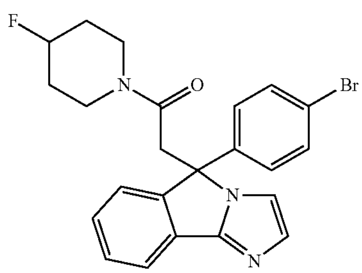 [SMILES: O=C(CC1(c2ccc(Br)cc2)c2ccccc2-c2nccn21)N1CCC(F)CC1] | 5-(4-bromophenyl)-5-[2-(4-fluoropiperidin-1-yl)-2-oxoethyl]-5H-imidazo[2,1-a]isoindole | 454.0947 |
| 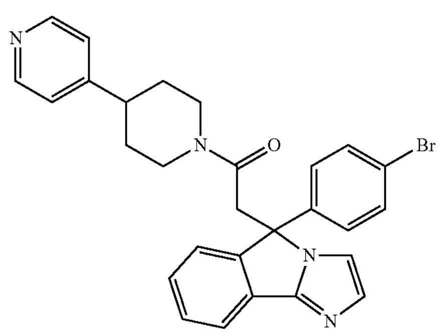 [SMILES: O=C(CC1(c2ccc(Br)cc2)c2ccccc2-c2nccn21)N1CCC(c2ccncc2)CC1] | 5-(4-bromophenyl)-5-[2-oxo-2-(4-pyridin-4-ylpiperidin-1-yl)ethyl]-5H-imidazo[2,1-a]isoindole | 513.1316 |
| 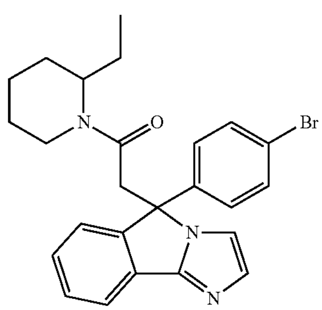 [SMILES: CCC1CCCCN1C(=O)CC1(c2ccc(Br)cc2)c2ccccc2-c2nccn21] | 5-(4-bromophenyl)-5-[2-(2-ethylpiperidin-1-yl)-2-oxoethyl]-5H-imidazo[2,1-a]isoindole | 464.1352 |

| STRUCTURE | Chemical name | Mass found |
|---|---|---|
| 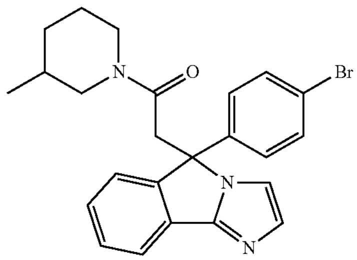 [SMILES: CC1CCCN(C(=O)CC2(c3ccc(Br)cc3)c3ccccc3-c3nccn32)C1] | 5-(4-bromophenyl)-5-[2-(3-methylpiperidin-1-yl)-2-oxoethyl]-5H-imidazo[2,1-a]isoindole | 450.1196 |
| 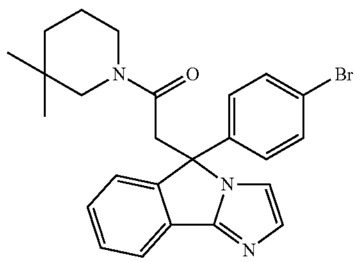 [SMILES: CC1(C)CCCN(C(=O)CC2(c3ccc(Br)cc3)c3ccccc3-c3nccn32)C1] | 5-(4-bromophenyl)-5-[2-(3,3-dimethylpiperidin-1-yl)-2-oxoethyl]-5H-imidazo[2,1-a]isoindole | 464.1354 |
| 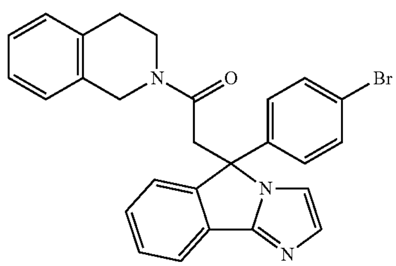 [SMILES: O=C(CC1(c2ccc(Br)cc2)c2ccccc2-c2nccn21)N1CCc2ccccc2C1] | 5-(4-bromophenyl)-5-[2-(3,4-dihydroisoquinolin-2(1H)-yl)-2-oxoethyl]-5H-imidazo[2,1-a]isoindole | 484.1049 |
| 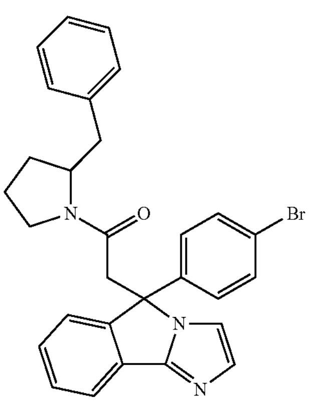 [SMILES: O=C(CC1(c2ccc(Br)cc2)c2ccccc2-c2nccn21)N1CCCC1Cc1ccccc1] | 5-[2-(2-benzylpyrrolidin-1-yl)-2-oxoethyl]-5-(4-bromophenyl)-5H-imidazo[2,1-a]isoindole | 512.1365 |
| 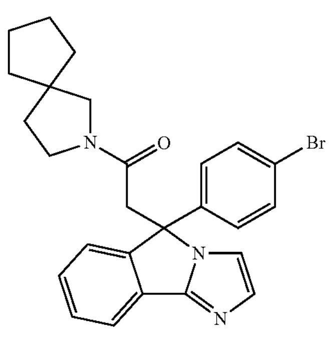 [SMILES: O=C(CC1(c2ccc(Br)cc2)c2ccccc2-c2nccn21)N1CCC2(CCCC2)C1] | 5-[2-(2-azaspiro[4.4]non-2-yl)-2-oxoethyl]-5-(4-bromophenyl)-5H-imidazo[2,1-a]isoindole | 476.1356 |

| STRUCTURE | Chemical name | Mass found |
|---|---|---|
| 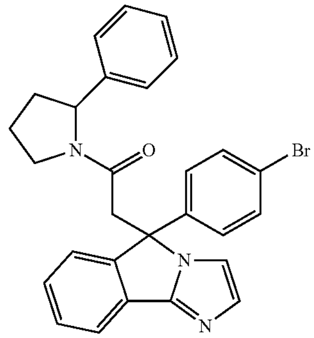 [SMILES: O=C(CC1(c2ccc(Br)cc2)c2ccccc2-c2nccn21)N1CCCC1c1ccccc1] | 5-(4-bromophenyl)-5-[2-oxo-2-(2-phenylpyrrolidin-1-yl)ethyl]-5H-imidazo[2,1-a]isoindole | 498.1206 |
| 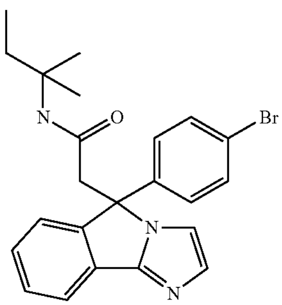 [SMILES: CCC(C)(C)NC(=O)CC1(c2ccc(Br)cc2)c2ccccc2-c2nccn21] | 2-[5-(4-bromophenyl)-5H-imidazo[2,1-a]isoindol-5-yl]-N-(3-hydroxy-1,1-dimethylbutyl)acetamide | 468.131 |
| 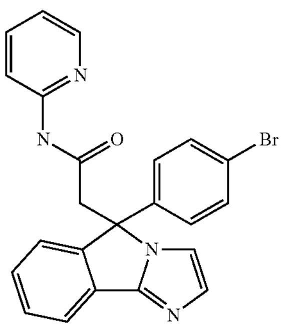 [SMILES: O=C(CC1(c2ccc(Br)cc2)c2ccccc2-c2nccn21)Nc1ccccn1] | 2-[5-(4-bromophenyl)-5H-imidazo[2,1-a]isoindol-5-yl]-N-pyridin-2-ylacetamide | 445.0682 |
| 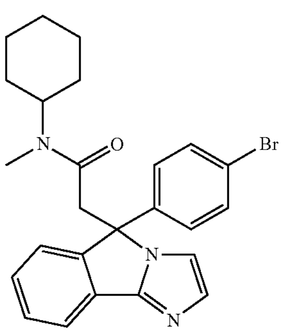 [SMILES: CN(C(=O)CC1(c2ccc(Br)cc2)c2ccccc2-c2nccn21)C1CCCCC1] | 2-[5-(4-bromophenyl)-5H-imidazo[2,1-a]isoindol-5-yl]-N-cyclohexyl-N-methylacetamide | 464.1351 |
| 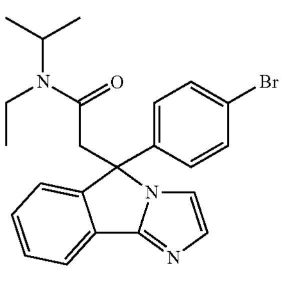 [SMILES: CCN(C(=O)CC1(c2ccc(Br)cc2)c2ccccc2-c2nccn21)C(C)C] | 2-[5-(4-bromophenyl)-5H-imidazo[2,1-a]isoindol-5-yl]-N-ethyl-N-(1-methylethyl)acetamide | 438.1193 |

-continued
| STRUCTURE | Chemical name | Mass found |
|---|---|---|
| 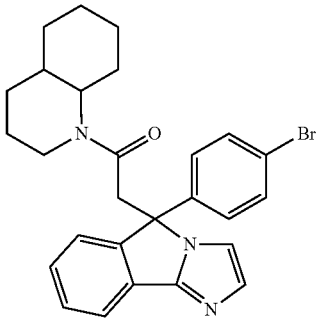 [SMILES: O=C(CC1(c2ccc(Br)cc2)c2ccccc2-c2nccn21)N1CCCC2CCCCC21] | 5-(4-bromophenyl)-5-[2-(octahydroquinolin-1(2H)-yl)-2-oxoethyl]-5H-imidazo[2,1-a]isoindole | 490.1519 |
| 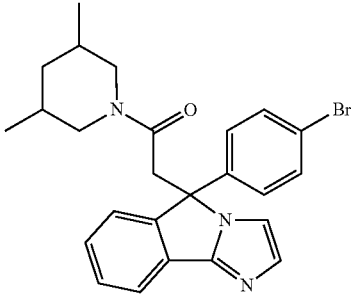 [SMILES: CC1CC(C)CN(C(=O)CC2(c3ccc(Br)cc3)c3ccccc3-c3nccn32)C1] | 5-(4-bromophenyl)-5-[2-(3,5-dimethylpiperidin-1-yl)-2-oxoethyl]-5H-imidazo[2,1-a]isoindole | 464.1355 |
| 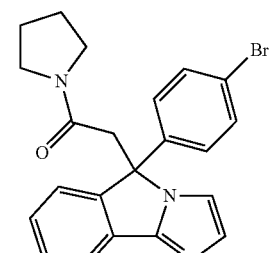 | 5-(4-bromophenyl)-5-(2-oxo-2-pyrrolidin-1-ylethyl)-5H-imidazo[2,1-a]isoindoe | 422.0873 |
| 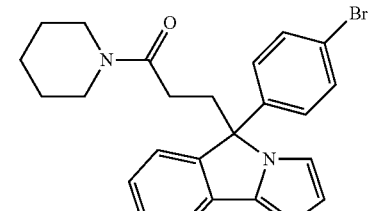 | 5-(4-bromophenyl)-5-(3-oxo-3-piperidin-1-ylpropyl)-5H-imidazo[2,1-a]isoindole | 450.1181 |
| 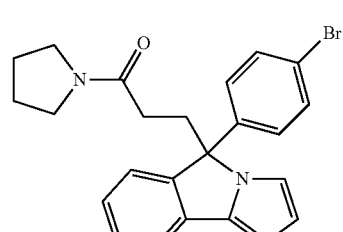 | 5-(4-bromophenyl)-5-(3-oxo-3-pyrrolidin-1-ylpropyl)-5H-imidazo[2,1-a]isoindole | 436.1023 |

| STRUCTURE | Chemical name | Mass found |
|---|---|---|
| 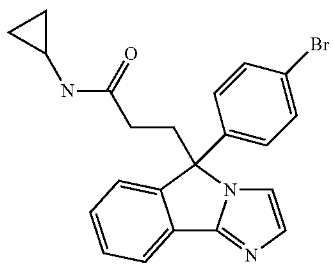 [SMILES: O=C(CCC1(c2ccc(Br)cc2)c2ccccc2-c2nccn21)NC1CC1] | 3-[5-(4-bromophenyl)-5H-imidazo[2,1-a]isoindol-5-yl]-N-cyclopropylpropanamide | 422.0874 |
| 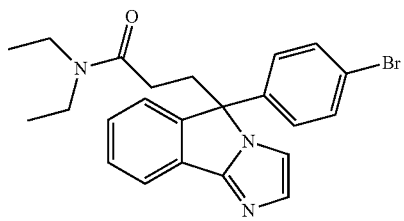 [SMILES: CCN(CC)C(=O)CCC1(c2ccc(Br)cc2)c2ccccc2-c2nccn21] | 3-[5-(4-bromophenyl)-5H-imidazo[2,1-a]isoindol-5-yl]-N,N-diethylpropanamide | 438.1197 |
| 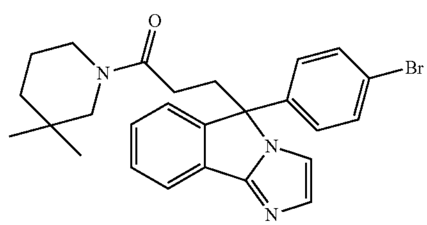 [SMILES: CC1(C)CCCN(C(=O)CCC2(c3ccc(Br)cc3)c3ccccc3-c3nccn32)C1] | 5-(4-bromophenyl)-5-[3-(3,3-dimethylpiperidin-1-yl)-3-oxopropyl]-5H-imidazo[2,1-a]isoindole | 478.1489 |
| 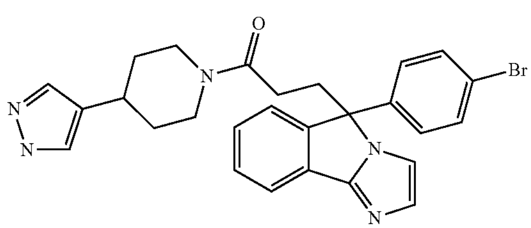 [SMILES: O=C(CCC1(c2ccc(Br)cc2)c2ccccc2-c2nccn21)N1CCC(c2cn[nH]c2)CC1] | 5-(4-bromophenyl)-5-{3-oxo-3-[4-(1H-pyrazol-4-yl)piperidin-1-yl]propyl}-5H-imidazo[2,1-a]isoindole | 516.14 |
| 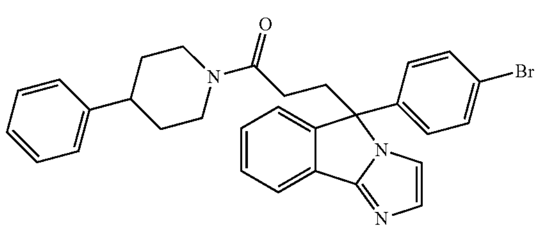 [SMILES: O=C(CCC1(c2ccc(Br)cc2)c2ccccc2-c2nccn21)N1CCC(c2ccccc2)CC1] | 5-(4-bromophenyl)-5-[3-oxo-3-(4-phenylpiperidin-1-yl)propyl]-5H-imidazo[2,1-a]isoindole | 526.1505 |
| 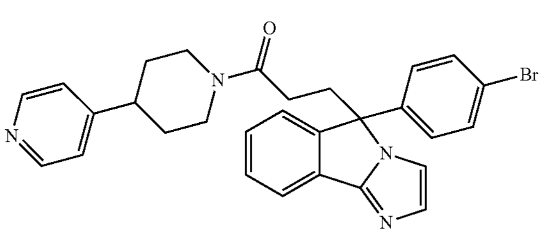 [SMILES: O=C(CCC1(c2ccc(Br)cc2)c2ccccc2-c2nccn21)N1CCC(c2ccncc2)CC1] | 5-(4-bromophenyl)-5-[3-oxo-3-(4-pyridin-4-ylpiperidin-1-yl)propyl]-5H-imidazo[2,1-a]isoindole | 527.1451 |

-continued

| STRUCTURE | Chemical name | Mass found |
|---|---|---|
| 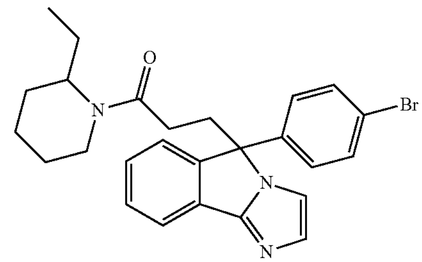 [SMILES: CCC1CCCCN1C(=O)CCC1(c2ccc(Br)cc2)c2ccccc2-c2nccn21] | 5-(4-bromophenyl)-5-[3-(2-ethylpiperidin-1-yl)-3-oxopropyl]-5H-imidazo[2,1-a]isoindole | 478.1501 |
| 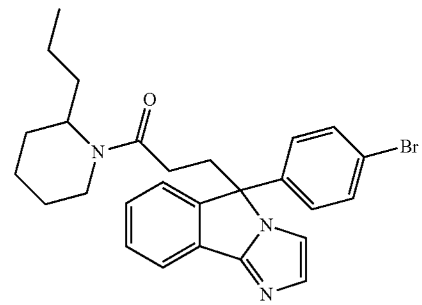 [SMILES: CCCC1CCCCN1C(=O)CCC1(c2ccc(Br)cc2)c2ccccc2-c2nccn21] | 5-(4-bromophenyl)-5-[3-oxo-3-(2-propylpiperidin-1-yl)propyl]-5H-imidazo[2,1-a]isoindole | 492.1656 |
| 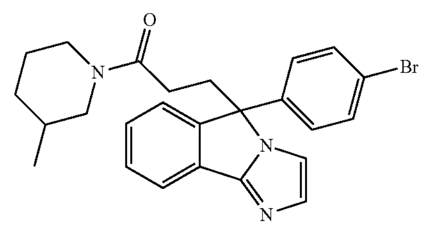 | 5-(4-bromophenyl)-5-[3-(3-methylpiperidin-1-yl)-3-oxopropyl]-5H-imidazo[2,1-a]isoindole | 464.1333 |
| 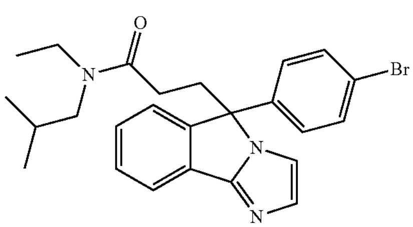 [SMILES: CCN(CC(C)C)C(=O)CCC1(c2ccc(Br)cc2)c2ccccc2-c2nccn21] | 5-(4-bromophenyl)-5-[3-(3,5-dimethylpiperidin-1-yl)-3-oxopropyl]-5H-imidazo[2,1-a]isoindole | 478.1495 |
| 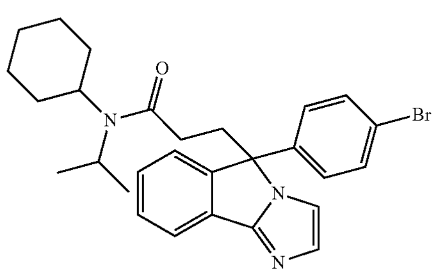 [SMILES: CC(C)N(C(=O)CCC1(c2ccc(Br)cc2)c2ccccc2-c2nccn21)C1CCCCC1] | 3-[5-(4-bromophenyl)-5H-imidazo[2,1-a]isoindol-5-yl]-N-cyclohexyl-N-(1-methylethyl)propanamide | 506.182 |
| 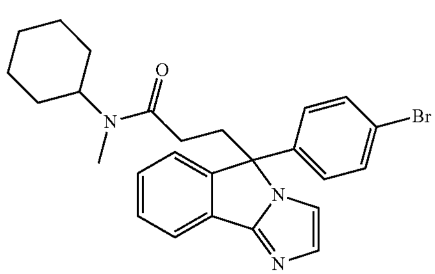 [SMILES: CN(C(=O)CCC1(c2ccc(Br)cc2)c2ccccc2-c2nccn21)C1CCCCC1] | 3-[5-(4-bromophenyl)-5H-imidazo[2,1-a]isoindol-5-yl]-N-cyclohexyl-N-methylpropanamide | 478.1493 |

| STRUCTURE | Chemical name | Mass found |
|---|---|---|
| 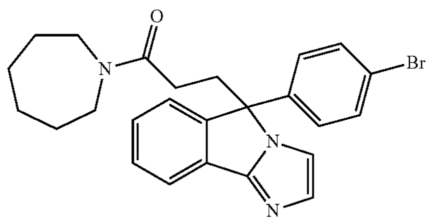 [SMILES: O=C(CCC1(c2ccc(Br)cc2)c2ccccc2-c2nccn21)N1CCCCCC1] | 5-(3-azepan-1-yl-3-oxopropyl)-5-(4-bromophenyl)-5H-imidazo[2,1-a]isoindole | 464.1345 |
| 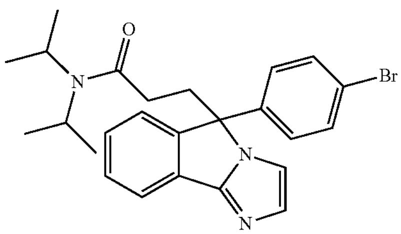 [SMILES: CC(C)N(C(=O)CCC1(c2ccc(Br)cc2)c2ccccc2-c2nccn21)C(C)C] | 3-[5-(4-bromophenyl)-5H-imidazo[2,1-a]isoindol-5-yl]-N,N-bis(1-methylethyl)propanamide | 466.1502 |
| 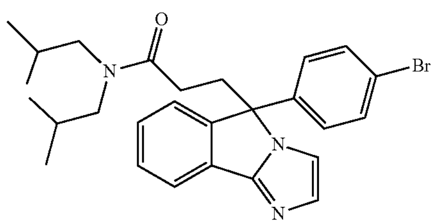 | 3-[5-(4-bromophenyl)-5H-imidazo[2,1-a]isoindol-5-yl]-N,N-bis(2-methylpropyl)propanamide | 494.1826 |
| 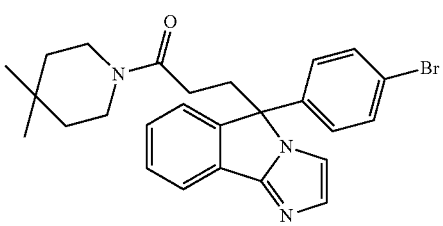 [SMILES: CC1(C)CCN(C(=O)CCC2(c3ccc(Br)cc3)c3ccccc3-c3nccn32)CC1] | 5-(4-bromophenyl)-5-[3-(4,4-dimethylpiperidin-1-yl)-3-oxopropyl]-5H-imidazo[2,1-a]isoindole | 478.1485 |
| 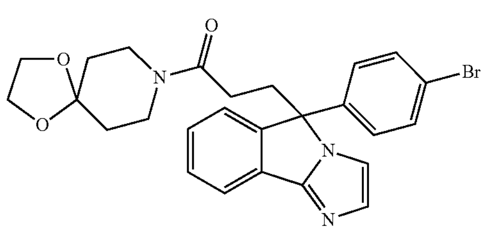 [SMILES: O=C(CCC1(c2ccc(Br)cc2)c2ccccc2-c2nccn21)N1CCC2(CC1)OCCO2] | 5-(4-bromophenyl)-5-[3-(1,4-dioxa-8-azaspiro[4.5]dec-8-yl)-3-oxopropyl]-5H-imidazo[2,1-a]isoindole | 508.1264 |
| 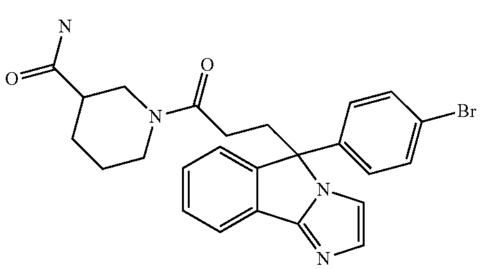 [SMILES: NC(=O)C1CCCN(C(=O)CCC2(c3ccc(Br)cc3)c3ccccc3-c3nccn32)C1] | 1-{3-[5-(4-bromophenyl)-5H-imidazo[2,1-a]isoindol-5-yl]propanoyl}piperidine-3-carboxamide | 493.1257 |

-continued

| STRUCTURE | Chemical name | Mass found |
|---|---|---|
| 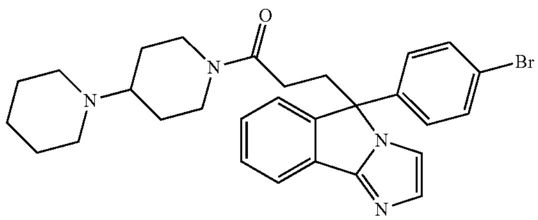 [SMILES: O=C(CCC1(c2ccc(Br)cc2)c2ccccc2-c2nccn21)N1CCC(N2CCCCC2)CC1] | 5-[3-(1,4'-bipiperidin-1'-yl)-3-oxopropyl]-5-(4-bromophenyl)-5H-imidazo[2,1-a]isoindole | 533.1912 |
| 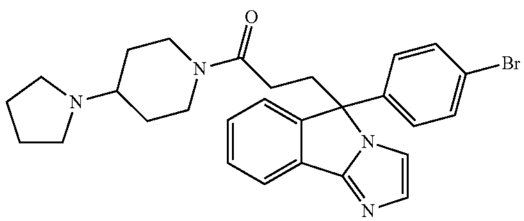 [SMILES: O=C(CCC1(c2ccc(Br)cc2)c2ccccc2-c2nccn21)N1CCC(N2CCCC2)CC1] | 5-(4-bromophenyl)-5-[3-oxo-3-(4-pyrrolidin-1-ylpiperidin-1-yl)propyl]-5H-imidazo[2,1-a]isoindole | 519.1758 |
| | 5-(4-bromophenyl)-5-{3-oxo-3-[3-(trifluoromethyl)piperidin-1-yl]propyl}-5H-imidazo[2,1-a]isoindole | 518.1065 |
| 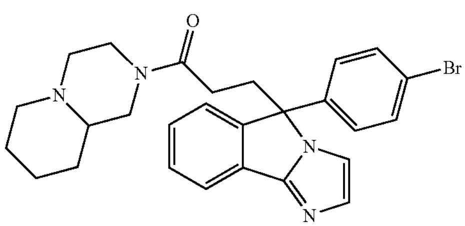 [SMILES: O=C(CCC1(c2ccc(Br)cc2)c2ccccc2-c2nccn21)N1CCN2CCCCC2C1] | 5-(4-bromophenyl)-5-[3-(octahydro-2H-pyrido[1,2-a]pyrazin-2-yl)-3-oxopropyl]-5H-imidazo[2,1-a]isoindole | 505.1574 |
| 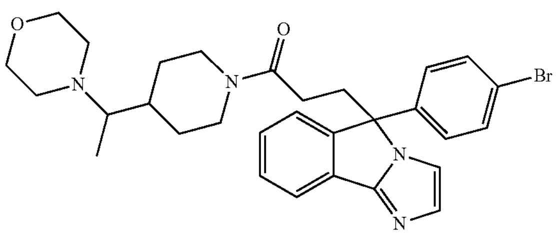 [SMILES: CC(C1CCN(C(=O)CCC2(c3ccc(Br)cc3)c3ccccc3-c3nccn32)CC1)N1CCOCC1] | 5-(4-bromophenyl)-5-{3-[4-(1-morpholin-4-ylethyl)piperidin-1-yl]-3-oxopropyl}-5H-imidazo[2,1-a]isoindole | 563.2006 |
| | 5-(4-bromophenyl)-5-{3-oxo-3-[2-(trifluoromethyl)piperidin-1-yl]propyl}-5H-imidazo[2,1-a]isoindole | 518.1067 |

| STRUCTURE | Chemical name | Mass found |
|---|---|---|
| 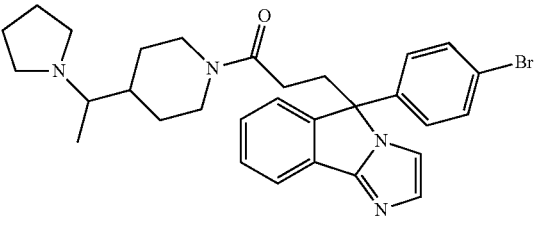 [SMILES: CC(C1CCN(C(=O)CCC2(c3ccc(Br)cc3)c3ccccc3-c3nccn32)CC1)N1CCCC1] | 5-(4-bromophenyl)-5-{3-oxo-3-[4-(1-pyrrolidin-1-ylethyl)piperidin-1-yl]propyl}-5H-imidazo[2,1-a]isoindole | 547.2068 |
| 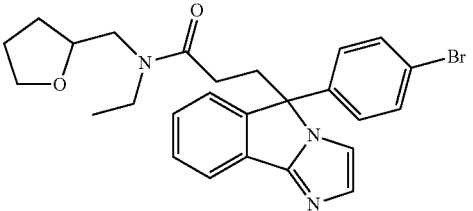 [SMILES: CCN(CC1CCCO1)C(=O)CCC1(c2ccc(Br)cc2)c2ccccc2-c2nccn21] | 3-[5-(4-bromophenyl)-5H-imidazo[2,1-a]isoindol-5-yl]-N-ethyl-N-(tetrahydrofuran-2-ylmethyl)propanamide | 494.1453 |
| 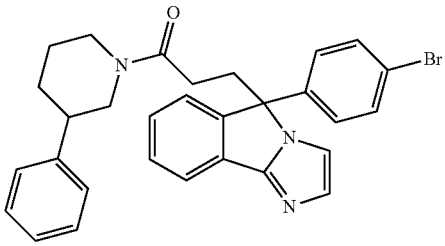 [SMILES: O=C(CCC1(c2ccc(Br)cc2)c2ccccc2-c2nccn21)N1CCCC(c2ccccc2)C1] | 5-(4-bromophenyl)-5-[3-oxo-3-(3-phenylpiperidin-1-yl)propyl]-5H-imidazo[2,1-a]isoindole | 526.1505 |
| 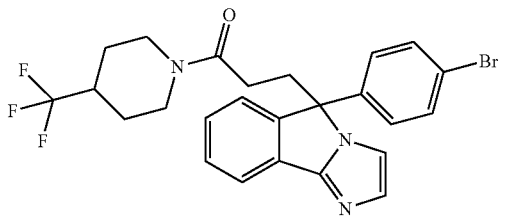 [SMILES: O=C(CCC1(c2ccc(Br)cc2)c2ccccc2-c2nccn21)N1CCC(C(F)(F)F)CC1] | 5-(4-bromophenyl)-5-{3-oxo-3-[4-(trifluoromethyl)piperidin-1-yl]propyl}-5H-imidazo[2,1-a]isoindole | 518.1067 |
| 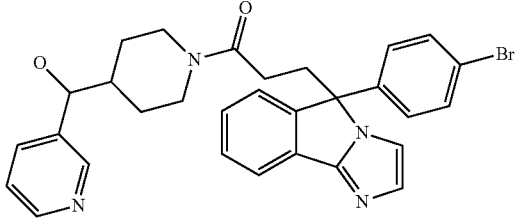 [SMILES: O=C(CCC1(c2ccc(Br)cc2)c2ccccc2-c2nccn21)N1CCC(C(O)c2cccnc2)CC1] | (1-{3-[5-(4-bromophenyl)-5H-imidazo[2,1-a]isoindol-5-yl]propanoyl}piperidin-4-yl)(pyridin-3-yl)methanol | 557.1541 |
| 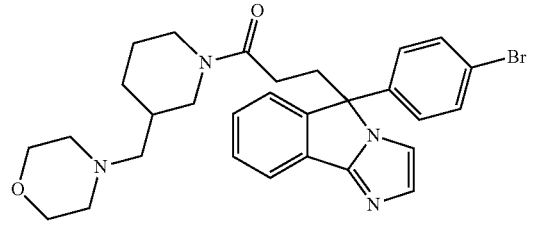 [SMILES: O=C(CCC1(c2ccc(Br)cc2)c2ccccc2-c2nccn21)N1CCCC(CN2CCOCC2)C1] | 5-(4-bromophenyl)-5-{3-[3-(morpholin-4-ylmethyl)piperidin-1-yl]-3-oxopropyl}-5H-imidazo[2,1-a]isoindole | 549.1864 |

-continued

| STRUCTURE | Chemical name | Mass found |
|---|---|---|
| 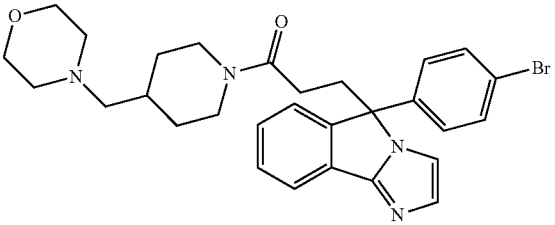 [SMILES: O=C(CCC1(c2ccc(Br)cc2)c2ccccc2-c2nccn21)N1CCC(CN2CCOCC2)CC1] | 5-(4-bromophenyl)-5-{3-[4-(morpholin-4-ylmethyl)piperidin-1-yl]-3-oxopropyl}-5H-imidazo[2,1-a]isoindole | 549.1857 |
| 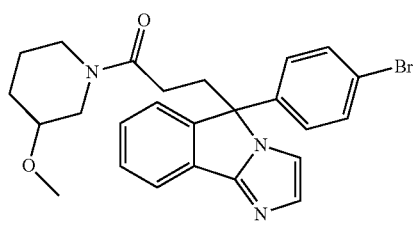 [SMILES: COC1CCCN(C(=O)CCC2(c3ccc(Br)cc3)c3ccccc3-c3nccn32)C1] | 5-(4-bromophenyl)-5-[3-(3-methoxypiperidin-1-yl)-3-oxopropyl]-5H-imidazo[2,1-a]isoindole | 480.1297 |
| 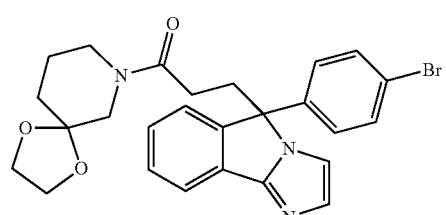 | 5-(4-bromophenyl)-5-[3-(1,4-dioxa-7-azaspiro[4.5]dec-7-yl)-3-oxopropyl]-5H-imidazo[2,1-a]isoindole | 508.124 |
| 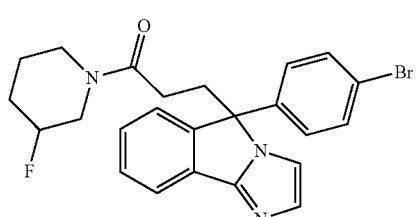 | 5-(4-bromophenyl)-5-[3-(3-fluoropiperidin-1-yl)-3-oxopropyl]-5H-imidazo[2,1-a]isoindole | 468.113 |
| 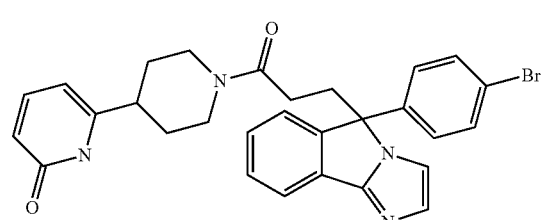 | 6-(1-{3-[5-(4-bromophenyl)-5H-imidazo[2,1-a]isoindol-5-yl]propanoyl}piperidin-4-yl)pyridin-2(1H)-one | 543.1393 |
| 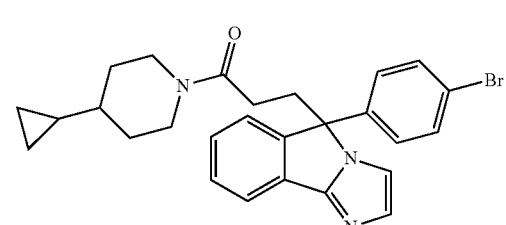 | 5-(4-bromophenyl)-5-[3-(4-cyclopropylpiperidin-1-yl)-3-oxopropyl]-5H-imidazo[2,1-a]isoindole | 490.1502 |
| 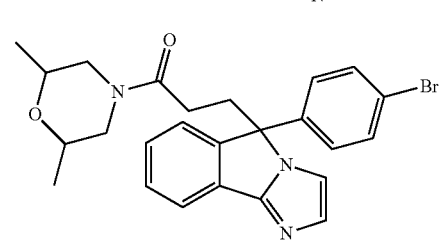 | 5-(4-bromophenyl)-5-[3-(2,6-dimethylmorpholin-4-yl)-3-oxopropyl]-5H-imidazo[2,1-a]isoindole | 480.1303 |

| STRUCTURE | Chemical name | Mass found |
|---|---|---|
| 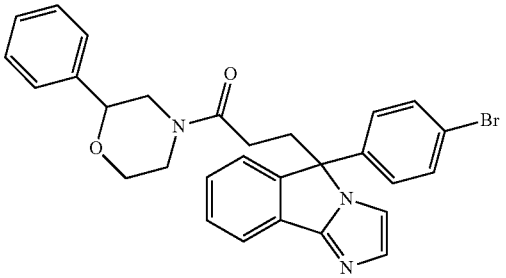 [SMILES: O=C(CCC1(c2ccc(Br)cc2)c2ccccc2-c2nccn21)N1CCOC(c2ccccc2)C1] | 5-(4-bromophenyl)-5-[3-oxo-3-(2-phenylmorpholin-4-yl)propyl]-5H-imidazo[2,1-a]isoindole | 528.1301 |
| 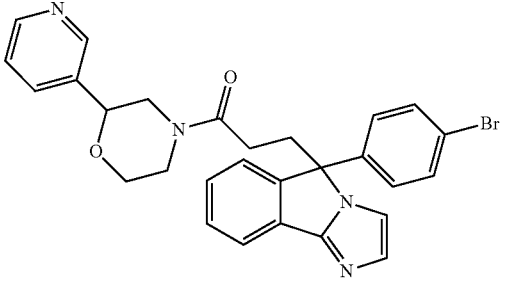 [SMILES: O=C(CCC1(c2ccc(Br)cc2)c2ccccc2-c2nccn21)N1CCOC(c2cccnc2)C1] | 5-(4-bromophenyl)-5-[3-oxo-3-(2-pyridin-3-ylmorpholin-4-yl)propyl]-5H-imidazo[2,1-a]isoindole | 529.1242 |
| 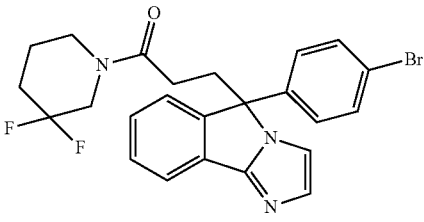 [SMILES: O=C(CCC1(c2ccc(Br)cc2)c2ccccc2-c2nccn21)N1CCCC(F)(F)C1] | 5-(4-bromophenyl)-5-[3-(3,3-difluoropiperidin-1-yl)-3-oxopropyl]-5H-imidazo[2,1-a]isoindole | 486.1003 |
| 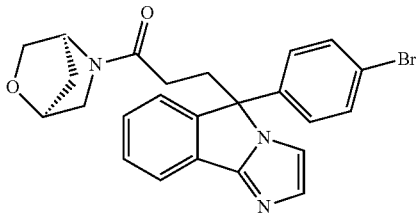 | 5-(4-bromophenyl)-5-{3-[(1S,4S)-2-oxa-5-azabicyclo[2.2.1]hept-5-yl]-3-oxopropyl}-5H-imidazo[2,1-a]isoindole | 464.0982 |
| 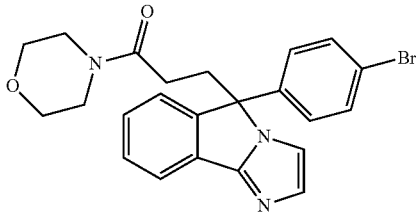 [SMILES: O=C(CCC1(c2ccc(Br)cc2)c2ccccc2-c2nccn21)N1CCOCC1] | 5-(4-bromophenyl)-5-(3-morpholin-4-yl-3-oxopropyl)-5H-imidazo[2,1-a]isoindole | 452.0988 |
| 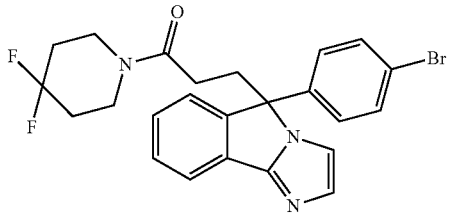 [SMILES: O=C(CCC1(c2ccc(Br)cc2)c2ccccc2-c2nccn21)N1CCC(F)(F)CC1] | 5-(4-bromophenyl)-5-[3-(4,4-difluoropiperidin-1-yl)-3-oxopropyl]-5H-imidazo[2,1-a]isoindole | 486.1005 |

| STRUCTURE | Chemical name | Mass found |
|---|---|---|
| 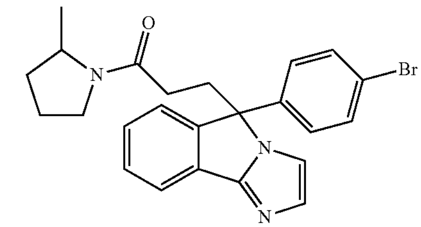 [SMILES: CC1CCCN1C(=O)CCC1(c2ccc(Br)cc2)c2ccccc2-c2nccn21] | 5-(4-bromophenyl)-5-[3-(2-methylpyrrolidin-1-yl)-3-oxopropyl]-5H-imidazo[2,1-a]isoindole | 450.1202 |
| 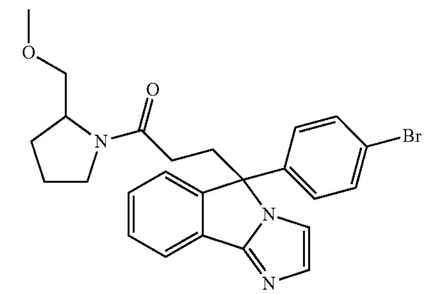 [SMILES: COCC1CCCN1C(=O)CCC1(c2ccc(Br)cc2)c2ccccc2-c2nccn21] | 5-(4-bromophenyl)-5-{3-[2-(methoxymethyl)pyrrolidin-1-yl]-3-oxopropyl}-5H-imidazo[2,1-a]isoindole | 480.1303 |
| | 5-(4-bromophenyl)-5-{3-oxo-3-[3-(trifluoromethyl)pyrrolidin-1-yl]propyl}-5H-imidazo[2,1-a]isoindole | 504.0923 |
| 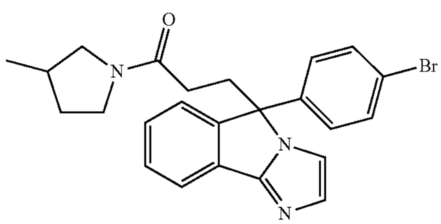 [SMILES: CC1CCN(C(=O)CCC2(c3ccc(Br)cc3)c3ccccc3-c3nccn32)C1] | 5-(4-bromophenyl)-5-[3-(3-methylpyrrolidin-1-yl)-3-oxopropyl]-5H-imidazo[2,1-a]isoindole | 450.1206 |
| 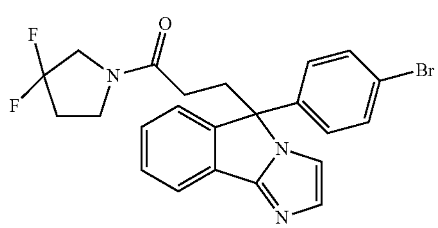 [SMILES: O=C(CCC1(c2ccc(Br)cc2)c2ccccc2-c2nccn21)N1CCC(F)(F)C1] | 5-(4-bromophenyl)-5-[3-(3,3-difluoropyrrolidin-1-yl)-3-oxopropyl]-5H-imidazo[2,1-a]isoindole | 472.084 |
| 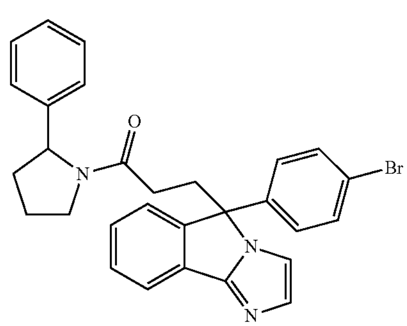 [SMILES: O=C(CCC1(c2ccc(Br)cc2)c2ccccc2-c2nccn21)N1CCCC1c1ccccc1] | 5-(4-bromophenyl)-5-[3-oxo-3-(2-phenylpyrrolidin-1-yl)propyl]-5H-imidazo[2,1-a]isoindole | 512.1338 |

| STRUCTURE | Chemical name | Mass found |
|---|---|---|
| 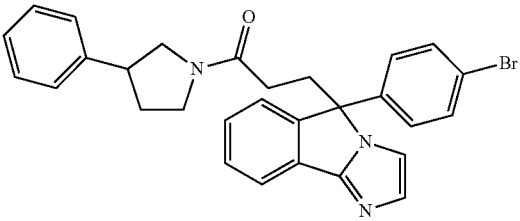 [SMILES: O=C(CCC1(c2ccc(Br)cc2)c2ccccc2-c2nccn21)N1CCC(c2ccccc2)C1] | 5-(4-bromophenyl)-5-[3-oxo-3-(3-phenylpyrrolidin-1-yl)propyl]-5H-imidazo[2,1-a]isoindole | 512.133 |
| 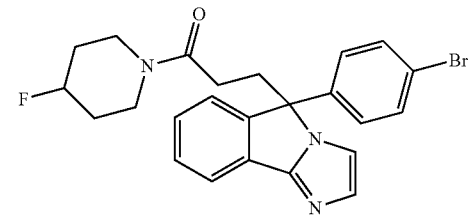 [SMILES: O=C(CCC1(c2ccc(Br)cc2)c2ccccc2-c2nccn21)N1CCC(F)CC1] | 5-(4-bromophenyl)-5-[3-(4-fluoropiperidin-1-yl)-3-oxopropyl]-5H-imidazo[2,1-a]isoindole | 468.1126 |
| 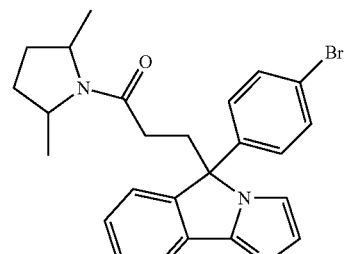 | 5-(4-bromophenyl)-5-[3-(2,5-dimethylpyrrolidin-1-yl)-3-oxopropyl]-5H-imidazo[2,1-a]isoindole | 464.1323 |
| 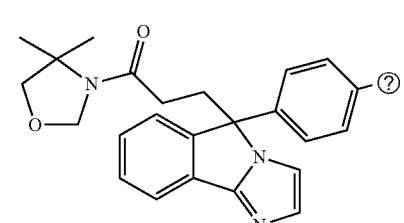 | 5-(4-bromophenyl)-5-[3-(4,4-dimethyl-1,3-oxazolidin-3-yl)-3-oxopropyl]-5H-imidazo[2,1-]isoindole | 466.1108 |
| 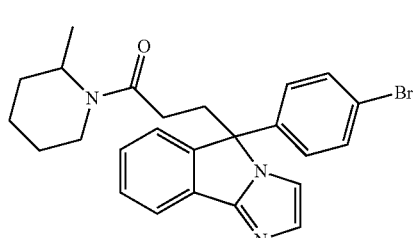 | 5-(4-bromophenyl)-5-[3-(2-methylpiperidin-1-yl)-3-oxopropyl]-5H-imidazo[2,1-a]isoindole | 464.1332 |
| 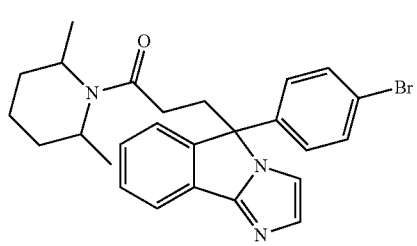 [SMILES: CC1CCCC(C)N1C(=O)CCC1(c2ccc(Br)cc2)c2ccccc2-c2nccn21] | 5-(4-bromophenyl)-5-[3-(2,6-dimethylpiperidin-1-yl)-3-oxopropyl]-5H-imidazo[2,1-a]isoindole | 478.1478 |

-continued

| STRUCTURE | Chemical name | Mass found |
|---|---|---|
| 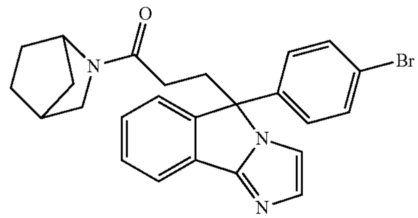 [SMILES: O=C(CCC1(c2ccc(Br)cc2)c2ccccc2-c2nccn21)N1CC2CCC1C2] | 5-[3-(2-azabicyclo[2.2.1]hept-2-yl)-3-oxopropyl]-5-(4-bromophenyl)-5H-imidazo[2,1-a]isoindole | 426.1162 |
| 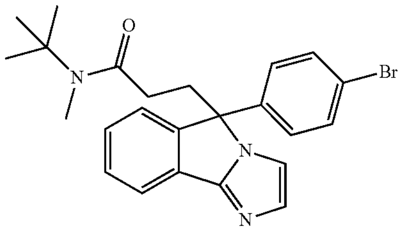 [SMILES: CN(C(=O)CCC1(c2ccc(Br)cc2)c2ccccc2-c2nccn21)C(C)(C)C] | 3-[5-(4-bromophenyl)-5H-imidazo[2,1-a]isoindol-5-yl]-N-tert-butyl-N-methylpropanamide | 452.1317 |
| 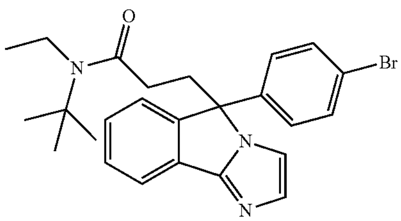 [SMILES: CCN(C(=O)CCC1(c2ccc(Br)cc2)c2ccccc2-c2nccn21)C(C)(C)C] | 3-[5-(4-bromophenyl)-5H-imidazo[2,1-a isoindol-5-yl]-N-tert-butyl-N-ethylpropanamide | 466.1472 |
| 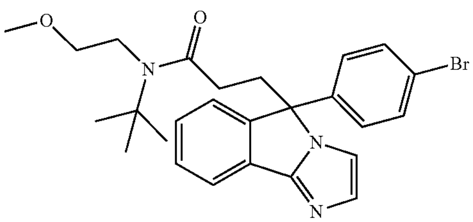 [SMILES: COCCN(C(=O)CCC1(c2ccc(Br)cc2)c2ccccc2-c2nccn21)C(C)(C)C] | 3-[5-(4-bromophenyl)-5H-imidazo[2,1-a]isoindol-5-yl]-N-tert-butyl-N-(2-methoxyethyl)propanamide | 496.1585 |
| 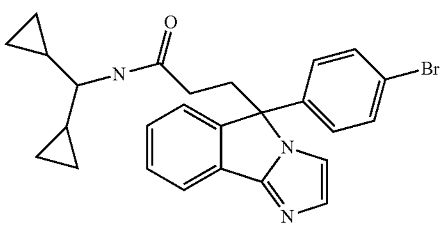 [SMILES: O=C(CCC1(c2ccc(Br)cc2)c2ccccc2-c2nccn21)NC(C1CC1)C1CC1] | 3-[5-(4-bromophenyl)-5H-imidazo[2,1-a]isoindol-5-yl]-N-(dicyclopropyl-methyl)propanamide | 476.1315 |
| 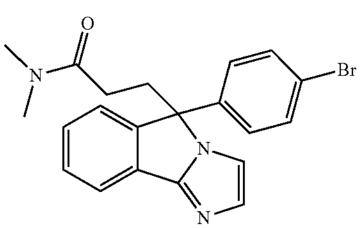 [SMILES: CN(C)C(=O)CCC1(c2ccc(Br)cc2)c2ccccc2-c2nccn21] | 3-[5-(4-bromophenyl)-5H-imidazo[2,1-a]isoindol-5-yl]-N,N-dimethylpropanamide | 410.0863 |
| 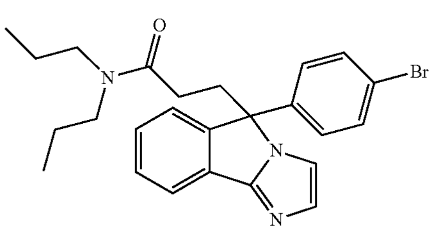 [SMILES: CCCN(CCC)C(=O)CCC1(c2ccc(Br)cc2)c2ccccc2-c2nccn21] | 3-[5-(4-bromophenyl)-5H-imidazo[2,1-a]isoindol-5-yl]-N,N-dipropylpropanamide | 466.1473 |

-continued

| STRUCTURE | Chemical name | Mass found |
|---|---|---|
| 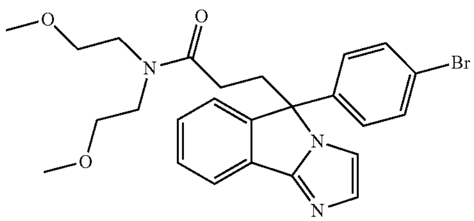 [SMILES: COCCN(CCOC)C(=O)CCC1(c2ccc(Br)cc2)c2ccccc2-c2nccn21] | 3-[5-(4-bromophenyl)-5H-imidazo[2,1-a]isoindol-5-yl]-N,N-bis(2-methoxyethyl)propanamide | 498.138 |
| 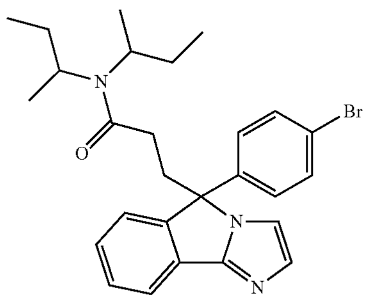 [SMILES: CCC(C)N(C(=O)CCC1(c2ccc(Br)cc2)c2ccccc2-c2nccn21)C(C)CC] | 3-[5-(4-bromophenyl)-5H-imidazo[2,1-a]isoindol-5-yl]-N,N-bis(1-methylpropyl)propanamide | 494.1788 |
| 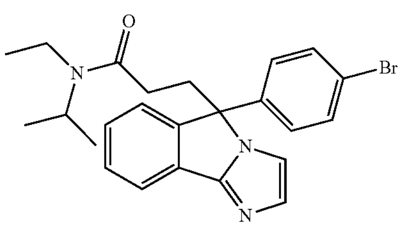 [SMILES: CCN(C(=O)CCC1(c2ccc(Br)cc2)c2ccccc2-c2nccn21)C(C)C] | 3-[5-(4-bromophenyl)-5H-imidazo[2,1-a]isoindol-5-yl]-N-ethyl-N-(1-methylethyl)propanamide | 452.1317 |
| 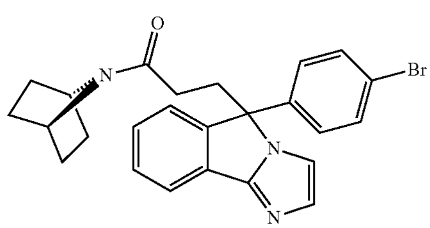 [SMILES: O=C(CCC1(c2ccc(Br)cc2)c2ccccc2-c2nccn21)N1[C@H]2CC[C@@H]1CC2] | 5-{3-[(1s,4s)-7-azabicyclo[2.2.1]hept-7-yl]-3-oxopropyl}-5-(4-bromophenyl)-5H-imidazo[2,1-a]isoindole | 462.1163 |
| 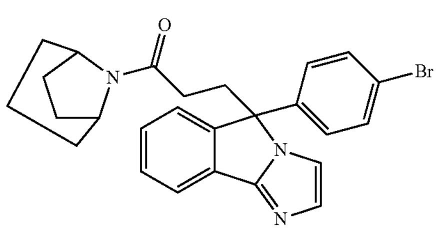 [SMILES: O=C(CCC1(c2ccc(Br)cc2)c2ccccc2-c2nccn21)N1C2CCCC1CC2] | 5-[3-(8-azabicyclo[3.2.1]oct-8-yl)-3-oxopropyl]-5-(4-bromophenyl)-5H-imidazo[2,1-a]isoindole | 476.1317 |
| 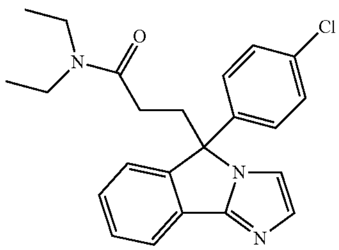 [SMILES: CCN(CC)C(=O)CCC1(c2ccc(Cl)cc2)c2ccccc2-c2nccn21] | 3-[5-(4-chlorophenyl)-5H-imidazo[2,1-a]isoindol-5-yl]-N,N-diethylpropanamide | 394.1682 |

| STRUCTURE | Chemical name | Mass found |
|---|---|---|
| 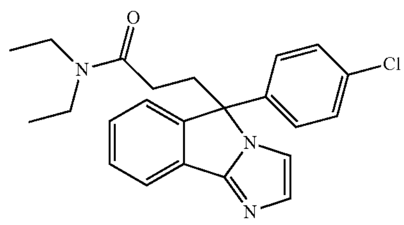 [SMILES: CCN(CC)C(=O)CCC1(c2ccc(Cl)cc2)c2ccccc2-c2nccn21] | 3-[5-(4-chlorophenyl)-5H-imidazo[2,1-a]isoindol-5-yl]-N,N-diethylpropanamide | 394.169 |
| 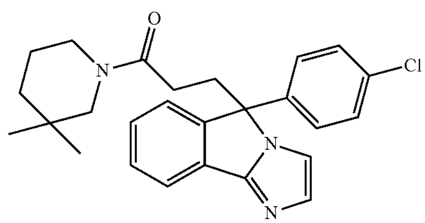 [SMILES: CC1(C)CCCN(C(=O)CCC2(c3ccc(Cl)cc3)c3ccccc3-c3nccn32)C1] | 5-(4-chlorophenyl)-5-[3-(3,3-dimethylpiperidin-1-yl)-3-oxopropyl]-5H-imidazo[2,1-a]isoindole | 434.1994 |
| 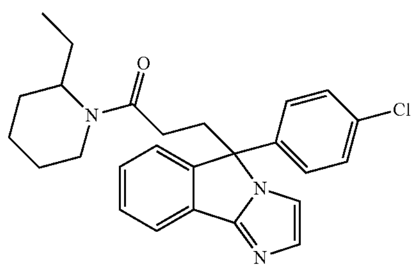 [SMILES: CCC1CCCCN1C(=O)CCC1(c2ccc(Cl)cc2)c2ccccc2-c2nccn21] | 5-(4-chlorophenyl)-5-[3-(2-ethylpiperidin-1-yl)-3-oxopropyl]-5H-imidazo[2,1-a]isoindole | 434.1995 |
| 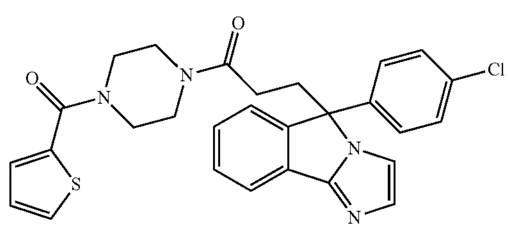 [SMILES: O=C(CCC1(c2ccc(Cl)cc2)c2ccccc2-c2nccn21)N1CCN(C(=O)c2cccs2)CC1] | 5-(4-chlorophenyl)-5-{3-oxo-3-[4-(thiophen-2-ylcarbonyl)piperazin-1-yl]propyl}-5H-imidazo[2,1-a]isoindole | 517.1456 |
| 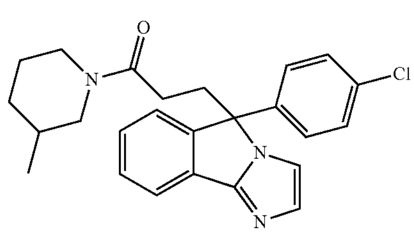 [SMILES: CC1CCCN(C(=O)CCC2(c3ccc(Cl)cc3)c3ccccc3-c3nccn32)C1] | 5-(4-chlorophenyl)-5-[3-(3-methylpiperidin-1-yl)-3-oxopropyl]-5H-imidazo[2,1-a]isoindole | 420.1844 |
| 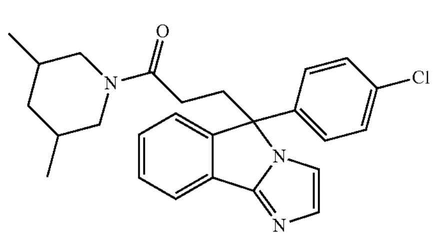 [SMILES: CC1CC(C)CN(C(=O)CCC2(c3ccc(Cl)cc3)c3ccccc3-c3nccn32)C1] | 5-(4-chlorophenyl)-5-[3-(3,5-dimethylpiperidin-1-yl)-3-oxopropyl]-5H-imidazo[2,1-a]isoindole | 434.2002 |

| STRUCTURE | Chemical name | Mass found |
|---|---|---|
| 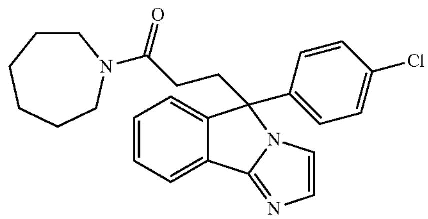 [SMILES: O=C(CCC1(c2ccc(Cl)cc2)c2ccccc2-c2nccn21)N1CCCCCC1] | 5-(3-azepan-1-yl-3-oxopropyl)-5-(4-chlorophenyl)-5H-imidazo[2,1-a]isoindole | 420.1844 |
| 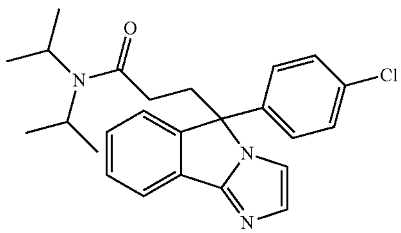 [SMILES: CC(C)N(C(=O)CCC1(c2ccc(Cl)cc2)c2ccccc2-c2nccn21)C(C)C] | 3-[5-(4-chlorophenyl)-5H-imidazo[2,1-a]isoindol-5-yl]-N,N-bis(1-methylethyl)propanamide | 422.2002 |
| 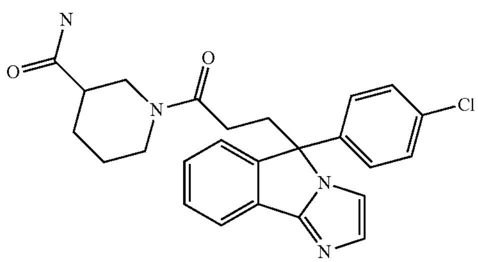 [SMILES: NC(=O)C1CCCN(C(=O)CCC2(c3ccc(Cl)cc3)c3ccccc3-c3nccn32)C1] | 1-{3-[5-(4-chlorophenyl)-5H-imidazo[2,1-a]isoindol-5-yl]propanoyl}piperidine-3-carboxamide | 449.1736 |
|  | 5-(4-chlorophenyl)-5-{3-oxo-3-[3-(trifluoromethyl)piperidin-1-yl]propyl}-5H-imidazo[2,1-a]isoindole | 474.1571 |
|  | 5-(4-chlorophenyl)-5-{3-oxo-3-[2-(trifluoromethyl)piperidin-1-yl]propyl}-5H-imidazo[2,1-a]isoindole | 474.1568 |
| 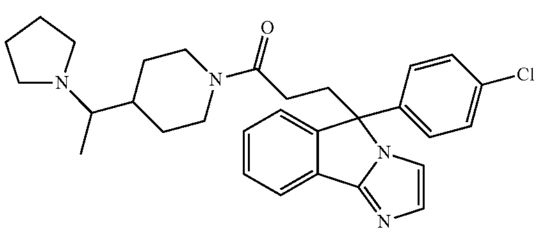 [SMILES: CC(C1CCN(C(=O)CCC2(c3ccc(Cl)cc3)c3ccccc3-c3nccn32)CC1)N1CCCC1] | 5-(4-chlorophenyl)-5-{3-oxo-3-[4-(1-pyrrolidin-1-ylethyl)piperidin-1-yl]propyl}-5H-imidazo[2,1-a]isoindole | 503.2569 |

-continued

| STRUCTURE | Chemical name | Mass found |
|---|---|---|
| 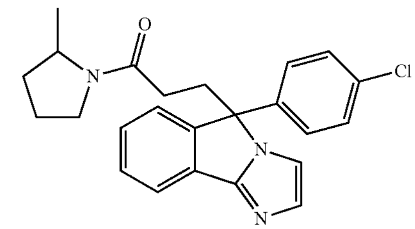 [SMILES: CC1CCCN1C(=O)CCC1(c2ccc(Cl)cc2)c2ccccc2-c2nccn21] | 5-(4-chlorophenyl)-5-[3-(2-methylpyrrolidin-1-yl)-3-oxopropyl]-5H-imidazo[2,1-a]isoindole | 406.1692 |
| 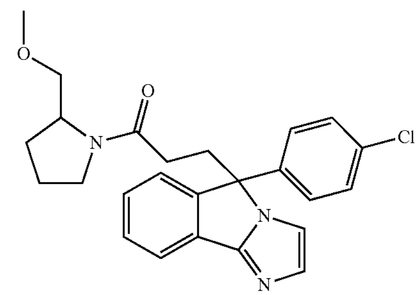 [SMILES: COCC1CCCN1C(=O)CCC1(c2ccc(Cl)cc2)c2ccccc2-c2nccn21] | 5-(4-chlorophenyl)-5-{3-[2-(methoxymethyl)pyrrolidin-1-yl]-3-oxopropyl}-5H-imidazo[2,1-a]isoindole | 436.18 |
| 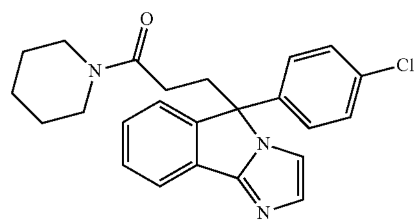 [SMILES: O=C(CCC1(c2ccc(Cl)cc2)c2ccccc2-c2nccn21)N1CCCCC1] | 5-(4-chlorophenyl)-5-(3-oxo-3-piperidin-1-ylpropyl)-5H-imidazo[2,1-a]isoindole | 406.1692 |
| 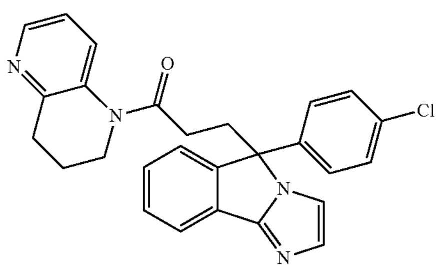 [SMILES: O=C(CCC1(c2ccc(Cl)cc2)c2ccccc2-c2nccn21)N1CCCc2ncccc21] | 5-(4-chlorophenyl)-5-[3-(3,4-dihydro-1,5-naphthyridin-1(2H)-yl)-3-oxopropyl]-5H-imidazo[2,1-a]isoindole | 455.164 |
| 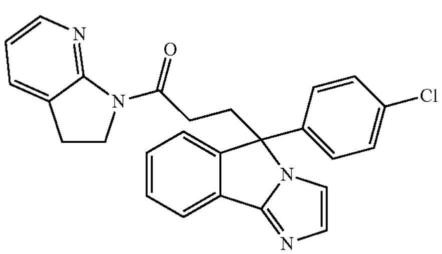 [SMILES: O=C(CCC1(c2ccc(Cl)cc2)c2ccccc2-c2nccn21)N1CCc2cccnc21] | 5-(4-chlorophenyl)-5-[3-(2,3-dihydro-1H-pyrrolo[2,3-b]pyridin-1-yl)-3-oxopropyl]-5H-imidazo[2,1-a]isoindole | 441.1486 |
| 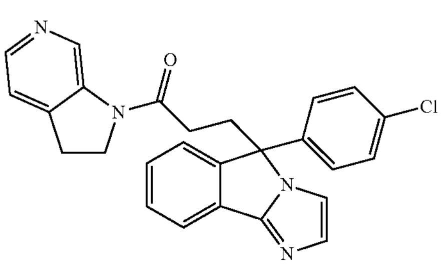 [SMILES: O=C(CCC1(c2ccc(Cl)cc2)c2ccccc2-c2nccn21)N1CCc2ccncc21] | 5-(4-chlorophenyl)-5-[3-(2,3-dihydro-1H-pyrrolo[2,3-c]pyridin-1-yl)-3-oxopropyl]-5H-imidazo[2,1-a]isoindole | 441.1487 |

-continued

| STRUCTURE | Chemical name | Mass found |
|---|---|---|
| 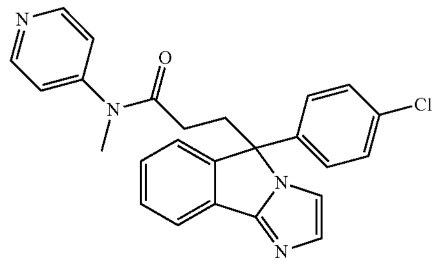 [SMILES: CN(C(=O)CCC1(c2ccc(Cl)cc2)c2ccccc2-c2nccn21)c1ccncc1] | 3-[5-(4-chlorophenyl)-5H-imidazo[2,1-a]isoindol-5-yl]-N-methyl-N-pyridin-4-ylpropanamide | 429.1484 |
| 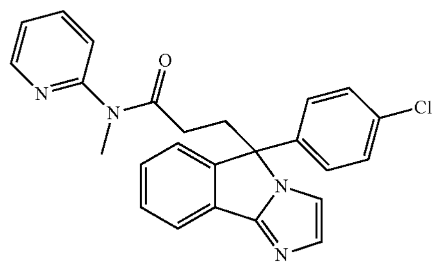 [SMILES: CN(C(=O)CCC1(c2ccc(Cl)cc2)c2ccccc2-c2nccn21)c1ccccn1] | 3-[5-(4-chlorophenyl)-5H-imidazo[2,1-a]isoindol-5-yl]-N-methyl-N-pyridin-2-ylpropanamide | 429.1484 |
| 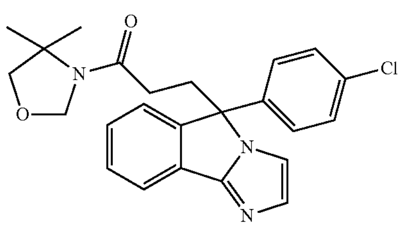 [SMILES: CC1(C)COCN1C(=O)CCC1(c2ccc(Cl)cc2)c2ccccc2-c2nccn21] | 5-(4-chlorophenyl)-5-[3-(4,4-dimethyl-1,3-oxazolidin-3-yl)-3-oxopropyl]-5H-imidazo[2,1-a]isoindole | 422.1641 |
| 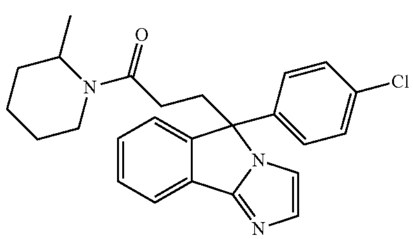 [SMILES: CC1CCCCN1C(=O)CCC1(c2ccc(Cl)cc2)c2ccccc2-c2nccn21] | 5-(4-chlorophenyl)-5-[3-(2-methylpiperidin-1-yl)-3-oxopropyl]-5H-imidazo[2,1-a]isoindole | 420.1848 |
| 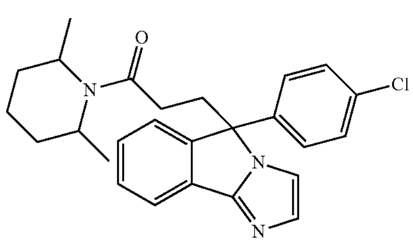 [SMILES: CC1CCCC(C)N1C(=O)CCC1(c2ccc(Cl)cc2)c2ccccc2-c2nccn21] | 5-(4-chlorophenyl)-5-[3-(2,6-dimethylpiperidin-1-yl)-3-oxopropyl]-5H-imidazo[2,1-a]isoindole | 434.2005 |
| 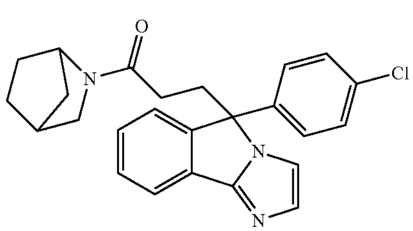 [SMILES: O=C(CCC1(c2ccc(Cl)cc2)c2ccccc2-c2nccn21)N1CC2CCC1C2] | 5-[3-(2-azabicyclo[2.2.1]hept-2-yl)-3-oxopropyl]-5-(4-chlorophenyl)-5H-imidazo[2,1-a]isoindole | 418.1692 |

| STRUCTURE | Chemical name | Mass found |
|---|---|---|
| 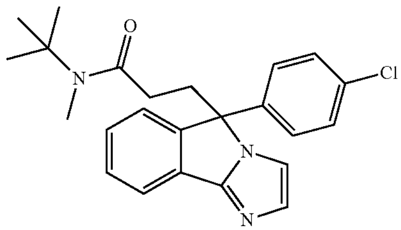 [SMILES: CN(C(=O)CCC1(c2ccc(Cl)cc2)c2ccccc2-c2nccn21)C(C)(C)C] | N-tert-butyl-3-[5-(4-chlorophenyl)-5H-imidazo[2,1-a]isoindol-5-yl]-N-methylpropanamide | 408.1847 |
| 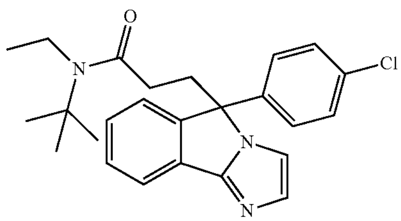 [SMILES: CCN(C(=O)CCC1(c2ccc(Cl)cc2)c2ccccc2-c2nccn21)C(C)(C)C] | N-tert-butyl-3-[5-(4-chlorophenyl)-5H-imidazo[2,1-a]isoindol-5-yl]-N-ethylpropanamide | 422.2003 |
| 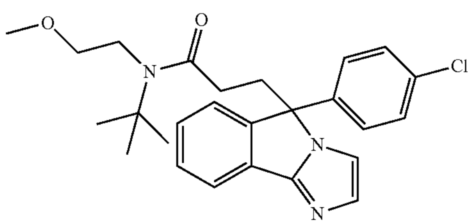 [SMILES: COCCN(C(=O)CCC1(c2ccc(Cl)cc2)c2ccccc2-c2nccn21)C(C)(C)C] | N-tert-butyl-3-[5-(4-chlorophenyl)-5H-imidazo[2,1-a]isoindol-5-yl]-N-(2-methoxyethyl)propanamide | 452.2108 |
| 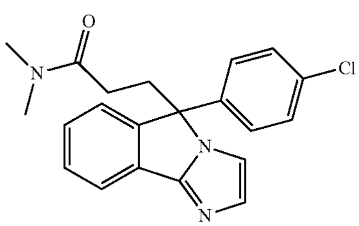 [SMILES: CN(C)C(=O)CCC1(c2ccc(Cl)cc2)c2ccccc2-c2nccn21] | 3-[5-(4-chlorophenyl)-5H-imidazo[2,1-a]isoindol-5-yl]-N,N-dimethylpropanamide | 366.1374 |
| 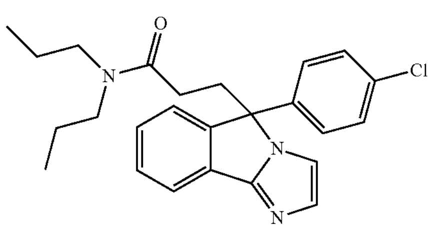 [SMILES: CCCN(CCC)C(=O)CCC1(c2ccc(Cl)cc2)c2ccccc2-c2nccn21] | 3-[5-(4-chlorophenyl)-5H-imidazo[2,1-a]isoindol-5-yl]-N,N-dipropylpropanamide | 422.2006 |
| 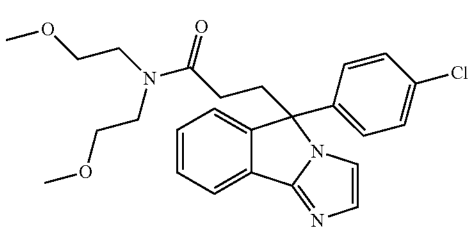 [SMILES: COCCN(CCOC)C(=O)CCC1(c2ccc(Cl)cc2)c2ccccc2-c2nccn21] | 3-[5-(4-chlorophenyl)-5H-imidazo[2,1-a]isoindol-5-yl]-N,N-bis(2-methoxyethyl)propanamide | 454.1901 |

| STRUCTURE | Chemical name | Mass found |
|---|---|---|
| 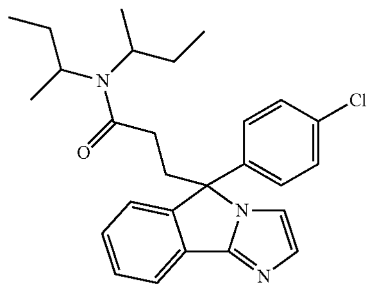 [SMILES: CCC(C)N(C(=O)CCC1(c2ccc(Cl)cc2)c2ccccc2-c2nccn21)C(C)CC] | 3-[5-(4-chlorophenyl)-5H-imidazo[2,1-a]isoindol-5-yl]-N,N-bis(1-methylpropyl)propanamide | 450.2322 |
| 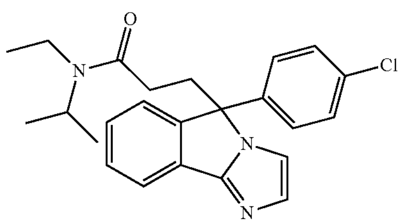 [SMILES: CCN(C(=O)CCC1(c2ccc(Cl)cc2)c2ccccc2-c2nccn21)C(C)C] | 3-[5-(4-chlorophenyl)-5H-imidazo[2,1-a]isoindol-5-yl]-N-ethyl-N-(1-methylethyl)propanamide | 408.1847 |
| 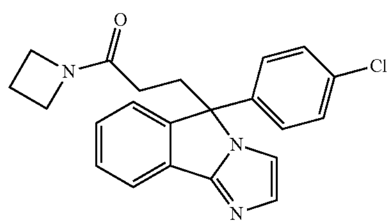 [SMILES: O=C(CCC1(c2ccc(Cl)cc2)c2ccccc2-c2nccn21)N1CCC1] | 5-(3-azetidin-1-yl-3-oxopropyl)-5-(4-chlorophenyl-5H-imidazo[2,1-a]isoindole | 378.1369 |
| 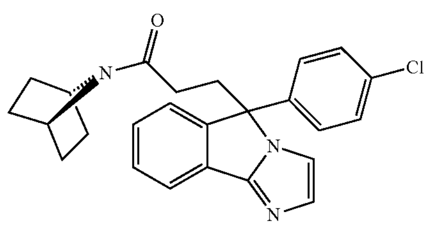 [SMILES: O=C(CCC1(c2ccc(Cl)cc2)c2ccccc2-c2nccn21)N1[C@H]2CC[C@@H]1CC2] | 5-{3-[(1s,4s)-7-azabicyclo[2.2.1]hept-7-yl]-3-oxopropyl}-5-(4-chlorophenyl)-5H-imidazo[2,1-a]isoindole | 418.1691 |
| 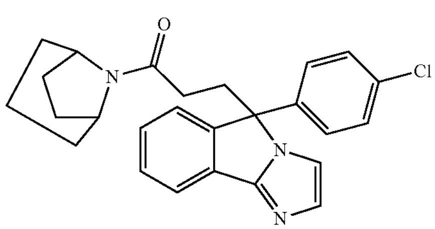 [SMILES: O=C(CCC1(c2ccc(Cl)cc2)c2ccccc2-c2nccn21)N1C2CCCC1CC2] | 5-[3-(8-azabicyclo[3.2.1]oct-8-yl)-3-oxopropyl]-5-(4-chlorophenyl)-5H-imidazo[2,1-a]isoindole | 432.1845 |
| 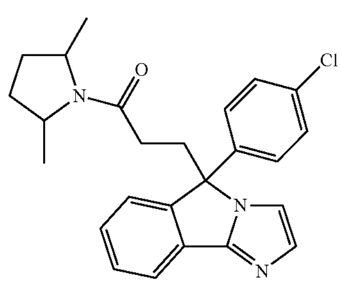 [SMILES: CC1CCC(C)N1C(=O)CCC1(c2ccc(Cl)cc2)c2ccccc2-c2nccn21] | 5-(4-chlorophenyl)-5-[3-(2,5-dimethylpyrrolidin-1-yl)-3-oxopropyl]-5H-imidazo[2,1-a]isoindole | 420.1841 |

-continued

| STRUCTURE | Chemical name | Mass found |
|---|---|---|
| 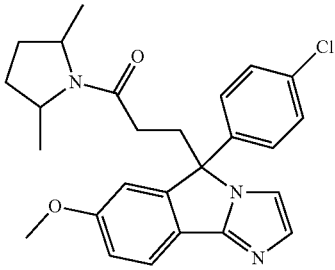 [SMILES: COc1ccc2c(c1)C(CCC(=O)N1C(C)CCC1C)(c1ccc(Cl)cc1)n1ccnc1-2] | 5-(4-chlorophenyl)-5-[3-(2,5-dimethylpyrrolidin-1-yl)-3-oxopropyl]-7-methoxy-5H-imidazo[2,1-a]isoindole | 450.1933 |
| 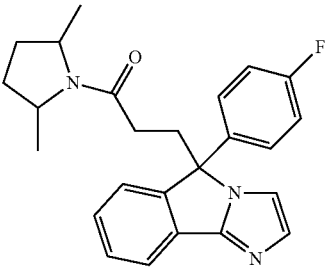 [SMILES: CC1CCC(C)N1C(=O)CCC1(c2ccc(F)cc2)c2ccccc2-c2nccn21] | 5-[3-(2,5-dimethylpyrrolidin-1-yl)-3-oxopropyl]-5-(4-fluorophenyl)-5H-imidazo[2,1-a]isoindole | 404.2135 |
| 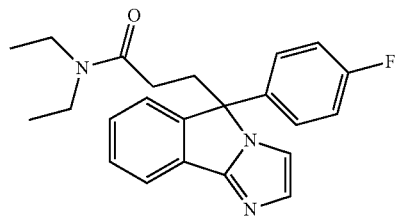 [SMILES: CCN(CC)C(=O)CCC1(c2ccc(F)cc2)c2ccccc2-c2nccn21] | N,N-diethyl-3-[5-(4-fluorophenyl)-5H-imidazo[2,1-a]isoindol-5-yl]propanamide | 378.1963 |
| 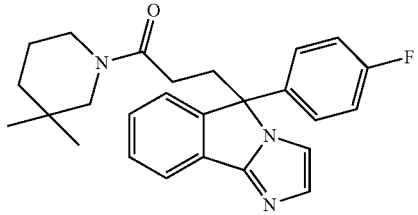 [SMILES: CC1(C)CCCN(C(=O)CCC2(c3ccc(F)cc3)c3ccccc3-c3nccn32)C1] | 5-[3-(3,3-dimethylpiperidin-1-yl)-3-oxopropyl]-5-(4-fluorophenyl)-5H-imidazo[2,1-a]isoindole | 418.2289 |
| 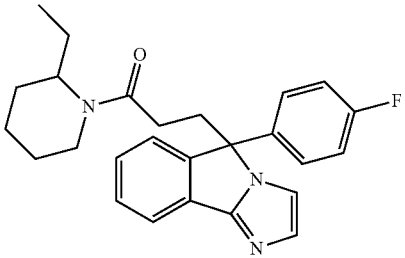 [SMILES: CCC1CCCCN1C(=O)CCC1(c2ccc(F)cc2)c2ccccc2-c2nccn21] | 5-[3-(2-ethylpiperidin-1-yl)-3-oxopropyl]-5-(4-fluorophenyl)-5H-imidazo[2,1-a]isoindole | 418.2274 |
| 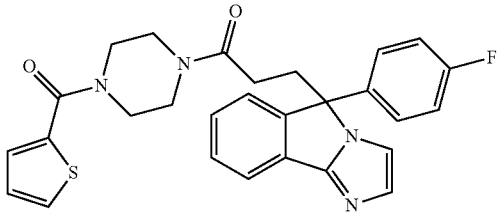 [SMILES: O=C(CCC1(c2ccc(F)cc2)c2ccccc2-c2nccn21)N1CCN(C(=O)c2cccs2)CC1] | 5-(4-fluorophenyl)-5-{3-oxo-3-[4-(thiophen-2-ylcarbonyl)piperazin-1-yl]propyl}-5H-imidazo[2,1-a]isoindole | 501.1755 |

-continued

| STRUCTURE | Chemical name | Mass found |
|---|---|---|
| 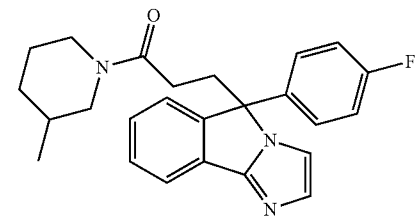 [SMILES: CC1CCCN(C(=O)CCC2(c3ccc(F)cc3)c3ccccc3-c3nccn32)C1] | 5-(4-fluorophenyl)-5-[3-(3-methylpiperidin-1-yl)-3-oxopropyl]-5H-imidazo[2,1-a]isoindole | 404.2119 |
| 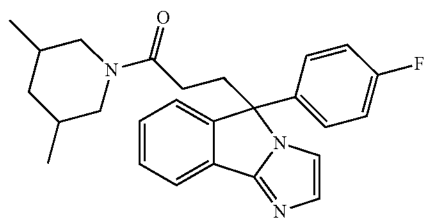 [SMILES: CC1CC(C)CN(C(=O)CCC2(c3ccc(F)cc3)c3ccccc3-c3nccn32)C1] | 5-[3-(3,5-dimethylpiperidin-1-yl)-3-oxopropyl]-5-(4-fluorophenyl)-5H-imidazo[2,1-a]isoindole | 418.2275 |
| 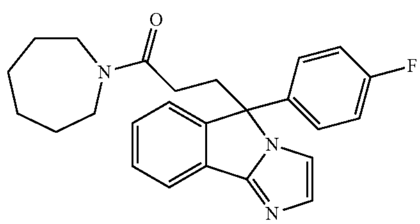 [SMILES: O=C(CCC1(c2ccc(F)cc2)c2ccccc2-c2nccn21)N1CCCCCC1] | 5-(3-azepan-1-yl-3-oxopropyl)-5-(4-fluorophenyl)-5H-imidazo[2,1-a]isoindole | 404.212 |
| 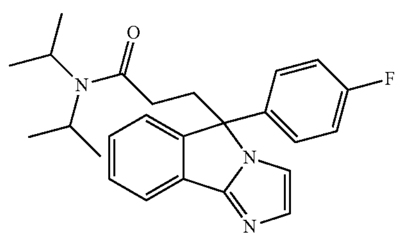 [SMILES: CC(C)N(C(=O)CCC1(c2ccc(F)cc2)c2ccccc2-c2nccn21)C(C)C] | 3-[5-(4-fluorophenyl)-5H-imidazo[2,1-a]isoindol-5-yl]-N,N-bis(1-methylethyl)propanamide | 406.2273 |
| 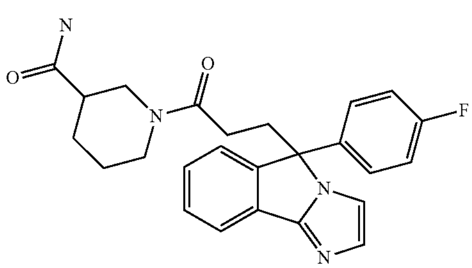 [SMILES: NC(=O)C1CCCN(C(=O)CCC2(c3ccc(F)cc3)c3ccccc3-c3nccn32)C1] | 1-{3-[5-(4-fluorophenyl)-5H-imidazo[2,1-a]isoindol-5-yl]propanoyl}piperidine-3-carboxamide | 433.2019 |
| 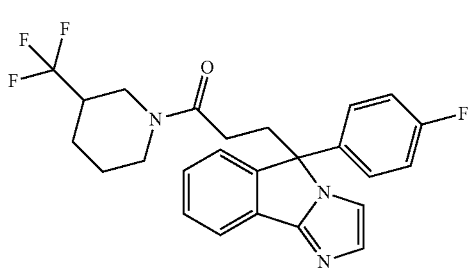 [SMILES: O=C(CCC1(c2ccc(F)cc2)c2ccccc2-c2nccn21)N1CCCC(C(F)(F)F)C1] | 5-(4-fluorophenyl)-5-{3-oxo-3-[3-(trifluoromethyl)piperidin-1-yl]propyl}-5H-imidazo[2,1-a]isoindole | 458.183 |

| STRUCTURE | Chemical name | Mass found |
|---|---|---|
| 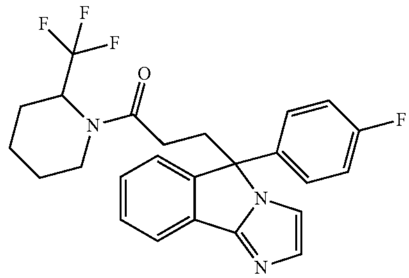 [SMILES: O=C(CCC1(c2ccc(F)cc2)c2ccccc2-c2nccn21)N1CCCCC1C(F)(F)F] | 5-(4-fluorophenyl)-5-{3-oxo-3-[2-(trifluoromethyl)piperidin-1-yl]propyl}-5H-imidazo[2,1-a]isoindole | 458.1832 |
| 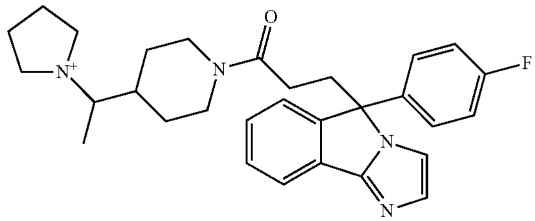 [SMILES: CC(C1CCN(C(=O)CCC2(c3ccc(F)cc3)c3ccccc3-c3nccn32)CC1)[NH+]1CCCC1] | 5-(4-fluorophenyl)-5-{3-oxo-3-[4-(1-pyrrolidin-1-ylethyl)piperidin-1-yl]propyl}-5H-imidazo[2,1-a]isoindole | 487.2854 |
| 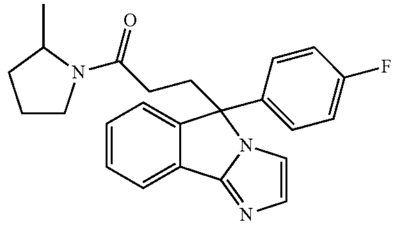 [SMILES: CC1CCCN1C(=O)CCC1(c2ccc(F)cc2)c2ccccc2-c2nccn21] | 5-(4-fluorophenyl)-5-[3-(2-methylpyrrolidin-1-yl)-3-oxopropyl]-5H-imidazo[2,1-a]isoindole | 390.1976 |
| 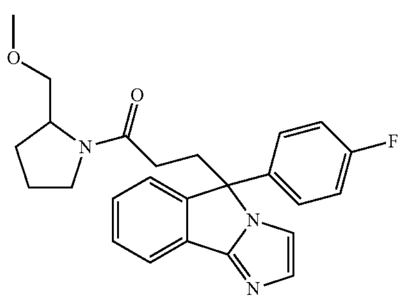 [SMILES: COCC1CCCN1C(=O)CCC1(c2ccc(F)cc2)c2ccccc2-c2nccn21] | 5-(4-fluorophenyl)-5-{3-[2-(methoxymethyl)pyrrolidin-1-yl]-3-oxopropyl}-5H-imidazo[2,1-a]isoindole | 420.2067 |
| 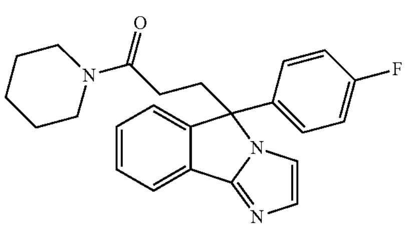 [SMILES: O=C(CCC1(c2ccc(F)cc2)c2ccccc2-c2nccn21)N1CCCCC1] | 5-(4-fluorophenyl)-5-(3-oxo-3-piperidin-1-ylpropyl)-5H-imidazo[2,1-a]isoindole | 390.1963 |
| 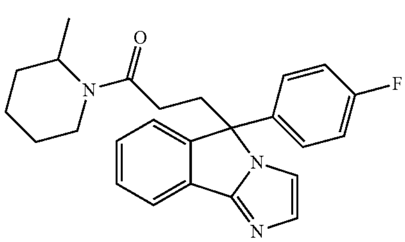 [SMILES: CC1CCCCN1C(=O)CCC1(c2ccc(F)cc2)c2ccccc2-c2nccn21] | 5-(4-fluorophenyl)-5-[3-(2-methylpiperidin-1-yl)-3-oxopropyl]-5H-imidazo[2,1-a]isoindole | 404.2117 |

| STRUCTURE | Chemical name | Mass found |
|---|---|---|
| 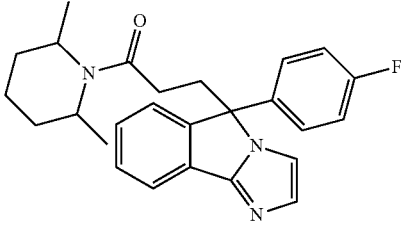 [SMILES: CC1CCCC(C)N1C(=O)CCC1(c2ccc(F)cc2)c2ccccc2-c2nccn21] | 5-[3-(2,6-dimethylpiperidin-1-yl)-3-oxopropyl]-5-(4-fluorophenyl)-5H-imidazo[2,1-a]isoindole | 418.2276 |
| 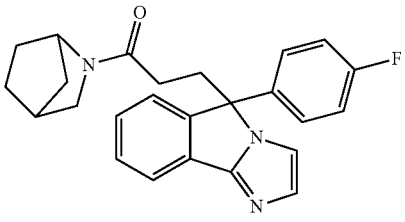 [SMILES: O=C(CCC1(c2ccc(F)cc2)c2ccccc2-c2nccn21)N1CC2CCC1C2] | 5-[3-(2-azabicyclo[2.2.1]hept-2-yl)-3-oxopropyl]-5-(4-fluorophenyl)-5H-imidazo[2,1-a]isoindole | 402.1961 |
| 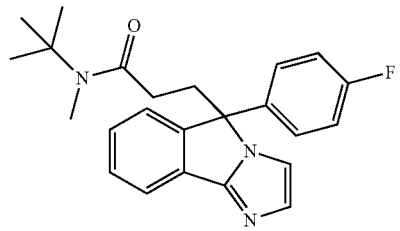 [SMILES: CN(C(=O)CCC1(c2ccc(F)cc2)c2ccccc2-c2nccn21)C(C)(C)C] | N-tert-butyl-3-[5-(4-fluorophenyl)-5H-imidazo[2,1-a]isoindol-5-yl]-N-methylpropanamide | 392.2117 |
| 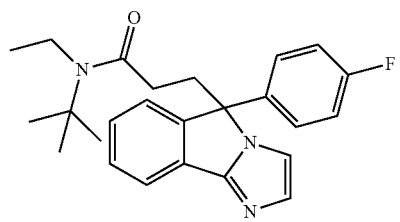 [SMILES: CCN(C(=O)CCC1(c2ccc(F)cc2)c2ccccc2-c2nccn21)C(C)(C)C] | N-tert-butyl-N-ethyl-3-[5-(4-fluorophenyl)-5H-imidazo[2,1-a]isoindol-5-yl]propanamide | 406.2273 |
| 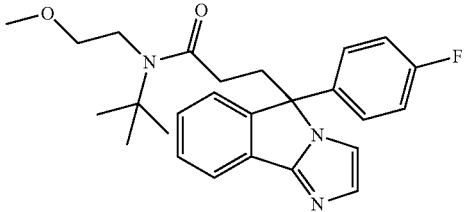 [SMILES: COCCN(C(=O)CCC1(c2ccc(F)cc2)c2ccccc2-c2nccn21)C(C)(C)C] | N-tert-butyl-3-[5-(4-fluorophenyl)-5H-imidazo[2,1-a]isoindol-5-yl]-N-(2-methoxyethyl)propanamide | 436.2377 |
| 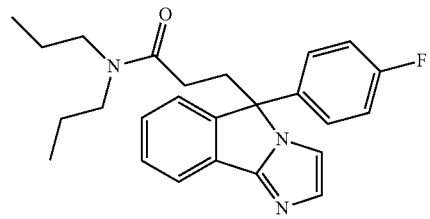 [SMILES: CCCN(CCC)C(=O)CCC1(c2ccc(F)cc2)c2ccccc2-c2nccn21] | 3-[5-(4-fluorophenyl)-5H-imidazo[2,1-a]isoindol-5-yl]-N,N-dipropylpropanamide | 406.2273 |

-continued

| STRUCTURE | Chemical name | Mass found |
|---|---|---|
| 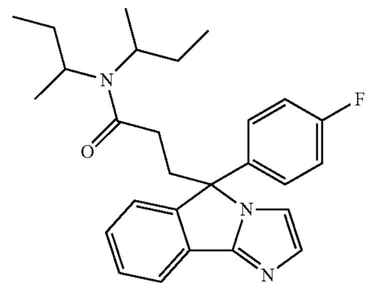 [SMILES: CCC(C)N(C(=O)CCC1(c2ccc(F)cc2)c2ccccc2-c2nccn21)C(C)CC] | 3-[5-(4-fluorophenyl)-5H-imidazo[2,1-a]isoindol-5-yl]-N,N-bis(1-methylpropyl)propanamide | 434.2586 |
| 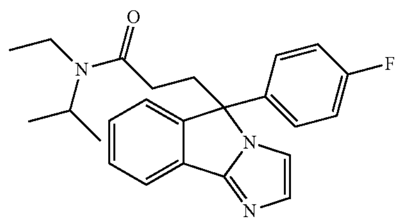 [SMILES: CCN(C(=O)CCC1(c2ccc(F)cc2)c2ccccc2-c2nccn21)C(C)C] | N-ethyl-3-[5-(4-fluorophenyl)-5H-imidazo[2,1-a]isoindol-5-yl]-N-(1-methylethyl)propanamide | 392.2118 |
| 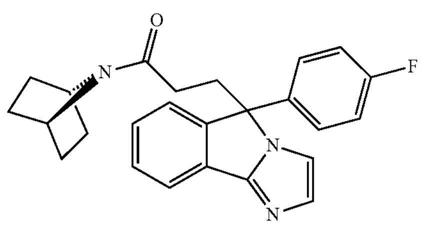 [SMILES: O=C(CCC1(c2ccc(F)cc2)c2ccccc2-c2nccn21)N1[C@H]2CC[C@@H]1CC2] | 5-{3-[(1s,4s)-7-azabicyclo[2.2.1]hept-7-yl]-3-oxopropyl}-5-(4-fluorophenyl)-5H-imidazo[2,1-a]isoindole | 402.196 |
| 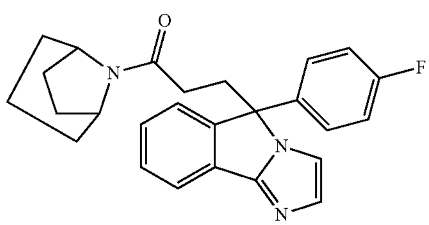 [SMILES: O=C(CCC1(c2ccc(F)cc2)c2ccccc2-c2nccn21)N1C2CCCC1CC2] | 5-[3-(8-azabicyclo[3.2.1]oct-8-yl)-3-oxopropyl]-5-(4-fluorophenyl)-5H-imidazo[2,1-a]isoindole | 416.2116 |
| 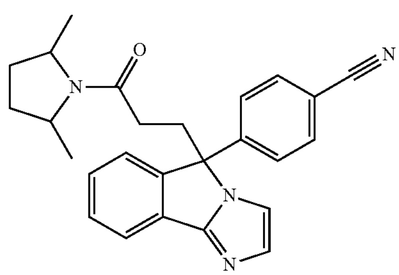 [SMILES: CC1CCC(C)N1C(=O)CCC1(c2ccc(C#N)cc2)c2ccccc2-c2nccn21] | 4-{5-[3-(2,5-dimethylpyrrolidin-1-yl)-3-oxopropyl]-5H-imidazo[2,1-a]isoindol-5-yl}benzonitrile | 411.2168 |
| 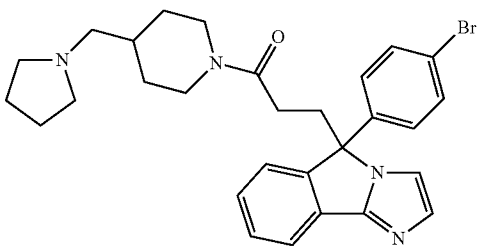 [SMILES: O=C(CCC1(c2ccc(Br)cc2)c2ccccc2-c2nccn21)N1CCC(CN2CCCC2)CC1] | 5-(4-bromophenyl)-5-{3-oxo-3-[4-(pyrrolidin-1-ylmethyl)piperidin-1-yl]propyl}-5H-imidazo[2,1-a]isoindole | 533.1902 |

-continued

| STRUCTURE | Chemical name | Mass found |
|---|---|---|
| 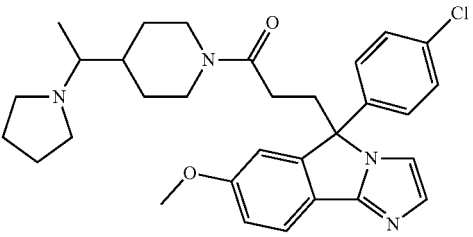 [SMILES: COc1ccc2c(c1)C(CCC(=O)N1CCC(C(C)N3CCCC3)CC1)(c1ccc(Cl)cc1)n1ccnc1-2] | 5-(4-chlorophenyl)-7-methoxy-5-{3-oxo-3-[4-(1-pyrrolidin-1-ylethyl)piperidin-1-yl]propyl}-5H-imidazo[2,1-a]isoindole | 533.2665 |
| 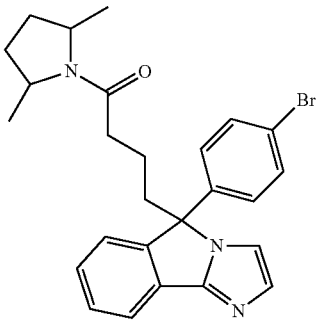 [SMILES: CC1CCC(C)N1C(=O)CCCC1(c2ccc(Br)cc2)c2ccccc2-c2nccn21] | 5-(4-bromophenyl)-5-[4-(2,5-dimethylpyrrolidin-1-yl)-4-oxobutyl]-5H-imidazo[2,1-a]isoindole | 478.1485 |
| 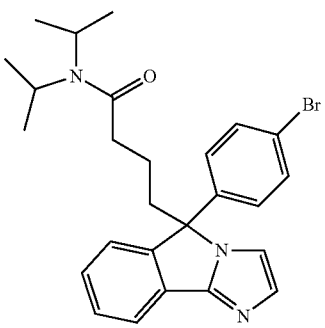 [SMILES: CC(C)N(C(=O)CCCC1(c2ccc(Br)cc2)c2ccccc2-c2nccn21)C(C)C] | 4-[5-(4-bromophenyl)-5H-imidazo[2,1-a]isoindol-5-yl]-N,N-bis(1-methylethyl)butanamide | 480.1636 |
| 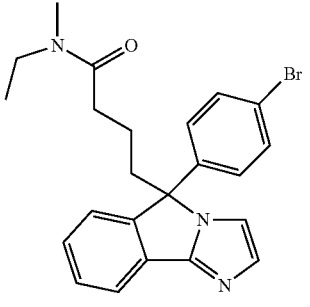 [SMILES: CCN(C)C(=O)CCCC1(c2ccc(Br)cc2)c2ccccc2-c2nccn21] | 4-[5-(4-bromophenyl)-5H-imidazo[2,1-a]isoindol-5-yl]-N-ethyl-N-methylbutanamide | 438.117 |
| 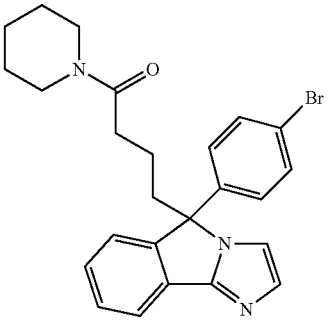 [SMILES: O=C(CCCC1(c2ccc(Br)cc2)c2ccccc2-c2nccn21)N1CCCCC1] | 5-(4-bromophenyl)-5-(4-oxo-4-piperidin-1-ylbutyl)-5H-imidazo[2,1-a]isoindole | 464.1325 |

| STRUCTURE | Chemical name | Mass found |
|---|---|---|
| 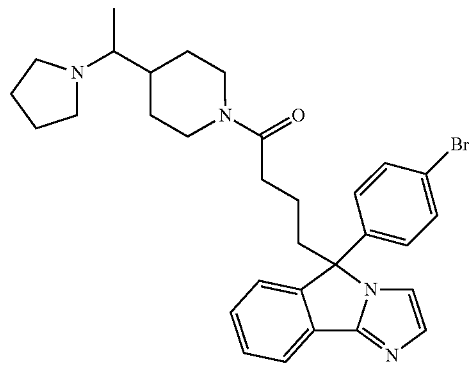 [SMILES: CC(C1CCN(C(=O)CCCC2(c3ccc(Br)cc3)c3ccccc3-c3nccn32)CC1)N1CCCC1] | 5-(4-bromophenyl)-5-{4-oxo-4-[4-(1-pyrrolidin-1-ylethyl)piperidin-1-yl]butyl}-5H-imidazo[2,1-a]isoindole | 561.2218 |
| 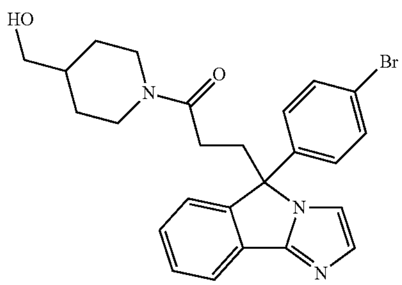 [SMILES: O=C(CCC1(c2ccc(Br)cc2)c2ccccc2-c2nccn21)N1CCC(CO)CC1] | (1-{3-[5-(4-bromophenyl)-5H-imidazo[2,1-a]isoindol-5-yl]propanoyl}piperidin-4-yl)methanol | 482 |
| 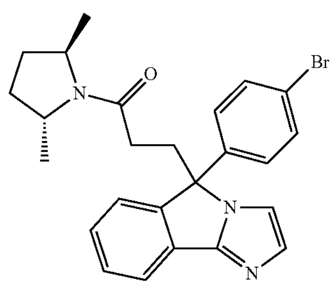 [SMILES: C[C@@H]1CC[C@@H](C)N1C(=O)CCC1(c2ccc(Br)cc2)c2ccccc2-c2nccn21] | 5-(4-bromophenyl)-5-{3-[(2R,5R)-2,5-dimethylpyrrolidin-1-yl]-3-oxopropyl}-5H-imidazo[2,1-a]isoindole | 464.1336 |
| 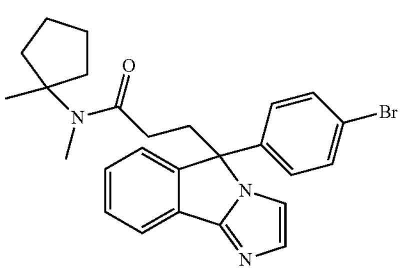 [SMILES: CN(C(=O)CCC1(c2ccc(Br)cc2)c2ccccc2-c2nccn21)C1(C)CCCC1] | 3-[5-(4-bromophenyl)-5H-imidazo[2,1-a]isoindol-5-yl]-N-methyl-N-(1-methyl-cyclopentyl)propanamide | 478.1483 |
| 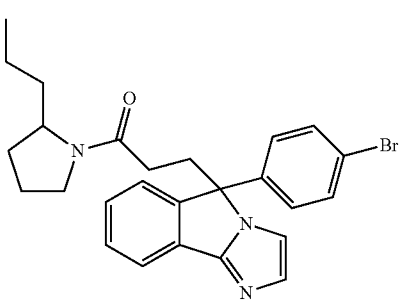 [SMILES: CCCC1CCCN1C(=O)CCC1(c2ccc(Br)cc2)c2ccccc2-c2nccn21] | 5-(4-bromophenyl)-5-[3-oxo-3-(2-propylpyrrolidin-1-yl)propyl]-5H-imidazo[2,1-a]isoindole | 478.1482 |

| STRUCTURE | Chemical name | Mass found |
|---|---|---|
| 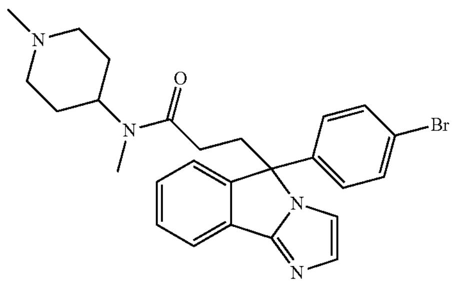 [SMILES: CN1CCC(N(C)C(=O)CCC2(c3ccc(Br)cc3)c3ccccc3-c3nccn32)CC1] | 3-[5-(4-bromophenyl)-5H-imidazo[2,1-a]isoindol-5-yl]-N-methyl-N-(1-methyl-piperidin-4-yl)propanamide | 493.1588 |
| | N-benzyl-3-[5-(4-bromophenyl)-5H-imidazo[2,1-a]isoindol-5-yl]-N-ethylpropanamide | 500.1324 |
| 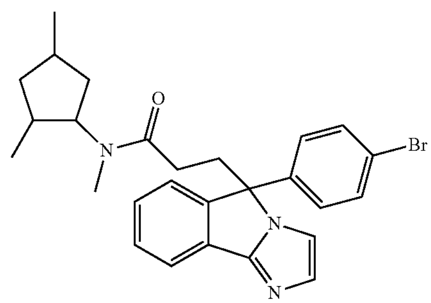 [SMILES: CC1CC(C)C(N(C)C(=O)CCC2(c3ccc(Br)cc3)c3ccccc3-c3nccn32)C1] | 3-[5-(4-bromophenyl)-5H-imidazo[2,1-a]isoindol-5-yl]-N-(2,4-dimethylcyclopentyl)-N-methylpropanamide | 492.1636 |
| 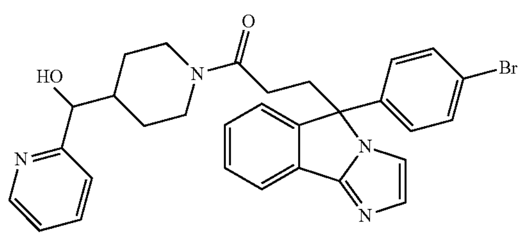 [SMILES: O=C(CCC1(c2ccc(Br)cc2)c2ccccc2-c2nccn21)N1CCC(C(O)c2ccccn2)CC1] | (1-{3-[5-(4-bromophenyl)-5H-imidazo[2,1-a]isoindol-5-yl]propanoyl}piperidin-4-yl)(pyridin-2-yl)methanol | 557.1541 |
| 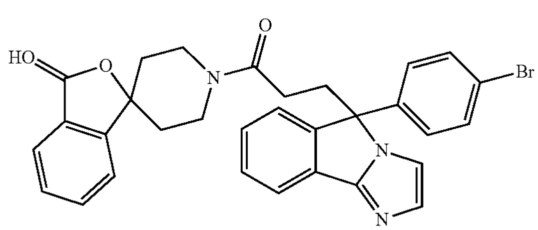 [SMILES: O=C1OC2(CCN(C(=O)CCC3(c4ccc(Br)cc4)c4ccccc4-c4nccn43)CC2)c2ccccc21] | 1'-{3-[5-(4-bromophenyl)-5H-imidazo[2,1-a]isoindol-5-yl]propanoyl}-3H-spiro[2-benzofuran-1,4'-piperidin]-3-one | 568.1224 |
| 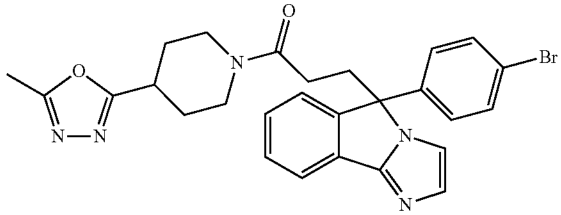 [SMILES: Cc1nnc(C2CCN(C(=O)CCC3(c4ccc(Br)cc4)c4ccccc4-c4nccn43)CC2)o1] | 5-(4-bromophenyl)-5-{3-[4-(5-methyl-1,3,4-oxadiazol-2-yl)piperidin-1-yl]-3-oxopropyl}-5H-imidazo[2,1-a]isoindole | 532.1338 |

-continued

| STRUCTURE | Chemical name | Mass found |
|---|---|---|
| 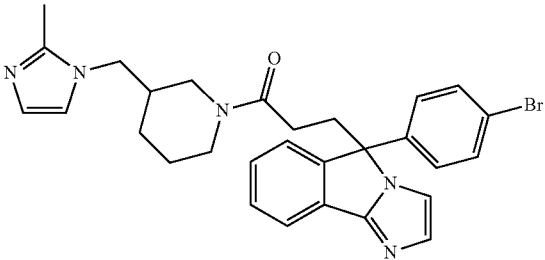 [SMILES: Cc1nccn1CC1CCCN(C(=O)CCC2(c3ccc(Br)cc3)c3ccccc3-c3nccn32)C1] | 5-(4-bromophenyl)-5-(3-{3-[(2-methyl-1H-imidazol-1-yl)methyl]piperidin-1-yl}-3-oxopropyl)-5H-imidazo[2,1-a]isoindole | 544.1699 |
| 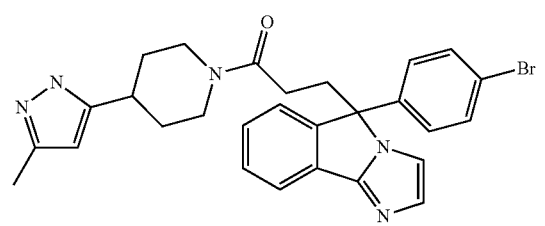 [SMILES: Cc1cc(C2CCN(C(=O)CCC3(c4ccc(Br)cc4)c4ccccc4-c4nccn43)CC2)[nH]n1] | 5-(4-bromophenyl)-5-{3-[4-(3-methyl-1H-pyrazol-5-yl)piperidin-1-yl]-3-oxopropyl}-5H-imidazo[2,1-a]isoindole | 530.1541 |
| 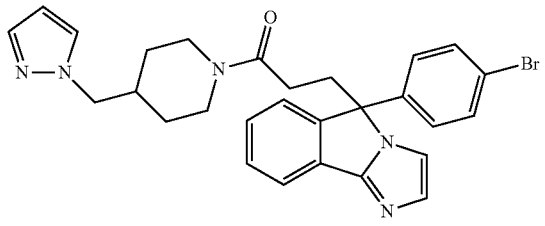 [SMILES: O=C(CCC1(c2ccc(Br)cc2)c2ccccc2-c2nccn21)N1CCC(Cn2cccn2)CC1] | 5-(4-bromophenyl)-5-{3-oxo-3-[4-(1H-pyrazol-1-ylmethyl)piperidin-1-yl]propyl}-5H-imidazo[2,1-a]isoindole | 530.1543 |
| 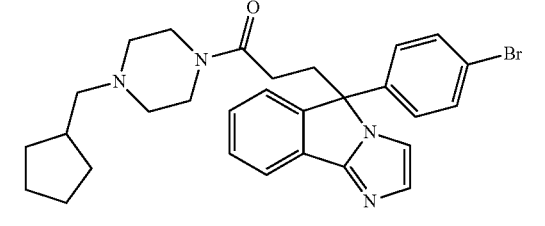 [SMILES: O=C(CCC1(c2ccc(Br)cc2)c2ccccc2-c2nccn21)N1CCN(CC2CCCC2)CC1] | 5-(4-bromophenyl)-5-{3-[4-(cyclopentylmethyl)piperazin-1-yl]-3-oxopropyl}-5H-imidazo[2,1-a]isoindole | 533.1896 |
| 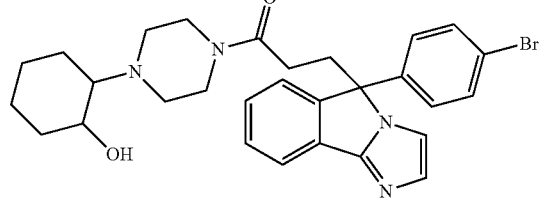 | 2-(4-{3-[5-(4-bromophenyl)-5H-imidazo[2,1-a]isoindol-5-yl]propanoyl}piperazin-1-yl)cyclohexanol | 549.1844 |
| 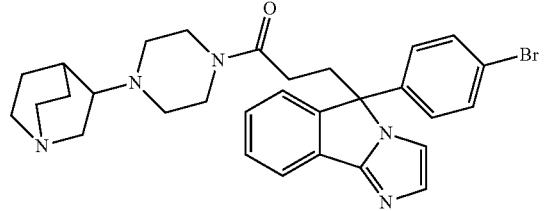 [SMILES: O=C(CCC1(c2ccc(Br)cc2)c2ccccc2-c2nccn21)N1CCN(C2CN3CCC2CC3)CC1] | 5-{3-[4-(1-azabicyclo[2.2.2]oct-3-yl)piperazin-1-yl]-3-oxopropyl}-5-(4-bromophenyl)-5H-imidazo[2,1-a]isoindole | 560.2008 |

-continued

| STRUCTURE | Chemical name | Mass found |
|---|---|---|
| 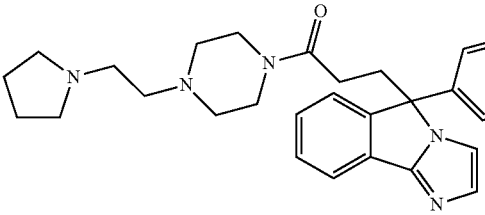 | 5-(4-bromophenyl)-5-{3-oxo-3-[4-(2-pyrrolidin-1-ylethyl)piperazin-1-yl]propyl}-5H-imidazo[2,1-a]isoindole | 548.2007 |
| 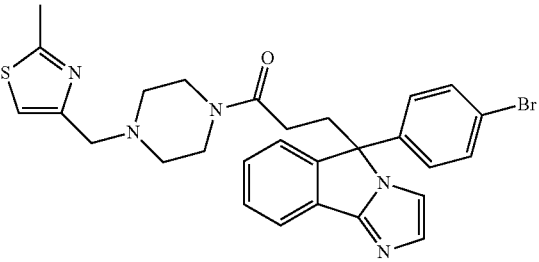 [SMILES: Cc1nc(CN2CCN(C(=O)CCC3(c4ccc(Br)cc4)c4ccccc4-c4nccn43)CC2)cs1] | 5-(4-bromophenyl)-5-(3-{4-[(2-methyl-1,3-thiazol-4-yl)methyl]piperazin-1-yl}-3-oxopropyl)-5H-imidazo[2,1-a]isoindole | 562.1259 |
| 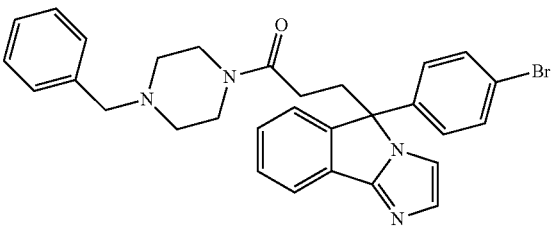 [SMILES: O=C(CCC1(c2ccc(Br)cc2)c2ccccc2-c2nccn21)N1CCN(Cc2ccccc2)CC1] | 5-[3-(4-benzylpiperazin-1-yl)-3-oxopropyl]-5-(4-bromophenyl)-5H-imidazo[2,1-a]isoindole | 541.159 |
| 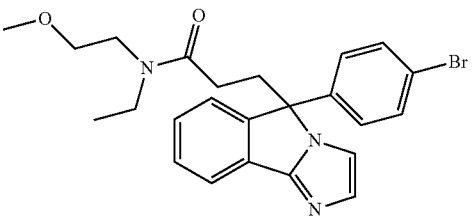 [SMILES: CCN(CCOC)C(=O)CCC1(c2ccc(Br)cc2)c2ccccc2-c2nccn21] | 3-[5-(4-bromophenyl)-5H-imidazo[2,1-a]isoindol-5-yl]-N-ethyl-N-(2-methoxyethyl)propanamide | 468.1273 |
| 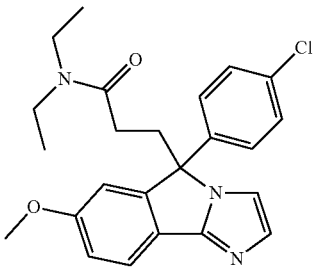 [SMILES: CCN(CC)C(=O)CCC1(c2ccc(Cl)cc2)c2cc(OC)ccc2-c2nccn21] | 3-[5-(4-chlorophenyl)-7-methoxy-5H-imidazo[2,1-a]isoindol-5-yl]-N,N-diethylpropanamide | 424.1782 |
| 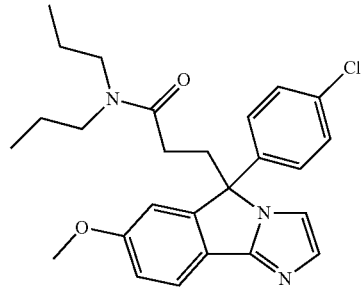 [SMILES: CCCN(CCC)C(=O)CCC1(c2ccc(Cl)cc2)c2cc(OC)ccc2-c2nccn21] | 3-[5-(4-chlorophenyl)-7-methoxy-5H-imidazo[2,1-a]isoindol-5-yl]-N,N-dipropylpropanamide | 452.2098 |

-continued
| STRUCTURE | Chemical name | Mass found |
|---|---|---|
| 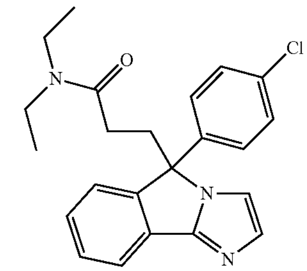 [SMILES: CCN(CC)C(=O)CCC1(c2ccc(Cl)cc2)c2ccccc2-c2nccn21] | 3-[5-(4-chlorophenyl)-5H-imidazo[2,1-a]isoindol-5-yl]-N,N-diethylpropanamide | 394.1 (low res) |
| 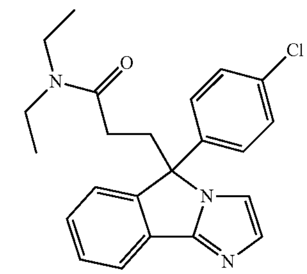 [SMILES: CCN(CC)C(=O)CCC1(c2ccc(Cl)cc2)c2ccccc2-c2nccn21] | 3-[5-(4-chlorophenyl-5H-imidazo[2,1-a]isoindol-5-yl]-N,N-diethylpropanamide | 416.1508 |
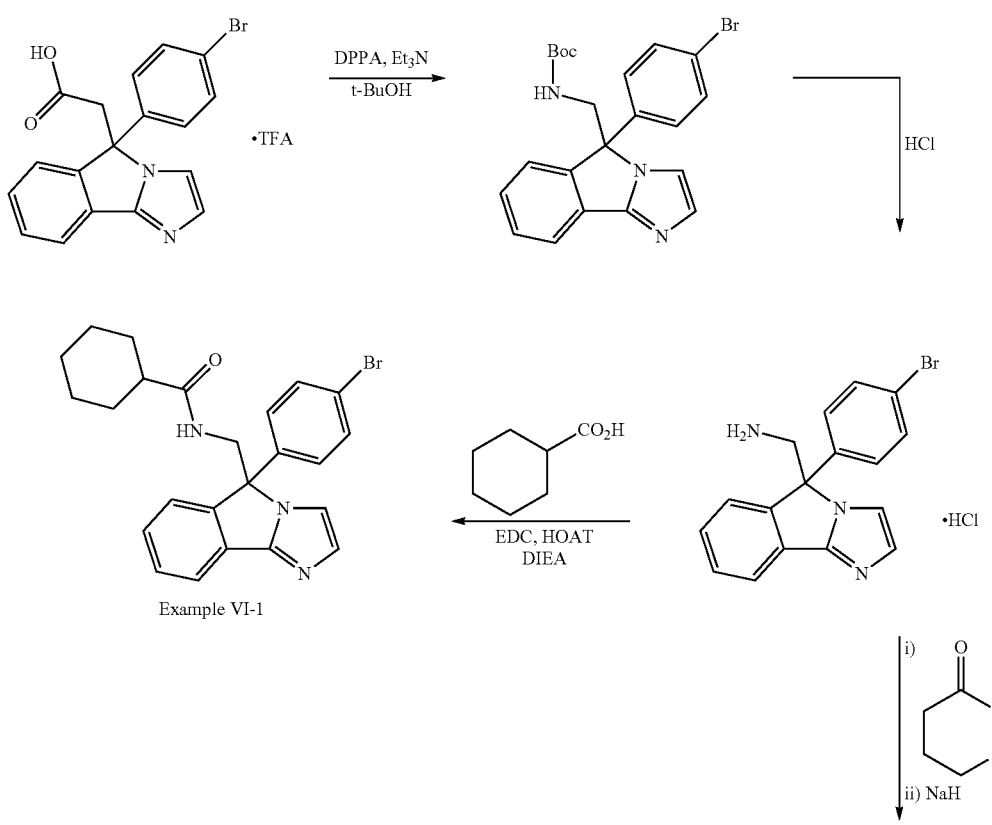
SCHEME VI
Example VI-1

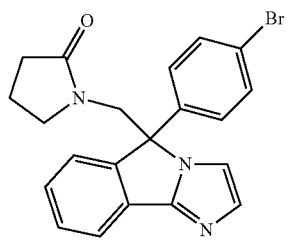

Example VI-2

EXAMPLES VI-1 AND VI-2

Step 1: tert-butyl {[5-(4-bromophenyl)-5H-imidazo[2,1-a]isoindol-5-yl]methyl}carbamate A mixture of 5-(4-bromophenyl)-5-(carboxymethyl)-5H-imidazo[2,1-a]isoindol-1-ium trifluoroacetate (1.27 g), Et₃N (0.989 mL) and 4 Angstrom powdered molecular sieves in t-BuOH (10 mL) was stirred for 20 minutes at room temperature. Diphenylphosphorylazide was then added to this mixture and heated at 95° C. overnight. After cooling to room temperature the reaction mixture was filtered through a pad of celite. The celite pad was washed thoroughly with CH₂Cl₂, combined washings and filtrate were concentrated. The residue was dissolved in CH₂Cl₂ and the organic layer was washed with half-saturated aqueous NaHCO₃ solution (1×), dried over Na₂SO₄ and concentrated. Flash chromatography using a linear gradient of 3% EtOAc/0% MeOH to 50% EtOAc/2% MeOH in hexanes afforded title compound as a white solid. Mass. found (M+H)⁺, 442.0.

Step 2: 5-(aminomethyl)-5-(4-bromophenyl)-5H-imidazo[2,1-a]isoindol-1-ium Chloride To a solution of tert-butyl {[5-(4-bromophenyl)-5H-imidazo[2,1-a]isoindol-5-yl]methyl}carbamate (575 mg) in dioxane (2 mL) was added a HCl solution (3.265 mL, 4 M in dioxane) and stirred at room temperature for 1.5 h. After this time 1.5 mL more HCl solution was added and stirring continued for another 3 h. The reaction mixture was then concentrated (azeotroped once from toluene) and dried under vacuum to give title compound as a white solid. Mass. found (M+H)⁺, 342.0.

Step 3, Example VI-1: N-{[5-(4-bromophenyl)-5H-imidazo[2,1-a]isoindol-5-yl]methyl}cyclohexanecarboxamide To a mixture of 5-(aminomethyl)-5-(4-bromophenyl)-5H-imidazo[2,1-a]isoindol-1-ium chloride (40 mg), EDC (28 mg) and HOAT (13 mg) in DMF (1 mL) was added Hunig's base (75 mg) followed by cyclohexanecarboxylic acid (19 mg). After stirring at 40° C. overnight the mixture was purified by reversed phase HPLC (21×100 mm Phenomenex Gemini, 15-75% MeCN/water containing 0.05% NH₄OH over 20 min at 20 mL/min) to give title compound as a white solid. HRMS. Found, 450.1186; calcd for (M+H)⁺, 450.1176. ¹H NMR (500 MHz, CDCl₃): δ 7.85 (d, J=7.59 Hz, 1 H); 7.48 (d, J=8.42 Hz, 2 H); 7.46-7.40 (m, 1 H); 7.35-7.28 (m, 3 H); 7.07 (d, J=8.43 Hz, 2 H); 7.03 (d, J=1.34 Hz, 1 H); 4.84 (t, J=6.19 Hz, 1 H); 4.55 (dd, J=13.97, 6.66 Hz, 1 H); 4.24 (dd, J=13.99, 5.93 Hz, 1 H); 1.75-1.49 (m, 5 H); 1.39 (d, J=9.99 Hz, 1 H); 1.28 (d, J=12.70 Hz, 1 H); 1.05 (m, 4 H).

Step 4, Example VI-2: 1-{[5-(4-bromophenyl)-5H-imidazo[2,1-a]isoindol-5-yl]methyl}piperidin-2-one To a stirred biphasic mixture of a solution of 5-(aminomethyl)-5-(4-bromophenyl)-5H-imidazo[2,1-a]isoindol-1-ium chloride (25 mg) in CH₂Cl₂ (3 mL) and aqueous saturated NaHCO₃ (3 mL) was added a solution of 5-bromobutyryl chloride (34 mg) in CH₂Cl₂ (1 mL). After 30 minutes layers were separated. Organic layer was dried over Na₂SO₄ and concentrated. The residue was then dissolved in DMF (0.5 mL) and NaH (12 mg, 60% in mineral oil) was added and stirred for 30 minutes. The reaction was then quenched with water, diluted with DMF and filtered. Purification by reversed phase HPLC (21×100 mm Phenomenex Gemini, 5-55% MeCN/water containing 0.1% TFA over 20 min at 20 mL/min) afforded title compound as a white solid. HRMS. Found, 408.0718; calcd for (M+H)⁺, 408.0706. ¹H NMR (500 MHz, CDCl₃): δ 7.98 (s, 1 H); 7.52-7.43 (m, 4 H); 7.39-7.34 (m, 2 H); 7.16 (d, J=1.54 Hz, 1 H); 7.13-7.09 (m, 2 H); 4.57 (d, J=14.04 Hz, 1 H); 4.38 (d, J=14.28 Hz, 1 H); 2.52-2.46 (m, 2 H); 2.09-1.95 (m, 2 H), 1.62 (p, J=7.47 Hz, 2 H).

The following compounds were prepared using the experimental procedure described above for Scheme VI.

| STRUCTURE | Chemical name | Mass found |
|---|---|---|
| 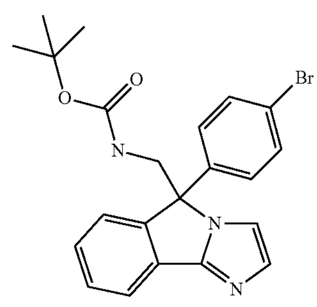 [SMILES: CC(C)(C)OC(=O)NCC1(c2ccc(Br)cc2)c2ccccc2-c2nccn21] | tert-butyl {[5-(4-bromophenyl)-5H-imidazo[2,1-a]isoindol-5-yl]methyl}carbamate | 440.0979 |
| 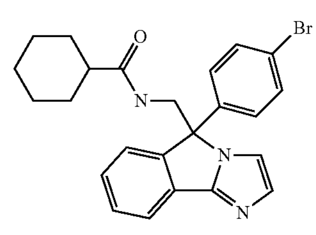 [SMILES: O=C(NCC1(c2ccc(Br)cc2)c2ccccc2-c2nccn21)C1CCCCC1] | N-{[5-(4-bromophenyl)-5H-imidazo[2,1-a]isoindol-5-yl]methyl}cyclohexanecarboxamide | 450.1186 |

| STRUCTURE | Chemical name | Mass found |
|---|---|---|
| 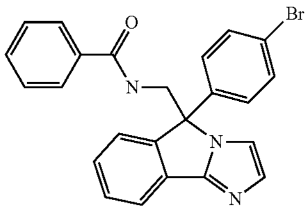 [SMILES: O=C(NCC1(c2ccc(Br)cc2)c2ccccc2-c2nccn21)c1ccccc1] | N-{[5-(4-bromophenyl)-5H-imidazo[2,1-a]isoindol-5-yl]methyl}benzamide | 444.072 |
| 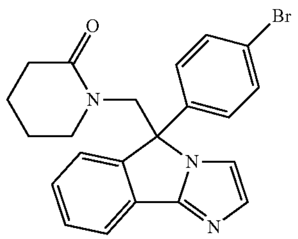 [SMILES: O=C1CCCCN1CC1(c2ccc(Br)cc2)c2ccccc2-c2nccn21] | 1-{[5-(4-bromophenyl)-5H-imidazo[2,1-a]isoindol-5-yl]methyl}piperidin-2-one | 424 |
| 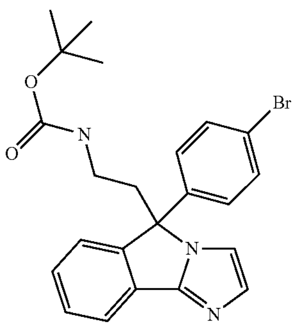 [SMILES: CC(C)(C)OC(=O)NCCC1(c2ccc(Br)cc2)c2ccccc2-c2nccn21] | tert-butyl {2-[5-(4-bromophenyl)-5H-imidazo[2,1-a]isoindol-5-yl]ethyl}carbamate | 454.1136 |
| 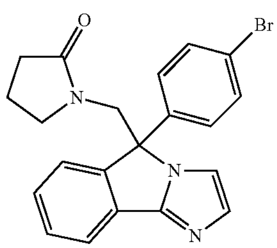 [SMILES: O=C1CCCN1CC1(c2ccc(Br)cc2)c2ccccc2-c2nccn21] | 1-{[5-(4-bromophenyl)-5H-imidazo[2,1-a]isoindol-5-yl]methyl}pyrrolidin-2-one | 408.0718 |
| 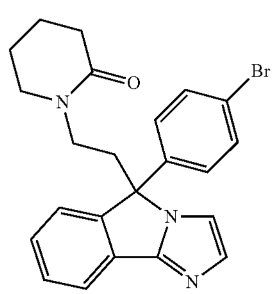 [SMILES: O=C1CCCCN1CCC1(c2ccc(Br)cc2)c2ccccc2-c2nccn21] | 1-{2-[5-(4-bromophenyl)-5H-imidazo[2,1-a]isoindol-5-yl]ethyl}piperidin-2-one | 436.1031 |
| 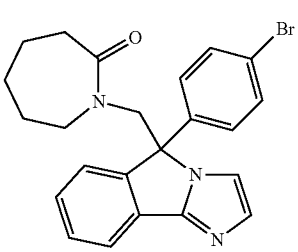 [SMILES: O=C1CCCCCN1CC1(c2ccc(Br)cc2)c2ccccc2-c2nccn21] | 1-{[5-(4-bromophenyl)-5H-imidazo[2,1-a]isoindol-5-yl]methyl}azepan-2-one | 436.1028 |
| | N-{2-[5-(4-bromophenyl)-5H-imidazo[2,1-a]isoindol-5-yl]ethyl}cyclohexanecarboxamide | 464.1326 |
| | N-{2-[5-(4-bromophenyl)-5H-imidazo[2,1-a]isoindol-5-yl]ethyl}cyclopentanecarboxamide | 450.117 |
| | N-{2-[5-(4-bromophenyl)-5H-imidazo[2,1-a]isoindol-5-yl]ethyl}-2-methylpropanamide | 424.1011 |
| | 1-{4-[5-(4-chlorophenyl)-5H-imidazo[2,1-a]isoindol-5-yl]butyl}pyrrolidin-2-one | 406.1691 |
| | 1-{4-[5-(4-chlorophenyl)-5H-imidazo[2,1-a]isoindol-5-yl]butyl}piperidin-2-one | 420.1846 |

SCHEME VII

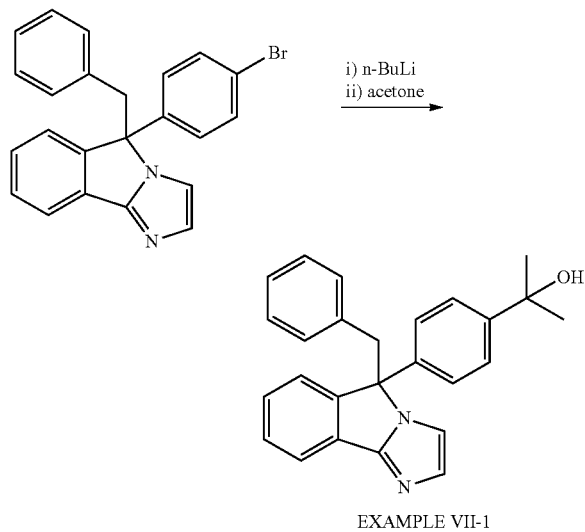

EXAMPLE VII-1

Step 1, Example VII-1: 2-[4-(5-benzyl-5H-imidazo[2,1-a]isoindol-5-yl)phenyl]propan-2-ol A suspension of 5-benzyl-5-(4-bromophenyl)-5H-imidazo[2,1-a]isoindole (100 mg) in THF (3 mL) was cooled to −78° C. and n-BuLi solution (0.234 mL, 1.6 M in hexane) was added slowly. After stirring for 10 minutes acetone (29 mg) was added to the resulting red solution. After 30 min of the addition of acetone, reaction was quenched with aqueous saturated $NH_4Cl$. The reaction mixture was partitioned between saturated aqueous $NH_4Cl$ and EtOAc.

Aqueous layer was extracted with EtOAc (2×). Combined organic layers were dried over $Na_2SO_4$ and concentrated. Purification by reversed phase HPLC (21×100 mm Phenomenex Gemini, 5-50% MeCN/water containing 0.1% TFA over 20 min at 20 mL/min) afforded title compound as a white solid. HRMS. Found, 381.1962; calcd for $(M+H)^+$, 3891.1962. $^1$H NMR (500 MHz, $CDCl_3$): δ 7.62-7.58 (m, 1 H); 7.52-7.45 (m, 2 H); 7.42-7.37 (m, 1 H); 7.31-7.25 (m, 3 H); 7.24 (d, J=2.84 Hz, 2 H); 7.04-6.89 (m, 4 H); 6.56 (d, J=7.52 Hz, 2 H); 3.88-3.76 (m, 2 H); 1.73 (s, 1 H); 1.57 (s, 6 H).

The following compound was prepared using the experimental procedure described above for Scheme VII.

| STRUCTURE | Chemical name | Mass found |
|---|---|---|
| 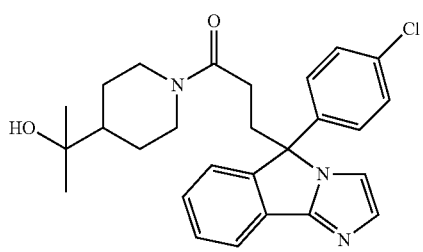 | 2-[4-(5-benzyl-5H-imidazo[2,1-a]isoindol-5-yl)phenyl]propan-2-ol | 381.1962 |

SCHEME VIII

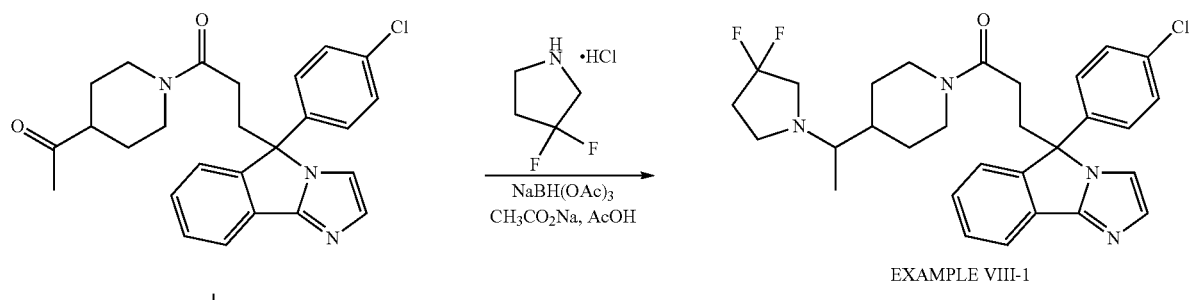

EXAMPLE VIII-1

MeMgBr ↓

EXAMPLE VIII-2

EXAMPLES VIII-1 AND VIII-2

Step 1, Example VIII-1: 5-(4-chlorophenyl)-5-(3-{4-[1-(3,3-difluoropyrrolidin-1-yl)ethyl]piperidin-1-yl}-3-oxopropyl)-5H-imidazo[2,1-a]isoindole To a mixture of 1-(1-{3-[5-(4-chlorophenyl)-5H-imidazo[2,1-a]isoindol-5-yl]propanoyl}piperidin-4-yl)ethanone (27 mg), 3,3-difluoropyrrolidinium chloride (17 mg) and NaOAc (15 mg) in $CH_2Cl_2$ was added AcOH (0.01 mL). After stirring the resulting mixture for 30 minutes $NaBH(OAc)_3$ (26 mg) was added and allowed to stir overnight. The reaction mixture was then partitioned between saturated aqueous $NaHCO_3$ and $CH_2Cl_2$. Aqueous layer was extracted with $CH_2Cl_2$ (2×). Combined organic layers were dried over $Na_2SO_4$ and concentrated. Purification by reversed phase HPLC (21×100 mm Phenomenex Gemini, 15-95% MeCN/water containing 0.05% $NH_4OH$ over 20 min at 20 mL/min) afforded title compound as a white solid. HRMS. Found, 539.2387; calcd for $(M+H)^+$, 539.2384. $^1$H NMR (500 MHz, $CDCl_3$): δ 7.86 (d, J=7.62 Hz, 1 H); 7.43-7.38 (m, 1 H); 7.35-7.26 (m, 4 H); 7.25-7.19 (m, 1 H); 7.11 (d, J=8.36 Hz, 2 H); 6.96 (d, J=9.03 Hz, 1 H); 4.54 (d, J=13.34 Hz, 1 H); 3.31 (d, J=13.41 Hz, 1 H); 3.11-3.03 (m, 1 H); 2.91-2.80 (m, 3 H); 2.76-2.61 (m, 3 H); 2.38-2.13 (m, 4 H); 1.69-1.50 (m, 6 H); 0.90-0.83 (m, 4 H).

Step 2, Example VIII-2: 2-(1-{3-[5-(4-chlorophenyl)-5H-imidazo[2,1-a]isoindol-5-yl]propanoyl}piperidin-4-yl)propan-2-ol To a solution of 1-(1-{3-[5-(4-chlorophenyl)-5H-imidazo[2,1-a]isoindol-5-yl]propanoyl}piperidin-4-yl)ethanone (25 mg) in THF (0.8 mL) at −78° C. was added a solution of MeMgBr (0.028 mL, 3 M in ether). The cooling bath was then removed and the reaction mixture was stirred at room temperature for 30 minutes. It was then cooled back to −78° C., 0.15 mL more Grignard solution added, cooling bath removed and was stirred at room temperature for 20 minutes. Reaction was quenched with saturated aqueous $NH_4Cl$, partitioned between saturated aqueous $NH_4Cl$ and $CH_2Cl_2$. Aqueous layer was extracted with $CH_2Cl_2$ (2×). Combined organic layers were dried over $Na_2SO_4$ and concentrated. Purification by reversed phase HPLC (21×100 mm Phenomenex Gemini, 15-75% MeCN/water containing 0.05% $NH_4OH$ over 20 min at 20 mL/min) afforded title compound as a white solid. HRMS. Found, 464.2099; calcd for $(M+H)^+$, 464.2099. $^1$H NMR (500 MHz, $CDCl_3$): δ 7.86 (d, J=7.58 Hz, 1 H); 7.43-7.38 (m, 1 H); 7.36-7.26 (m, 4 H); 7.25-7.19 (m, 1 H); 7.11 (d, J=8.54 Hz, 2 H); 6.96 (d, J=9.11 Hz, 1 H); 4.59 (d, J=13.19 Hz, 1 H); 3.34 (d, J=13.18 Hz, 1 H); 3.12-3.04 (m, 1 H); 2.89-2.82 (m, 1 H); 2.68-2.59 (m, 1 H); 2.36-2.29 (m, 1 H); 1.71-1.55 (m, 3 H); 1.41-1.34 (m, 1 H); 1.16-1.10 (m, 6 H); 1.09-0.92 (m, 1 H); 0.93-0.83 (m, 1 H).

The following compounds were prepared using the experimental procedure described above for Scheme VIII.

| STRUCTURE | Chemical name | Mass found |
|---|---|---|
| 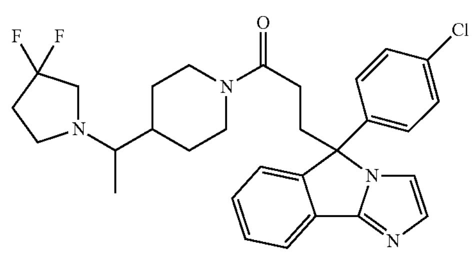 [SMILES: CC(C1CCN(C(=O)CCC2(c3ccc(Cl)cc3)c3ccccc3-c3nccn32)CC1)N1CCC(F)(F)C1] | 5-(4-chlorophenyl)-5-(3-{4-[1-(3,3-difluoropyrrolidin-1-yl)ethyl]piperidin-1-yl}-3-oxopropyl)-5H-imidazo[2,1-a]isoindole | 539.2378 |
| 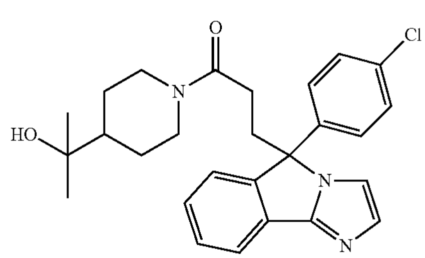 [SMILES: CC(C)(O)C1CCN(C(=O)CCC2(c3ccc(Cl)cc3)c3ccccc3-c3nccn32)CC1] | 2-(1-{3-[5-(4-chlorophenyl)-5H-imidazo[2,1-a]isoindol-5-yl]propanoyl}piperidin-4-yl)propan-2-ol | 464.2099 |

SCHEME IX

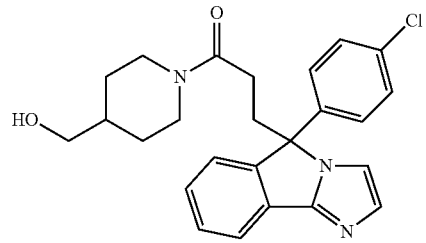 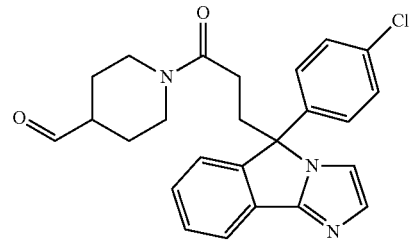

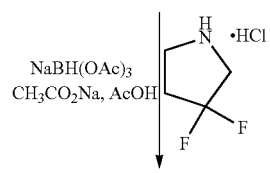

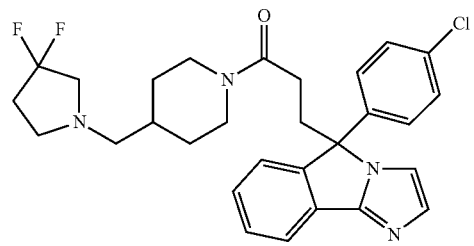

EXAMPLE IX-1

EXAMPLE IX-1

Step 1: 1-{3-[5-(4-chlorophenyl)-5H-imidazo[2,1-a]isoindol-5-yl]propanoyl}piperidine-4-carbaldehyde To a solution of (1-{3-[5-(4-chlorophenyl)-5H-imidazo[2,1-a]isoindol-5-yl]propanoyl}piperidin-4-yl)methanol (36 mg) in CH$_2$Cl$_2$ was added resin (polystyrene) bound IBX (2 equivalent) and allowed to react overnight. The reaction mixture was then filtered through a fitted funnel and the resin was washed thoroughly with THF. Combined filtrate and washings were concentrated to give the title compound as a colorless glass. Mass. found (M+H)$^+$, 480.0.

Step 2, Example IX-1: 5-(4-bromophenyl)-5-(3-{4-[(3,3-difluoropyrrolidin-1-yl)methyl]piperidin-1-yl}-3-oxopropyl)-5H-imidazo[2,1-a]isoindole To a mixture of 1-{3-[5-(4-chlorophenyl)-5H-imidazo[2,1-a]isoindol-5-yl]propanoyl}piperidine-4-carbaldehyde (36 mg), 3,3-difluoropyrrolidinium chloride (16 mg) and NaOAc (14 mg) in CH$_2$Cl$_2$ was added AcOH (0.013 mL). After stirring the resulting mixture for 30 minutes NaBH(OAc)$_3$ (32 mg) was added and allowed to stir for 1 h. The reaction mixture was then partitioned between saturated aqueous NaHCO$_3$ and CH$_2$Cl$_2$. Aqueous layer was extracted with CH$_2$Cl$_2$ (2×). Combined organic layers were dried over Na$_2$SO$_4$ and concentrated. Purification by reversed phase HPLC (21×100 mm Phenomenex Gemini, 15-95% MeCN/water containing 0.1% TFA over 20 min at 20 mL/min) afforded title compound as a white solid.

HRMS. Found, 569.1732; calcd for (M+H)$^+$, 569.1722. $^1$H NMR (500 MHz, CDCl$_3$): δ 7.85 (d, J=7.63 Hz, 1 H); 7.44 (d, J=8.55 Hz, 2 H); 7.43-7.39 (m, 1 H); 7.33 (s, 1 H); 7.29-7.26 (m, 1 H); 7.22 (t, J=7.10 Hz, 1 H); 7.04 (d, J=8.47 Hz, 2 H); 6.95 (d, J=6.58 Hz, 1 H); 4.46 (d, J=13.40 Hz, 1 H); 3.27 (d, J=13.56 Hz, 1 H); 3.09-3.04 (m, 1 H); 2.89-2.77 (m, 3 H); 2.70-2.62 (m, 3 H); 2.44-2.38 (m, 1 H); 2.27-2.17 (m, 4 H); 1.72-1.39 (m, 5 H); 0.96-0.82 (m, 2 H).

The following compounds were prepared using the experimental procedure described above for Scheme IX.

| STRUCTURE | Chemical name | Mass found |
|---|---|---|
| 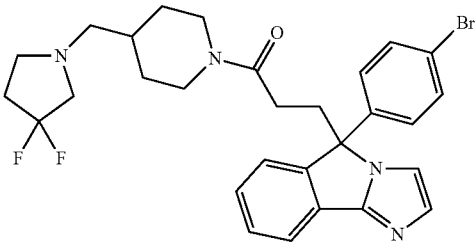 [SMILES: O=C(CCC1(c2ccc(Br)cc2)c2ccccc2-c2nccn21)N1CCC(CN2CCC(F)(F)C2)CC1] | 5-(4-bromophenyl)-5-(3-{4-[(3,3-difluoropyrrolidin-1-yl)methyl]piperidin-1-yl}-3-oxopropyl)-5H-imidazo[2,1-a]isoindole | 569.1732 |
| 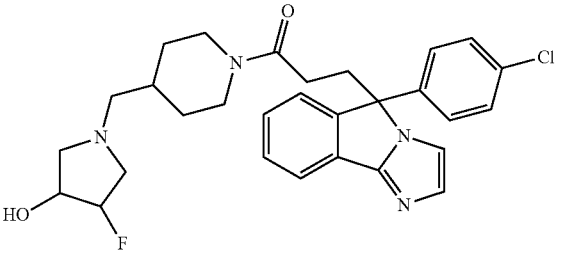 [SMILES: O=C(CCC1(c2ccc(Cl)cc2)c2ccccc2-c2nccn21)N1CCC(CN2CC(O)C(F)C2)CC1] | 1-[(1-{3-[5-(4-chlorophenyl)-5H-imidazo[2,1-a]isoindol-5-yl]propanoyl}piperidin-4-yl)methyl]-4-fluoropyrrolidin-3-ol | 523.2269 |
| 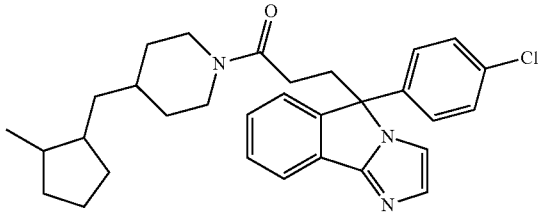 [SMILES: CC1CCCC1CC1CCN(C(=O)CCC2(c3ccc(Cl)cc3)c3ccccc3-c3nccn32)CC1] | 5-(4-chlorophenyl)-5-(3-{4-[(2-methylpyrrolidin-1-yl)methyl]piperidin-1-yl}-3-oxopropyl)-5H-imidazo[2,1-a]isoindole | 525.2379 |
| 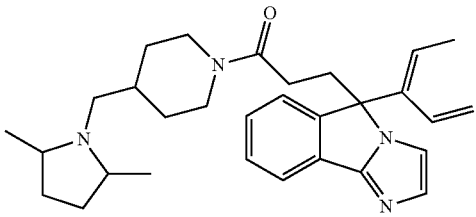 [SMILES: C=C/C(=C\C)C1(CCC(=O)N2CCC(CN3C(C)CCC3C)CC2)c2ccccc2-c2nccn21] | 5-(4-chlorophenyl)-5-(3-{4-[(2,5-dimethylpyrrolidin-1-yl)methyl]piperidin-1-yl}-3-oxopropyl)-5H-imidazo[2,1-a]isoindole | 517.2725 |
| 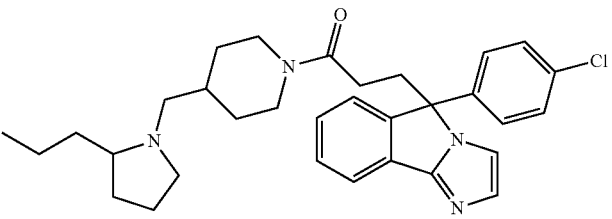 [SMILES: CCCC1CCCN1CC1CCN(C(=O)CCC2(c3ccc(Cl)cc3)c3ccccc3-c3nccn32)CC1] | 5-(4-chlorophenyl)-5-(3-oxo-3-{4-[(2-propylpyrrolidin-1-yl)methyl]piperidin-1-yl}propyl)-5H-imidazo[2,1-a]isoindole | 531.2884 |
| 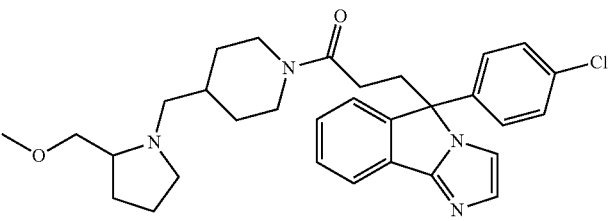 [SMILES: COCC1CCCN1CC1CCN(C(=O)CCC2(c3ccc(Cl)cc3)c3ccccc3-c3nccn32)CC1] | 5-(4-chlorophenyl)-5-[3-(4-{[2-(methoxymethyl)pyrrolidin-1-yl]methyl}piperidin-1-yl)-3-oxopropyl]-5H-imidazo[2,1-a]isoindole | 533.2676 |

-continued

| STRUCTURE | Chemical name | Mass found |
|---|---|---|
| 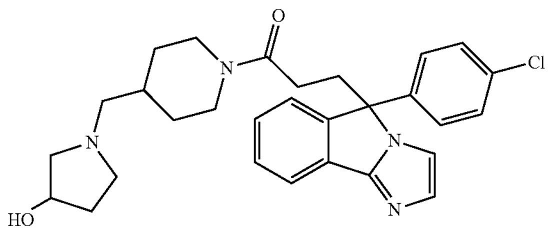 [SMILES: O=C(CCC1(c2ccc(Cl)cc2)c2ccccc2-c2nccn21)N1CCC(CN2CCC(O)C2)CC1] | 1-[(1-{3-[5-(4-chlorophenyl)-5H-imidazo[2,1-a]isoindol-5-yl]propanoyl}piperidin-4-yl)methyl]pyrrolidin-3-ol | 505.2369 |
| 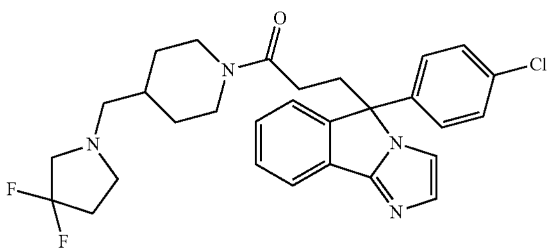 [SMILES: O=C(CCC1(c2ccc(Cl)cc2)c2ccccc2-c2nccn21)N1CCC(CN2CCC(F)(F)C2)CC1] | 5-(4-chlorophenyl)-5-(3-{4-[(3,3-difluoropyrrolidin-1-yl)methyl]piperidin-1-yl}-3-oxopropyl)-5H-imidazo[2,1-]isoindole | 525.2228 |
| | 5-(4-chlorophenyl)-5-[3-oxo-3-(4-{[3-(trifluoromethyl)pyrrolidin-1-yl]methyl}piperidin-1-yl)propyl]-5H-imidazo[2,1-a]isoindole | 557.2291 |
| 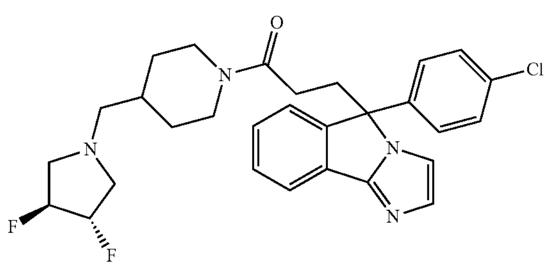 [SMILES: O=C(CCC1(c2ccc(Cl)cc2)c2ccccc2-c2nccn21)N1CCC(CN2C[C@H](F)[C@@H](F)C2)CC1] | 5-(4-chlorophenyl)-5-[3-(4-{[(3S,4S)-3,4-difluoropyrrolidin-1-yl]methyl}piperidin-1-yl)-3-oxopropyl]-5H-imidazo[2,1-a]isoindole | 525.2229 |
| (Abs) | 5-(4-chlorophenyl)-5-[3-(4-{[(3S)-3-fluoropyrrolidin-1-yl]methyl}piperidin-1-yl)-3-oxopropyl]-5H-imidazo[2,1-a]isoindole | 507.2316 |
| (Abs) | 5-(4-chlorophenyl)-5-[3-(4-{[(3R)-3-fluoropyrrolidin-1-yl]methyl}piperidin-1-yl)-3-oxopropyl]-5H-imidazo[2,1-a]isoindole | 507.2 |

| STRUCTURE | Chemical name | Mass found |
|---|---|---|
| | 5-{3-[4-(azetidin-1-ylmethyl)piperidin-1-yl]-3-oxopropyl}-5-(4-chlorophenyl)-5H-imidazo[2,1-a]isoindole | 475.2256 |
| 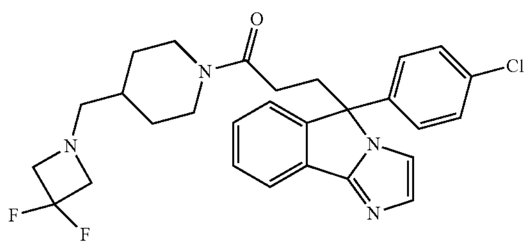 [SMILES: O=C(CCC1(c2ccc(Cl)cc2)c2ccccc2-c2nccn21)N1CCC(CN2CC(F)(F)C2)CC1] | 5-(4-chlorophenyl)-5-(3-{4-[(3,3-difluoroazetidin-1-yl)methyl]piperidin-1-yl}-3-oxopropyl)-5H-imidazo[2,1-a]isoindole | 511.2067 |
| 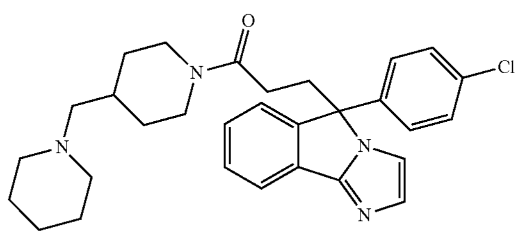 [SMILES: O=C(CCC1(c2ccc(Cl)cc2)c2ccccc2-c2nccn21)N1CCC(CN2CCCCC2)CC1] | 5-(4-chlorophenyl)-5-{3-oxo-3-[4-(piperidin-1-ylmethyl)piperidin-1-yl]propyl}-5H-imidazo[2,1-a]isoindole | 503.2 |
| 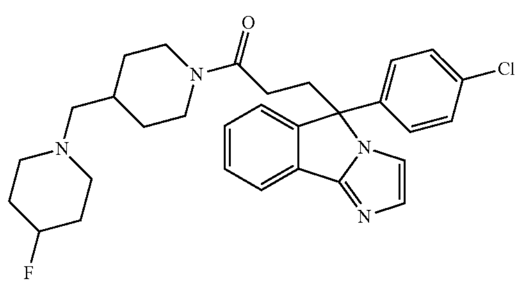 [SMILES: O=C(CCC1(c2ccc(Cl)cc2)c2ccccc2-c2nccn21)N1CCC(CN2CCC(F)CC2)CC1] | 5-(4-chlorophenyl)-5-(3-{4-[(4-fluoropiperidin-1-yl)methyl]piperidin-1-yl}-3-oxopropyl)-5H-imidazo[2,1-a]isoindole | 521.2474 |
| 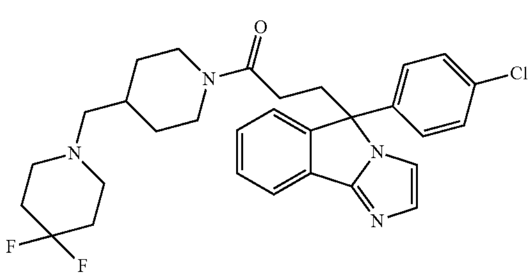 [SMILES: O=C(CCC1(c2ccc(Cl)cc2)c2ccccc2-c2nccn21)N1CCC(CN2CCC(F)(F)CC2)CC1] | 5-(4-chlorophenyl)-5-(3-{4-[(4,4-difluoropiperidin-1-yl)methyl]piperidin-1-yl}-3-oxopropyl)-5H-imidazo[2,1-a]isoindole | 539.2383 |
| 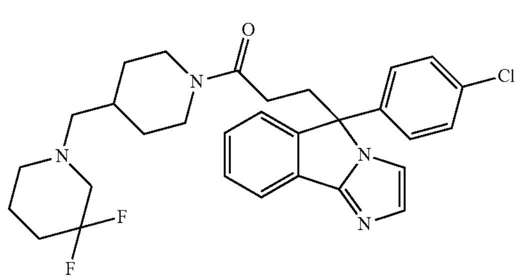 [SMILES: O=C(CCC1(c2ccc(Cl)cc2)c2ccccc2-c2nccn21)N1CCC(CN2CCCC(F)(F)C2)CC1] | 5-(4-chlorophenyl)-5-(3-{4-[(3,3-difluoropiperidin-1-yl)methyl]piperidin-1-yl}-3-oxopropyl)-5H-imidazo[2,1-a]isoindole | 539.2375 |

| STRUCTURE | Chemical name | Mass found |
|---|---|---|
| 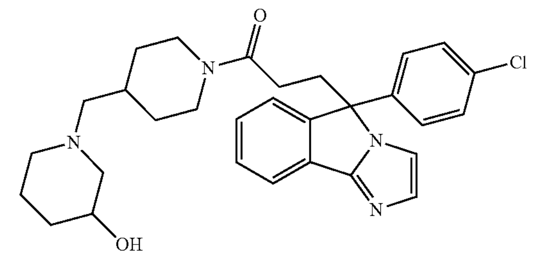 [SMILES: O=C(CCC1(c2ccc(Cl)cc2)c2ccccc2-c2nccn21)N1CCC(CN2CCCC(O)C2)CC1] | 1-[(1-{3-[5-(4-chlorophenyl)-5H-imidazo[2,1-a]isoindol-5-yl]propanoyl}piperidin-4-yl)methyl]piperidin-3-ol | 519.252 |
| 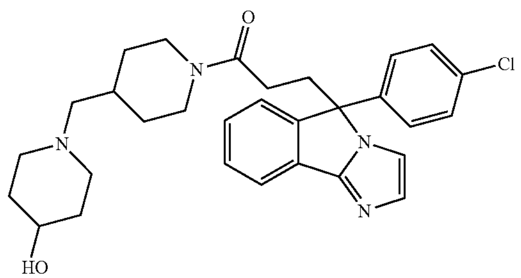 | 1-[(1-{3-[5-(4-chlorophenyl)-5H-imidazo[2,1-a]isoindol-5-yl]propanoyl}piperidin-4-yl)methyl]piperidin-4-ol | 519.2521 |
| 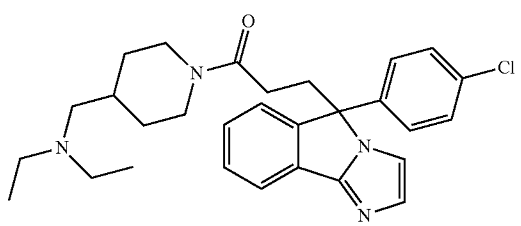 [SMILES: CCN(CC)CC1CCN(C(=O)CCC2(c3ccc(Cl)cc3)c3ccccc3-c3nccn32)CC1] | N-[(1-{3-[5-(4-chlorophenyl)-5H-imidazo[2,1-a]isoindol-5-yl]propanoyl}piperidin-4-yl)methyl]-N-ethylethanamine | 491.2569 |
| 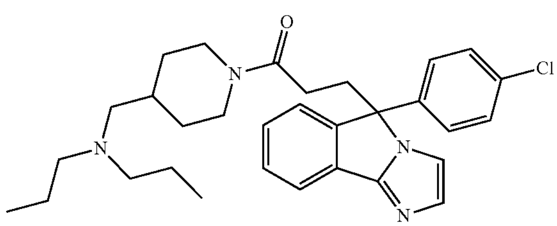 [SMILES: CCCN(CCC)CC1CCN(C(=O)CCC2(c3ccc(Cl)cc3)c3ccccc3-c3nccn32)CC1] | N-[(1-{3-[5-(4-chlorophenyl)-5H-imidazo[2,1-a]isoindol-5-yl]propanoyl}piperidin-4-yl)methyl]-N-propylpropan-1-mine | 519.2882 |
| 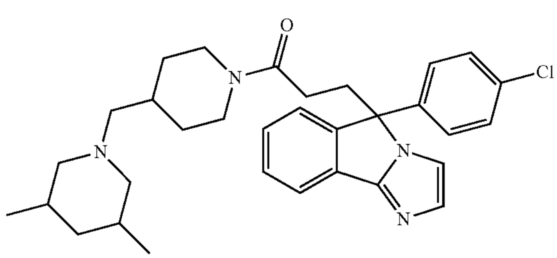 [SMILES: CC1CC(C)CN(CC2CCN(C(=O)CCC3(c4ccc(Cl)cc4)c4ccccc4-c4nccn43)CC2)C1] | 5-(4-chlorophenyl)-5-(3-{4-[(3,5-dimethylpiperidin-1-yl)methyl]piperidin-1-yl}-3-oxopropyl)-5H-imidazo[2,1-a]isoindole | 531.2883 |
| 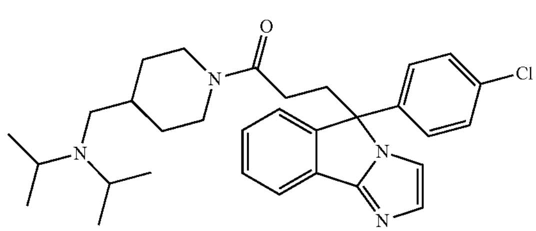 [SMILES: CC(C)N(CC1CCN(C(=O)CCC2(c3ccc(Cl)cc3)c3ccccc3-c3nccn32)CC1)C(C)C] | N-[(1-{3-[5-(4-chlorophenyl)-5H-imidazo[2,1-a]isoindol-5-yl]propanoyl}piperidin-4-yl)methyl]-N-(1-methylethyl)propan-2-amine | 519.2882 |

| STRUCTURE | Chemical name | Mass found |
|---|---|---|
| 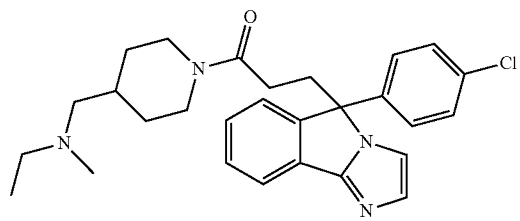 [SMILES: CCN(C)CC1CCN(C(=O)CCC2(c3ccc(Cl)cc3)c3ccccc3-c3nccn32)CC1] | N-[(1-{3-[5-(4-chlorophenyl)-5H-imidazo[2,1-a]isoindol-5-yl]propanoyl}piperidin-4-yl)methyl]-N-methylethanamine | 477.2412 |
| 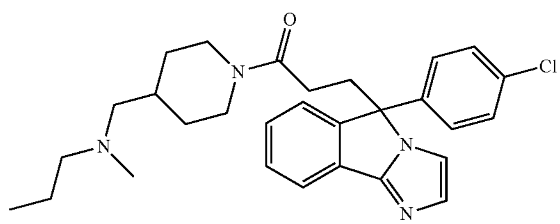 [SMILES: CCCN(C)CC1CCN(C(=O)CCC2(c3ccc(Cl)cc3)c3ccccc3-c3nccn32)CC1] | N-[(1-{3-[5-(4-chlorophenyl)-5H-imidazo[2,1-a]isoindol-5-yl]propanoyl}piperidin-4-yl)methyl]-N-methylpropan-1-amine | 491.2571 |
| 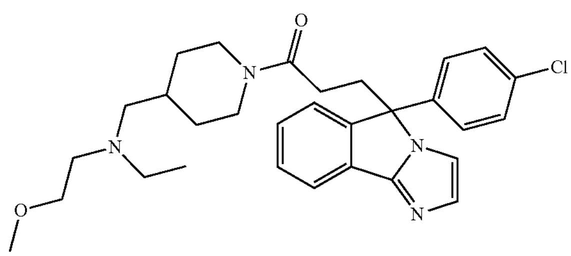 [SMILES: CCN(CCOC)CC1CCN(C(=O)CCC2(c3ccc(Cl)cc3)c3ccccc3-c3nccn32)CC1] | N-[(1-{3-[5-(4-chlorophenyl)-5H-imidazo[2,1-a]isoindol-5-yl]propanoyl}piperidin-4-yl)methyl]-N-ethyl-2-methoxyethanamine | 521.2676 |
| 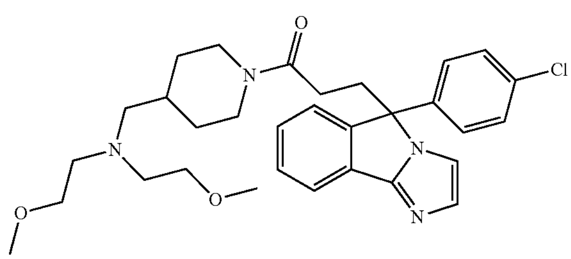 [SMILES: COCCN(CCOC)CC1CCN(C(=O)CCC2(c3ccc(Cl)cc3)c3ccccc3-c3nccn32)CC1] | N-[(1-{3-[5-(4-chlorophenyl)-5H-imidazo[2,1-a]isoindol-5-yl]propanoyl}piperidin-4-yl)methyl]-2-methoxy-N-(2-ethoxy-ethyl)ethanamine | 551.2783 |
| 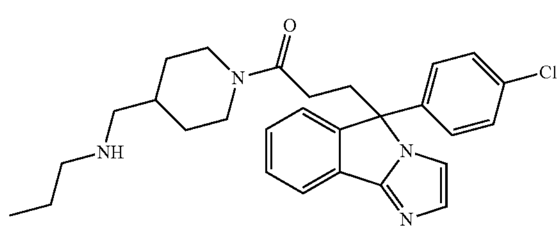 [SMILES: CCCNCC1CCN(C(=O)CCC2(c3ccc(Cl)cc3)c3ccccc3-c3nccn32)CC1] | N-[(1-{3-[5-(4-chlorophenyl)-5H-imidazo[2,1-a]isoindol-5-yl]propanoyl}piperidin-4-yl)methyl]propan-1-amine | 477.2416 |
| 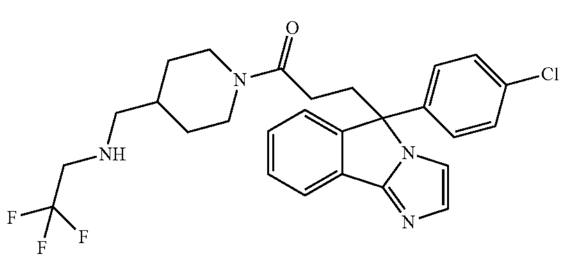 [SMILES: O=C(CCC1(c2ccc(Cl)cc2)c2ccccc2-c2nccn21)N1CCC(CNCC(F)(F)F)CC1] | N-[(1-{3-[5-(4-chlorophenyl)-5H-imidazo[2,1-a]isoindol-5-yl]propanoyl}piperidin-4-yl)methyl]-2,2,2-trifluoroethanamine | 517.1973 |

SCHEME X

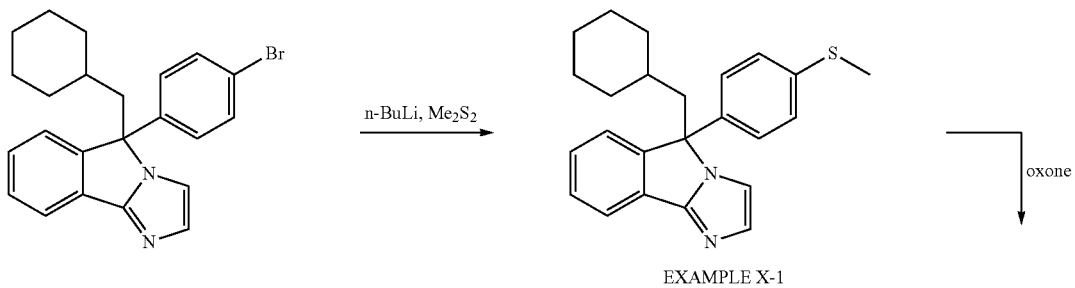

EXAMPLE X-1

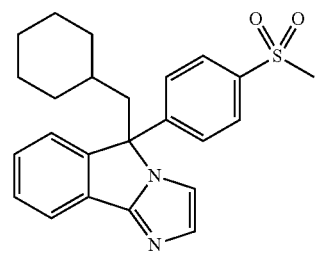

EXAMPLE X-2

EXAMPLES X-1 AND X-2

Step 1, Example X-1: 5-(cyclohexylmethyl)-5-[4-(methylthio)phenyl]-5H-imidazo[2,1-a]isoindole A solution of 5-(4-bromophenyl)-5-(cyclohexylmethyl)-5H-imidazo[2,1-c]isoindole (100 mg) in THF (3 mL) was cooled to −78° C. and n-BuLi solution (0.108 mL, 2.5 M in hexane) was added slowly. After stirring for 15 minutes dimethyl disulfide (35 mg) was added to the resulting red solution. The bath temperature was then slowly raised to −40° C. in ~40 minutes. The reaction was then quenched with aqueous saturated NH$_4$Cl and was partitioned between saturated aqueous NH$_4$Cl and EtOAc. Aqueous layer was extracted with EtOAc (2×). Combined organic layers were dried over Na$_2$SO$_4$ and concentrated. Purification by reversed phase HPLC (21×100 mm Phenomenex Gemini, 5-50% MeCN/water containing 0.1% TFA over 20 min at 20 mL/min) afforded title compound as a white solid. HRMS. Found, 375.1895; calcd for (M+H)$^+$, 375.1890. $^1$H NMR (500 MHz, CDCl$_3$): δ 7.84 (d, J=7.59 Hz, 1 H); 7.39-7.34 (m, 1 H); 7.31 (s, 1 H); 7.27-7.20 (m, 2 H); 7.15 (d, J=8.37 Hz, 2 H); 7.02 (d, J=8.37 Hz, 2 H); 6.98 (s, 1 H); 2.54 (dd, J=14.49, 4.17 Hz, 1 H); 2.43 (s, 3 H); 2.37 (dd, J=14.50, 4.02 Hz, 1 H); 1.51-1.36 (m, 3 H); 1.21 (d, J=12.02 Hz, 1 H); 1.09 (br, 1 H); 1.05-0.91 (m, 2 H); 0.90-0.74 (m, 4 H).

Step 2, Example X-2: 5-(cyclohexylmethyl)-5-[4-(methylsulfonyl)phenyl]-5H-imidazo[2,1-a]isoindole To a solution of 5-(cyclohexylmethyl)-5-[4-(methylthio)phenyl]-5H-imidazo[2,1-a]isoindole (38 mg) in MeOH (1 mL) was added water drop wise until the clear solution started to become turbid. Oxone (69 mg) was added at this time and stirred at room temperature 21 h. The reaction mixture was then diluted with MeOH, filtered and the filtrate was concentrated. Purification by reversed phase HPLC (21×100 mm Phenomenex Gemini, 15-85% MeCN/water containing 0.05% NH$_4$OH over 20 min at 20 mL/min) afforded title compound as a white solid. HRMS. Found, 407.1802; calcd for (M+H)$^+$, 407.1788. $^1$H NMR (500 MHz, CDCl$_3$): δ 7.89-7.85 (m, 3 H); 7.45-7.39 (m, 1 H); 7.37 (d, J=1.28 Hz, 1 H); 7.32-7.26 (m, 3 H); 7.24 (d, J=8.00 Hz, 1 H); 6.99 (d, J=1.29 Hz, 1 H); 3.01 (s, 3 H); 2.60 (dd, J=14.41, 4.34 Hz, 1 H); 2.41 (dd, J=14.40, 4.00 Hz, 1 H); 1.54-1.38 (m, 3 H); 1.33-1.19 (m, 2 H); 1.10-0.73 (m, 7 H).

The following compounds were prepared using the experimental procedure described above for Scheme X.

| STRUCTURE | Chemical name | Mass found |
|---|---|---|
| 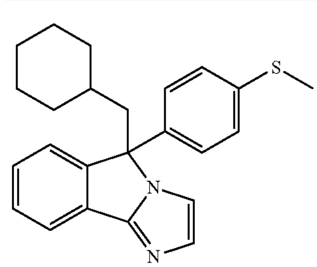 [SMILES: CSc1ccc(C2(CC3CCCCC3)c3ccccc3-c3nccn32)cc1] | 5-(cyclohexylmethyl)-5-[4-(methylsulfanyl)phenyl]-5H-imidazo[2,1-a]isoindole | 375.1895 |
| 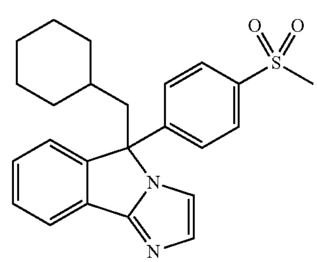 [SMILES: CS(=O)(=O)c1ccc(C2(CC3CCCCC3)c3ccccc3-c3nccn32)cc1] | 5-(cyclohexylmethyl)-5-[4-(methylsulfonyl)phenyl]-5H-imidazo[2,1-a]isoindole | 407.1802 |

SCHEME XI

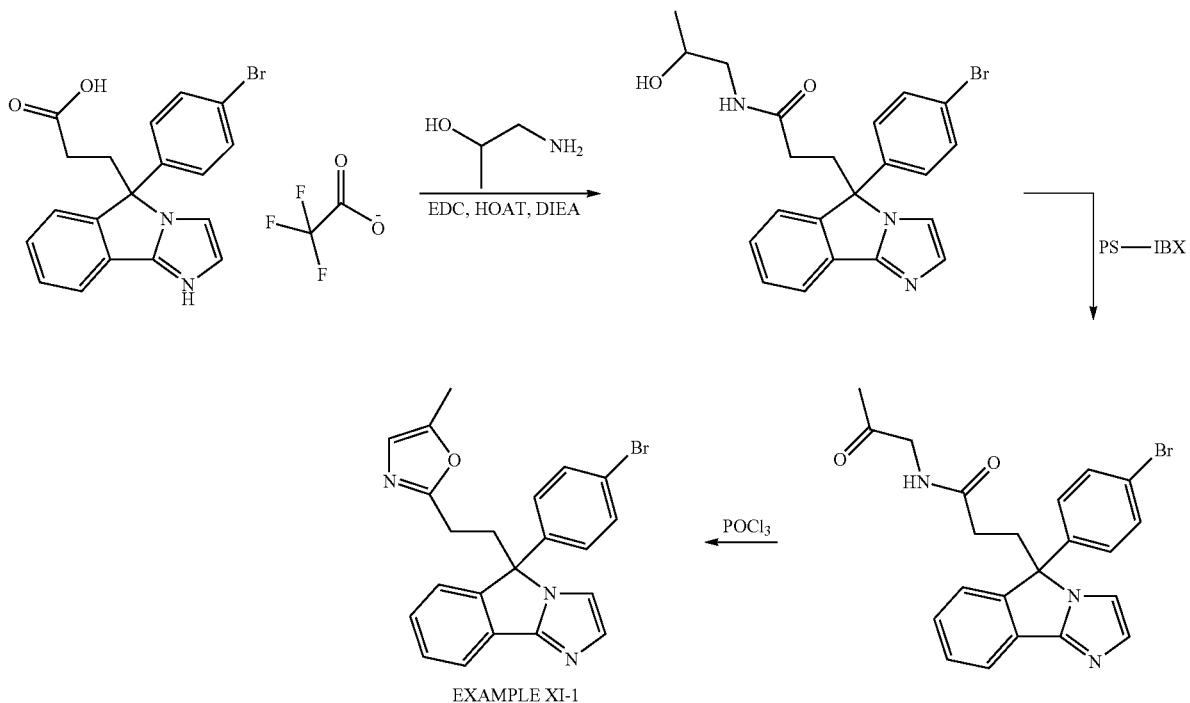

EXAMPLE XI-1

EXAMPLE XI-1

Step 1: 3-[5-(4-bromophenyl)-5H-imidazo[2,1-a]isoindol-5-yl]-N-(2-hydroxypropyl)propanamide To a solution of 5-(4-bromophenyl)-5-(2-carboxyethyl)-5H-imidazo[2,1-c]isoindol-1-ium trifluoroacetate (120 mg) in DMF (0.7 mL) were added EDC (139 mg), HOAT (33 mg), Hunig's base (250 mg) and 1-amino-2-propanol (54 mg). After stirring at 50° C. overnight the mixture was purified by reversed phase HPLC (21×100 mm Phenomenex Gemini, 10-60% MeCN/water containing 0.05% $NH_4OH$ over 20 min at 20 mL/min) to give title compound as a white solid. Mass. found $(M+H)^+$, 442.1.

Step 2: 3-[5-(4-bromophenyl)-5H-imidazo[2,1-c]isoindol-5-yl]-N-(2-oxopropyl)propanamide To a solution of 3-[5-(4-bromophenyl)-5H-imidazo[2,1-c]isoindol-5-yl]-N-(2-hydroxypropyl)propanamide (71 mg) in $CH_2Cl_2$ (2 mL) was added resin (polystyrene) bound IBX (1 equivalent) and allowed to react overnight. THF (2 mL) followed by resin (polystyrene) bound IBX (1 equivalent) were added to the reaction mixture and allowed to react for 24 h. The reaction mixture was then filtered through a fritted funnel and the resin was washed thoroughly with THF. Combined filtrate and washings were concentrated to give the title compound as a white solid. Mass. found $(M+H)^+$, 440.0.

Step 3, Example XI-1: 5-(4-bromophenyl)-5-[2-(5-methyl-1,3-oxazol-2-yl)ethyl]-5H-imidazo[2,1-a]isoindole To a solution of 3-[5-(4-bromophenyl)-5H-imidazo[2,1-c]isoindol-5-yl]-N-(2-oxopropyl)propanamide (67 mg) in pyridine (1 mL) was added $POCl_3$ (0.5 mL). A strong exotherm was observed. The reaction mixture was diluted with EtOAc and aqueous saturated $NaHCO_3$ solution was added to it slowly until the gas evolution stopped. Layers were separated and aqueous layer was extracted with $CH_2Cl_2$ (3×). Combined organic layers were dried over $Na_2SO_4$ and concentrated. Purification by reversed phase HPLC (21×100 mm Phenomenex Gemini, 5-45% MeCN/water containing 0.05% $NH_4OH$ over 20 min at 20 mL/min) to give title compound as a colorless glass. HRMS. Found, 420.0703; calcd for $(M+H)^+$, 420.0706. $^1$H NMR (500 MHz, $CDCl_3$): δ 7.88 (d, J=7.63 Hz, 1 H); 7.47-7.38 (m, 3 H); 7.35 (s, 1 H); 7.29 (t, J=7.76 Hz, 1 H); 7.23 (d, J=7.75 Hz, 1 H); 7.05 (d, J=8.28 Hz, 2 H); 6.99 (s, 1 H); 6.53 (s, 1H); 3.14-3.06 (m, 1 H); 2.98-2.89 (m, 1 H); 2.18 (s, 3 H); 2.14-2.01 (m, 2 H).

The following compound was prepared using the experimental procedure described above for Scheme XI.

| STRUCTURE | Chemical name | Mass found |
|---|---|---|
| 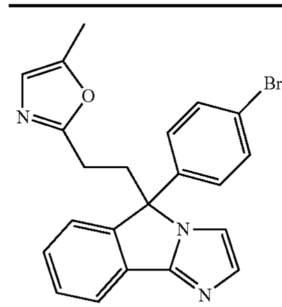 | 5-(4-bromophenyl)-5-[2-(5-methyl-1,3-oxazol-2-yl)ethyl]-5H-imidazo[2,1-a]isoindole | 420.0703 |

SCHEME XII

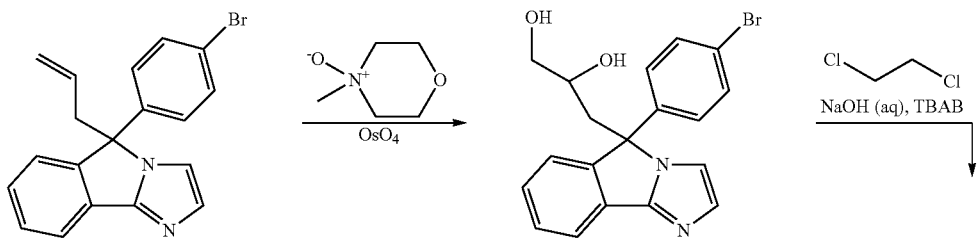

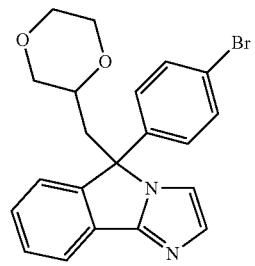 [SMILES: Brc1ccc(C2(CC3COCCO3)c3ccccc3-c3nccn32)cc1]

EXAMPLE XII-1

EXAMPLE XII-1

Step 1: 3-[5-(4-bromophenyl)-5H-imidazo[2,1-a]isoindol-5-yl]propane-1,2-diol To a solution of 5-allyl-5-(4-bromophenyl)-5H-imidazo[2,1-a]isoindole (150 mg) in acetone (5.5 mL) was added water (1 mL) followed by NMO (60 mg) and $OsO_4$ (0.536 mL, 2.5% in tert-BuOH). After stirring at room temperature for 24 h, 100 mg NMO and 0.1 mL $OsO_4$ solution were added. After 9 h 0.1 mL more $OsO_4$ solution was added and stirred at room temperature over the weekend. The reaction was then quenched with 1:1 aqueous saturated $NaHCO_3$:$Na_2SO_3$ and partitioned between aqueous saturated $NaHCO_3$ and EtOAc. Aqueous layer was extracted with EtOAc (3×). Combined organic layers were dried over $Na_2SO_4$ and concentrated. Purification by reversed phase HPLC (21×100 mm Phenomenex Gemini, 5-40% MeCN/water containing 0.1% TFA over 20 min at 20 mL/min) to give title compound as a white solid. Mass. found (M+H)$^+$, 387.0.

Step 2, Example XII-1: 5-(4-bromophenyl)-5-(1,4-dioxan-2-ylmethyl)-5H-imidazo[2,1-a]isoindole To a mixture of 3-[5-(4-bromophenyl)-5H-imidazo[2,1-a]isoindol-5-yl]propane-1,2-diol (30 mg) and tetrabutylammonium bromide (30 mg) in 1,2-dichloroethane (1.125 mL) was added aqueous NaOH (35%, 1.5 mL) and heated at 55° C. for 17 h. After cooling to room temperature the reaction mixture was diluted with water and extracted with $CH_2Cl_2$ (3×). Combined organic layers were dried over $Na_2SO_4$ and concentrated. Purification by reversed phase HPLC (21×100 mm Phenomenex Gemini, 15-75% MeCN/water containing 0.05% $NH_4OH$ over 20 min at 20 mL/min) to give title compound as a slightly impure solid which was then repurified by flash chromatography using EtOAc as eluent to give desired product as a white solid. HRMS. Found, 411.0681; calcd for (M+H)$^+$, 411.0703. $^1$H NMR (500 MHz, CDCl$_3$): δ 7.89-7.83 (m, 2 H); 7.45-7.26 (m, 5 H); 7.15 (d, J=7.71 Hz, 0.5 H); 7.02 (s, 0.5 H); 7.00-6.92 (m, 3 H); 3.53-3.40 (m, 3 H); 3.36-2.97 (m, 4 H); 2.76 (dd, J=14.88, 5.92 Hz, 0.5H); 2.68 (dd, J=14.78, 5.44 Hz, 0.5 H); 2.47 (ddd, J=29.48, 14.82, 4.79 Hz, 1 H).

The following compound was prepared using the experimental procedure described above for Scheme XII.

| STRUCTURE | Chemical name | Mass found |
|---|---|---|
| 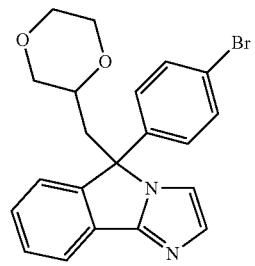 [SMILES: Brc1ccc(C2(CC3COCCO3)c3ccccc3-c3nccn32)cc1] | 5-(4-bromophenyl)-5-(1,4-dioxan-2-ylmethyl)-5H-imidazo[2,1-a]isoindole | 411.0681 |

SCHEME XIII

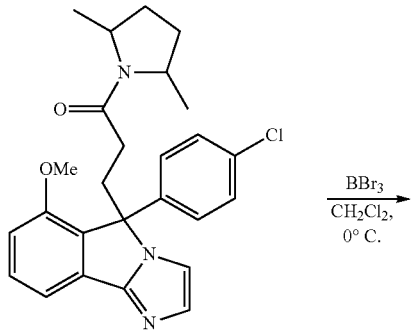 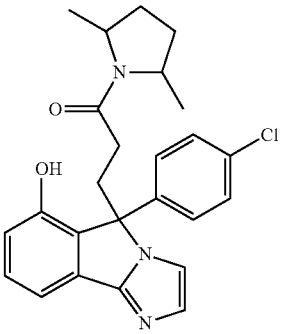 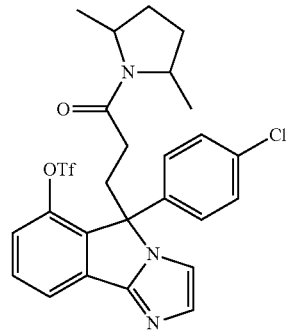

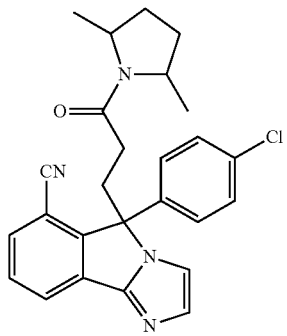

EXAMPLE XIII-2

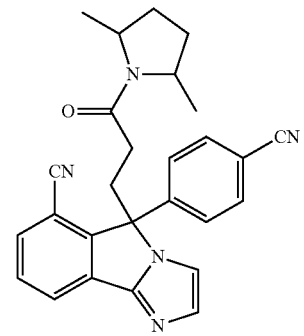

EXAMPLE XIII-1

EXAMPLES XIII-1 AND XIII-2

Step 1: 5-(4-chlorophenyl)-5-[3-(2,5-dimethylpyrrolidin-1-yl)-3-oxopropyl]-5H-imidazo[2,1-a]isoindol-6-ol To a solution of 5-(4-chlorophenyl)-5-[3-(2,5-dimethylpyrrolidin-1-yl)-3-oxopropyl]-6-methoxy-5H-imidazo[2,1-a]isoindole (190 mg) in $CH_2Cl_2$ (2 mL) was added $BBr_3$ (1.7 ml) slowly at 0° C. After 90 min the mixture was quenched with saturated aqueous $NaHCO_3$. The layers were separated and the aqueous layer was extracted with $CH_2Cl_2$ (3×). The combined organic layers were dried ($Na_2SO_4$), filtered, and concentrated to an off-white solid (179 mg) which was sufficiently pure for use in the next step.

Step 2: 5-(4-chlorophenyl)-5-[3-(2,5-dimethylpyrrolidin-1-yl)-3-oxopropyl]-5H-imidazo[2,1-a]isoindol-6-yl trifluoromethanesulfonate To a solution of crude 5-(4-chlorophenyl)-5-[3-(2,5-dimethylpyrrolidin-1-yl)-3-oxopropyl]-5H-imidazo[2,1-a]isoindol-6-ol (179 mg) in $CH_2Cl_2$ (2 mL) was added DIEA (0.108 ml) then N-phenyl bis(trifluoromethanesulfonimide (220 mg) at room temperature. After 18 h the mixture was concentrated. Flash column chromatography (90% EtOAc/hexanes) gave an off-white foam (256 mg) which was sufficiently pure for use in the next step: $^1$H-NMR (500 MHz, CDCl$_3$) δ 7.87 (d, J=7.57 Hz, 1 H), 7.55 (t, J=7.57 Hz, 1 H), 7.31-7.14 (m, 5 H), 7.10 (m, 1 H), 6.90 (d, J=12.75 Hz, 1 H), 3.92 (m, 1 H), 3.65 (m, 1 H), 3.46-3.02 (m, 2 H), 1.95 (m, 1 H), 1.82-1.72 (m, 2 H), 1.52 (m, 2 H), 1.35 (t, J=7.57 Hz, 1 H), 1.18 (t, J=6.59 Hz, 3 H), 0.86 (m, 3 H).

Step 3, Examples XIII-1 and XIII-2: 5-(4-cyanophenyl)-5-[3-(2,5-dimethylpyrrolidin-1-yl)-3-oxopropyl]-5H-imidazo[2,1-a]isoindole-6-carbonitrile and 5-(4-chlorophenyl)-5-[3-(2,5-dimethylpyrrolidin-1-yl)-3-oxopropyl]-5H-imidazo[2,1-a]isoindole-6-carbonitrile 5-(4-chlorophenyl)-5-[3-(2,5-dimethylpyrrolidin-1-yl)-3-oxopropyl]-5H-imidazo[2,1-a]isoindol-6-yl trifluoromethanesulfonate (50 mg), Pd$_2$(dba)$_3$ (8 mg), DPPF (10 mg), zinc powder (0.3 mg), and Zn(CN)$_2$ (21 mg) were combined in DMA (0.5 mL). The mixture was degassed (3× pump/N$_2$) then heated to 120° C. After 3 h the mixture was cooled to room temperature. The mixture was filtered using a 0.45 μm PTFE syringe filter then purified by preparative reversed-phase HPLC (21×100 mm Phenomenex Gemini, 5-95% ACN/water containing 0.05% NH$_4$OH over 20 min at 20 mL/min) to give 5-(4-cyanophenyl)-5-[3-(2,5-dimethylpyrrolidin-1-yl)-3-oxopropyl]-5H-imidazo[2,1-a]isoindole-6-carbonitrile as a light tan solid (3.7 mg): $^1$H-NMR (400 MHz, CDCl$_3$) δ 8.01 (d, J=7.05 Hz, 1 H), 7.64 (d, J=8.51 Hz, 1H), 7.56 (m, 2 H), 7.35 (d, J=8.42 Hz, 1 H), 7.30 (dd, J=2.56 and 5.95 Hz, 2 H), 6.94 (d, J=9.34 Hz, 1 H), 3.88 (m, 1 H), 3.58 (m, 1 H), 3.36 (m, 1 H), 3.15 (m, 1 H), 1.98-1.48 (m, 6 H), 1.16 (dd, J=6.32 and 8.24 Hz, 3 H), 0.87 (t, J=6.05 Hz, 3 H); HRMS (M+H)$^+$ calculated 436.2132. found 436.2135 and 5-(4-chlorophenyl)-5-[3-(2,5-dimethylpyrrolidin-1-yl)-3-oxopropyl]-5H-imidazo[2,1-a]isoindole-6-carbonitrile as a light tan solid (16 mg): $^1$H-NMR (400 MHz, CDCl$_3$) δ 8.08 (dd, J=2.2 and 2.84 Hz, 1 H), 7.54 (m, 2 H), 7.30 (m, 3 H), 7.10 (dd, J=2.75 and 6.04 Hz, 2 H), 6.94 (d, J=9.25 Hz, 1 H), 3.89 (m, 1 H), 3.55-3.33 (m, 2 H), 3.19-3.07 (m, 1 H), 1.94 (m, 1 H), 1.82 (m, 1 H), 1.70 (m, 1 H), 1.52 (m, 1 H), 1.17 (dd, J=6.32 and 5.40 Hz, 3 H), 0.87 (t, J=4.86 Hz, 3 H); HRMS (M+H)$^+$ calculated 445.1790. found 445.1791.

The following compounds were prepared using the experimental procedure described above for Scheme XIII.

| STRUCTURE | Chemical name | Mass found |
|---|---|---|
| 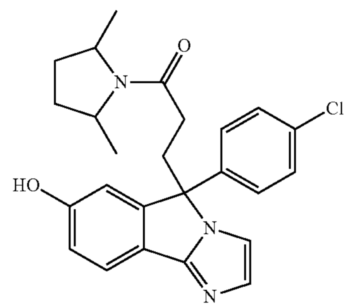 [SMILES: CC1CCC(C)N1C(=O)CCC1(c2ccc(Cl)cc2)c2cc(O)ccc2-c2nccn21] | 5-(4-chlorophenyl)-5-[3-(2,5-dimethylpyrrolidin-1-yl)-3-oxopropyl]-5H-imidazo[2,1-a]isoindol-7-ol | 436.1778 |
| 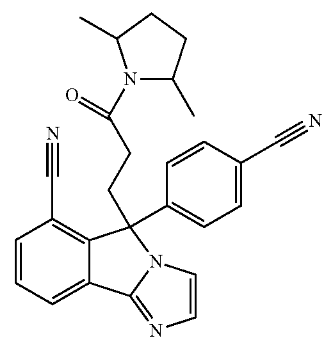 [SMILES: CC1CCC(C)N1C(=O)CCC1(c2ccc(C#N)cc2)c2c(C#N)cccc2-c2nccn21] | 5-(4-cyanophenyl)-5-[3-(2,5-dimethylpyrrolidin-1-yl)-3-oxopropyl]-5H-imidazo[2,1-a]isoindol-6-carbonitrile | 436.2135 |
| 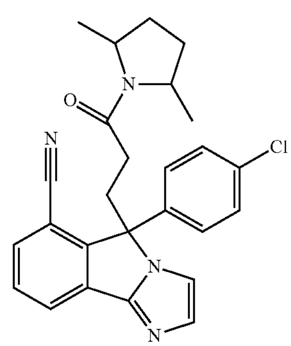 [SMILES: CC1CCC(C)N1C(=O)CCC1(c2ccc(Cl)cc2)c2c(C#N)cccc2-c2nccn21] | 5-(4-chlorophenyl)-5-[3-(2,5-dimethylpyrrolidin-1-yl)-3-oxopropyl]-5H-imidazo[2,1-a]isoindol-6-carbonitrile | 445.1791 |
| 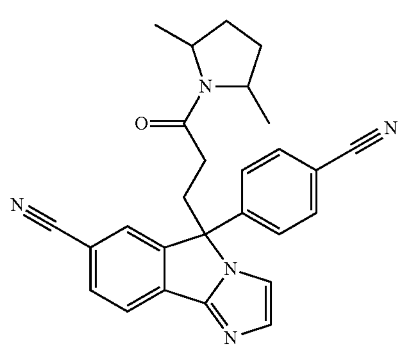 [SMILES: CC1CCC(C)N1C(=O)CCC1(c2ccc(C#N)cc2)c2cc(C#N)ccc2-c2nccn21] | 5-(4-cyanophenyl)-5-[3-(2,5-dimethylpyrrolidin-1-yl)-3-oxopropyl]-5H-imidazo[2,1-a]isoindol-7-carbonitrile | 436.2133 |

| STRUCTURE | Chemical name | Mass found |
|---|---|---|
| 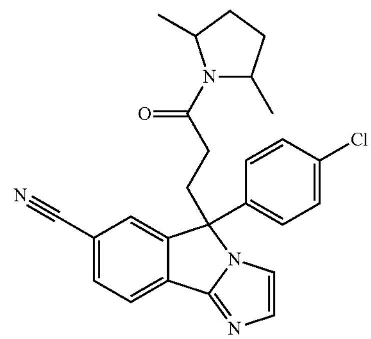 [SMILES: CC1CCC(C)N1C(=O)CCC1(c2ccc(Cl)cc2)c2cc(C#N)ccc2-c2nccn21] | 5-(4-chlorophenyl)-5-[3-(2,5-dimethylpyrrolidin-1-yl)-3-oxopropyl]-5H-imidazo[2,1-a]isoindol-7-carbonitrile | 445.1791 |
| 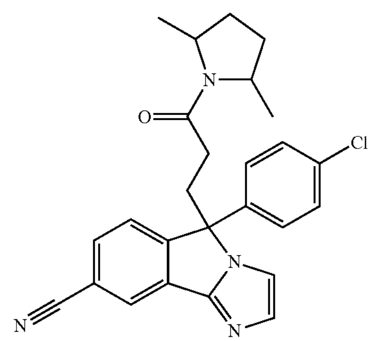 [SMILES: CC1CCC(C)N1C(=O)CCC1(c2ccc(Cl)cc2)c2ccc(C#N)cc2-c2nccn21] | 5-(4-chlorophenyl)-5-[3-(2,5-dimethylpyrrolidin-1-yl)-3-oxopropyl]-5H-imidazo[2,1-a]isoindol-8-carbonitrile | 445.1792 |

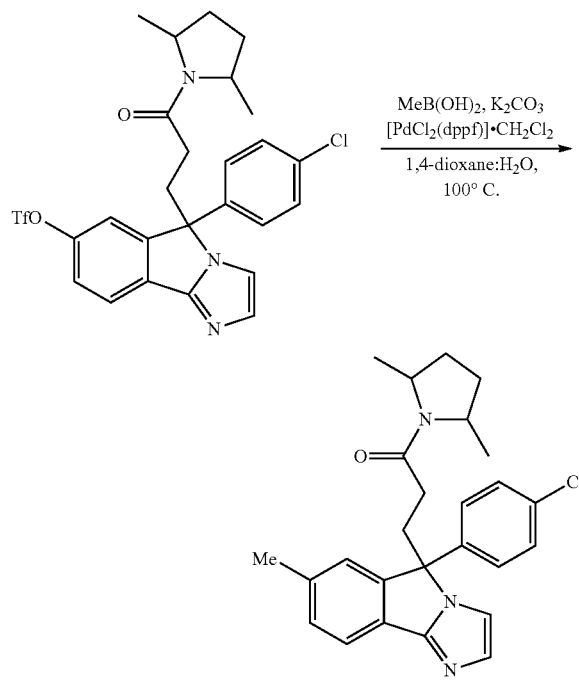

SCHEME XIV

EXAMPLE XIV-1

Example XIV-1

Step 1, Example XIV-1: 5-(4-chlorophenyl)-5-[3-(2,5-dimethylpyrrolidin-1-yl)-3-oxopropyl]-7-methyl-5H-imidazo[2,1-a]isoindole 5-(4-chlorophenyl)-5-[3-(2,5-dimethylpyrrolidin-1-yl)-3-oxopropyl]-5H-imidazo[2,1-a]isoindol-7-yl trifluoromethanesulfonate (50 mg), methylboronic acid (8 mg), $K_2CO_3$ (37 mg), and $PdCl_2(dppf)\cdot CH_2Cl_2$ adduct (8 mg) were combined in 1,4-dioxane (400 μL):$H_2O$ (40.0 μL). The mixture was degassed (3× pump/$N_2$) then heated to 100° C. After 3 h the mixture was cooled to room temperature and concentrated. The residue was taken up in DMF, filtered using a 0.45 μm PTFE syringe filter, then purified by preparative reversed-phase HPLC (21×100 mm Phenomenex Gemini (5-95% ACN/water containing 0.05% $NH_4OH$ over 20 min at 20 mL/min) to give a light grey solid (16 mg): $^1$H-NMR (400 MHz, $CDCl_3$) δ 7.71 (d, J=7.79 Hz, 1 H), 7.27 (m, 3 H), 7.19 (m, 1 H), 7.12 (dd, J=3.66 and 5.04 Hz, 2 H), 7.03 (bs, 1 H), 6.93 (dd, J=1.19 and 7.88 Hz, 1 H), 3.89 (m, 1 H), 3.41 (m, 1 H), 3.20-2.75 (m, 2 H), 2.34 (d, J=2.74 Hz, 3 H), 1.97-1.63 (m, 2 H), 1.50 (m, 4 H), 1.17 (dd, J=6.32 and 8.43 Hz, 3 H), 0.86 (dd, J=6.50 and 27.1 Hz, 3 H); HRMS (M+H)$^+$ calculated 434.1994. found 434.1993.

The following compounds were prepared using the experimental procedure described above for Scheme XIV.

| STRUCTURE | Chemical name | Mass found |
|---|---|---|
| 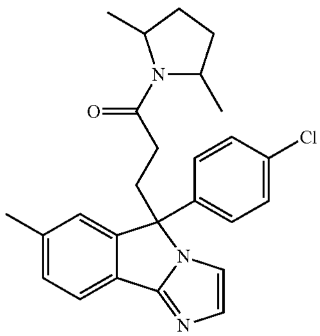 [SMILES: Cc1ccc2c(c1)C(CCC(=O)N1C(C)CCC1C)(c1ccc(Cl)cc1)n1ccnc1-2] | 5-(4-chlorophenyl)-5-[3-(2,5-dimethylpyrrolidin-1-yl)-3-oxopropyl]-7-methyl-5H-imidazo[2,1-a]isoindole | 434.1993 |
| 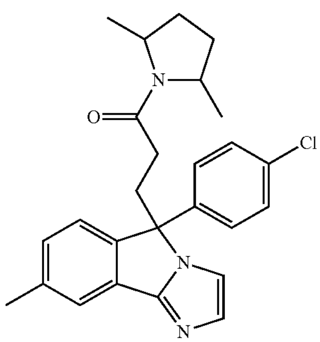 [SMILES: Cc1ccc2c(c1)-c1nccn1C2(CCC(=O)N1C(C)CCC1C)c1ccc(Cl)cc1] | 5-(4-chlorophenyl)-5-[3-(2,5-dimethylpyrrolidin-1-yl)-3-oxopropyl]-8-methyl-5H-imidazo[2,1-a]isoindole | 434.1992 |
SCHEME XV
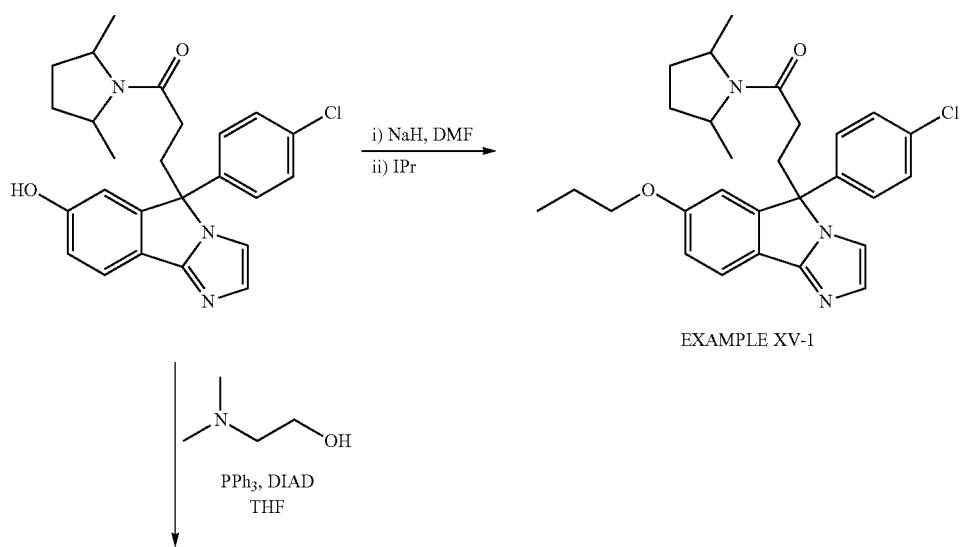
EXAMPLE XV-1

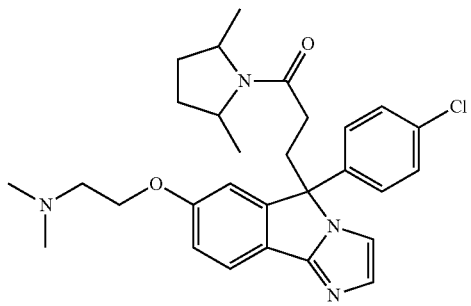

EXAMPLE XV-2

EXAMPLES XV-1 AND XV-2

Step 1, Example XV-1: 5-(4-chlorophenyl)-5-[3-(2,5-dimethylpyrrolidin-1-yl)-3-oxopropyl]-7-propoxy-5H-imidazo[2,1-c]isoindole To a solution of 5-(4-chlorophenyl)-5-[3-(2,5-dimethylpyrrolidin-1-yl)-3-oxopropyl]-5H-imidazo[2,1-a]isoindol-7-ol (30 mg) in dry DMF (0.5 mL) was added NaH (4 mg, 60% dispersion in mineral oil) at room temperature. After 15 min 1-iodopropane (10 µL) was added and stirring continued. After 2 h the mixture was filtered using a 0.45 µm PTFE syringe filter then purified by preparative reversed-phase HPLC (20×150 mm Waters Sunfire, 5-60% ACN/water containing 0.1% TFA over 20 min. at 20 mL/min). Fractions containing the product were pooled then passed through Dowex 1×2-400 ion exchange resin (prewashed with 1M NaOH, H$_2$O, MeOH) washing with MeOH. The filtrate was concentrated to give a white solid (22 mg): $^1$H-NMR (500 MHz, CDCl$_3$) δ 7.73 (d, J=8.30 Hz, 1 H), 7.29-7.24 (m, 3 H), 7.13 (m, 2 H), 6.90 (dd, J=1.22 and 9.76 Hz, 2 H), 6.74 (m, 1 H), 3.89 (m, 3 H), 3.40 (m, 1 H), 3.15-2.78 (m, 2 H), 1.95 (m, 1 H), 1.90-1.49 (m, 5 H), 1.78 (q, J=7.32 Hz, 2 H), 1.19 (dd, J=6.11 and 11.96 Hz, 3 H), 1.02 (t, J=7.33 Hz, 3 H), 0.86 (dd, J=6.49 and 28.57 Hz, 3 H); HRMS (M+H)$^+$ calculated 478.2256. found 478.2240.

Step 2, Example XV-2: 2-({5-(4-chlorophenyl)-5-[3-(2,5-dimethylpyrrolidin-1-yl)-3-oxopropyl]-5H-imidazo[2,1-a]isoindol-7-yl}oxy)-N,N-dimethylethanamine To a solution of 5-(4-chlorophenyl)-5-[3-(2,5-dimethylpyrrolidin-1-yl)-3-oxopropyl]-5H-imidazo[2,1-a]isoindol-7-ol (30 mg) in dry THF (0.5 mL) was added triphenylphosphine (27 mg), 2-dimethylaminoethanol (11 µL), then DIAD (21 µL) at room temperature. After 3 h additional triphenylphosphine (27 mg), 2-dimethylaminoethanol (11 µL), and DIAD (21 µL) were added and stirring continued. After 24 h the mixture was concentrated. The crude material was purified by preparative reversed-phase HPLC (20×150 mm Waters Sunfire, 5-50% ACN/water containing 0.1% TFA over 20 min. at 20 mL/min). Fractions containing the product were pooled then passed through Dowex 1×2-400 ion exchange resin (prewashed with 1M NaOH, H$_2$O, MeOH) washing with MeOH. The filtrate was concentrated to give a white solid (20 mg): $^1$H-NMR (500 MHz, CDCl$_3$) δ 7.73 (dd, J=2.2 and 6.1 Hz, 1 H), 7.29-7.24 (m, 3 H), 7.12 (m, 2 H), 6.93 (m, 2 H), 6.78 (dd, J=2.2 and 3.9 Hz, 1 H), 4.04-3.90 (m, 3 H), 3.40 (m, 1 H), 3.11-2.79 (m, 2 H), 2.69 (t, J=5.37 Hz, 1 H), 2.32 (s, 6 H), 2.02-1.75 (m, 2 H), 1.66-1.49 (m, 5 H), 1.16 (dd, J=6.35 and 11.96 Hz, 3 H), 0.88 (dd, J=6.32 and 27.1 Hz, 3 H); HRMS (M+H)$^+$ calculated 507.2521. found 507.2508.

The following compounds were prepared using the experimental procedure described above for Scheme XV.

| STRUCTURE | Chemical name | Mass found |
|---|---|---|
| 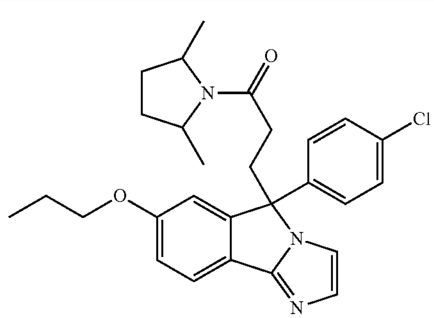 [SMILES: CCCOc1ccc2c(c1)C(CCC(=O)N1C(C)CCC1C)(c1ccc(Cl)cc1)n1ccnc1-2] | 5-(4-chlorophenyl)-5-[3-(2,5-dimethylpyrrolidin-1-yl)-3-oxopropyl]-7-propoxy-5H-imidazo[2,1-a]isoindole | 478.224 |

| STRUCTURE | Chemical name | Mass found |
|---|---|---|
| 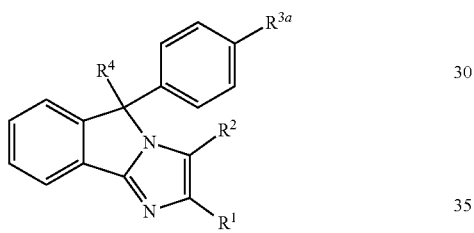 | 2-({5-(4-chlorophenyl)-5-[3-(2,5-dimethylpyrrolidin-1-yl)-3-oxopropyl]-5H-imidazo[2,1-a]isoindole-7-yl}oxy)-N,N-dimethylethanamine | 507.2508 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

The invention claimed is:

1. A compound of the formula:

wherein:
$R^1$ is hydrogen or $C_{1-6}$alkyl;
$R^2$ is hydrogen or $C_{1-6}$alkyl;
$R^{3a}$ is selected from the group consisting of:
 (1) hydrogen,
 (2) halogen,
 (3) —CN, and
 (4) $C_{1-6}$alkyl;
$R^4$ is selected from the group consisting of:
 (1) —CH$_2$CH$_2$—(C=O)-heterocycle, where the heterocycle is unsubstituted or substituted with one or more substituents selected from $R^{13}$, and
 (2) —CH$_2$CH$_2$—(C=O)—NR$^{15}$R$^{16}$, where $R^{15}$ and $R^{16}$ are independently selected from hydrogen and —C$_{1-6}$alkyl, which is unsubstituted or substituted with phenyl;
$R^{13}$ is selected from the group consisting of:
 (1) halogen,
 (2) hydroxyl,
 (3) —(C=O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from $R^{14}$,
 (4) —O$_n$—(C$_{1-3}$)perfluoroalkyl,
 (5) —(C=O)$_m$—O$_n$C$_{3-6}$cycloalkyl, where the cycloalkyl is unsubstituted or substituted with one or more substituents selected from $R^{14}$,
 (6) —(C=O)$_m$—C$_{2-4}$alkenyl, where the alkenyl is unsubstituted or substituted with one or more substituents selected from $R^{14}$,
 (7) —(C=O)$_m$—C$_{2-4}$alkynyl, where the alkenyl is unsubstituted or substituted with one or more substituents selected from $R^{14}$,
 (8) —(C=O)$_m$—O$_n$-phenyl or —(C=O)$_m$—O$_n$-napthyl, where the phenyl or is unsubstituted or substituted with one or more substituents selected from $R^{14}$,
 (9) —(C=O)$_m$—O$_n$-heterocycle, where the heterocycle is unsubstituted or substituted with one or more substituents selected from $R^{14}$,
 (10) —(C=O)$_m$—NR$^{15}$R$^{16}$,
 (11) —S(O)$_2$—NR$^{15}$R$^{16}$,
 (12) —S(O)$_q$—R$^{17}$, where q is 0, 1 or 2 and where $R^{17}$ is —C$_{1-6}$alkyl, which is unsubstituted or substituted with phenyl;
 (13) —CO$_2$H
 (14) —CN, and
 (15) —NO$_2$;
$R^{14}$ is selected from the group consisting of:
 (1) hydroxyl,
 (2) halogen,
 (3) C$_{1-6}$alkyl,
 (4) —C$_{3-6}$cycloalkyl,
 (5) —O—C$_{1-6}$alkyl,
 (6) —O(C=O)—C$_{1-6}$alkyl,
 (7) —NH—C$_{1-6}$ alkyl,
 (8) phenyl,
 (9) heterocycle,
 (10) —CO$_2$H, and
 (11) —CN;
or a pharmaceutically acceptable salt thereof.

2. The compound of claim 1 wherein $R^1$ is hydrogen and $R^2$ is hydrogen.

3. A compound which is selected from the group consisting of:
 5-(4-bromophenyl)-5-[3-(2,5-dimethylpyrrolidin-1-yl)-3-oxopropyl]-2-methyl-5H-imidazo[2,1-a]isoindole;
 5-(4-bromophenyl)-5-[3-(2,5-dimethylpyrrolidin-1-yl)-3-oxopropyl]-3-methyl-5H-imidazo[2,1-a]isoindole;
 5-(4-bromophenyl)-5-[3-(2,5-dimethylpyrrolidin-1-yl)-3-oxopropyl]-2-ethyl-5H-imidazo[2,1-a]isoindole;
 5-(4-bromophenyl)-5-[3-(2,5-dimethylpyrrolidin-1-yl)-3-oxopropyl]-3-ethyl-5H-imidazo[2,1-a]isoindole;
 5-(4-bromophenyl)-2-methyl-5-{3-oxo-3-[4-(1-pyrrolidin-1-ylethyl)piperidin-1-yl]propyl}-5H-imidazo[2,1-a]isoindole;
 5-(4-bromophenyl)-3-methyl-5-{3-oxo-3-[4-(1-pyrrolidin-1-ylethyl)piperidin-1-yl]propyl}-5H-imidazo[2,1-a]isoindole;

5-(4-chlorophenyl)-5-[3-(2,5-dimethylpyrrolidin-1-yl)-3-oxopropyl]-5H-imidazo[2,1-a]isoindol-7-ol;

5-(4-chlorophenyl)-5-[3-(2,5-dimethylpyrrolidin-1-yl)-3-oxopropyl]-2-(trifluoromethyl)-5H-imidazo[2,1-a]isoindole;

5-(4-chlorophenyl)-5-{3-oxo-3-[4-(1-pyrrolidin-1-ylethyl)piperidin-1-yl]propyl}-2-(trifluoromethyl)-5H-imidazo[2,1-a]isoindole;

5-(4-chlorophenyl)-5-[3-(2,5-dimethylpyrrolidin-1-yl)-3-oxopropyl]-6-methoxy-5H-imidazo[2,1-a]isoindole;

5-(4-chlorophenyl)-5-[3-(2,5-dimethylpyrrolidin-1-yl)-3-oxopropyl]-8-methoxy-5H-imidazo[2,1-a]isoindole;

5-(4-chlorophenyl)-5-[3-(2,5-dimethylpyrrolidin-1-yl)-3-oxopropyl]-9-methoxy-5H-imidazo[2,1-a]isoindole;

3-[5-(4-chlorophenyl)-6-methoxy-5H-imidazo[2,1-a]isoindol-5-yl]-N,N-diethylpropanamide;

2-[5-(4-bromophenyl)-5H-imidazo[2,1-a]isoindol-5-yl]-N,N-diethylacetamide;

5-(4-bromophenyl)-5-[2-(4,4-dimethylpiperidin-1-yl)-2-oxoethyl]-5H-imidazo[2,1-a]isoindole;

5-(4-bromophenyl)-5-{2-oxo-2-[4-(1H-pyrazol-4-yl)piperidin-1-yl]ethyl}-5H-imidazo[2,1-a]isoindole;

5-(4-bromophenyl)-5-[2-oxo-2-(4-phenylpiperidin-1-yl)ethyl]-5H-imidazo[2,1-a]isoindole;

5-{2-[(1s,4s)-7-azabicyclo[2.2.1]hept-7-yl]-2-oxoethyl}-5-(4-bromophenyl)-5H-imidazo[2,1-a]isoindole;

5-(4-bromophenyl)-5-[2-(hexahydrofuro[3,2-b]pyridin-4(2H)-yl)-2-oxoethyl]-5H-imidazo[2,1-a]isoindole;

5-(4-bromophenyl)-5-[2-(3,3-difluoropyrrolidin-1-yl)-2-oxoethyl]-5H-imidazo[2,1-a]isoindole;

5-(4-bromophenyl)-5-[2-(4,4-difluoropiperidin-1-yl)-2-oxoethyl]-5H-imidazo[2,1-a]isoindole;

5-(4-bromophenyl)-5-[2-(4-fluoropiperidin-1-yl)-2-oxoethyl]-5H-imidazo[2,1-a]isoindole;

5-(4-bromophenyl)-5-[2-oxo-2-(4-pyridin-4-ylpiperidin-1-yl)ethyl]-5H-imidazo[2,1-a]isoindole;

5-(4-bromophenyl)-5-[2-(2-ethylpiperidin-1-yl)-2-oxoethyl]-5H-imidazo[2,1-a]isoindole;

5-(4-bromophenyl)-5-[2-(3-methylpiperidin-1-yl)-2-oxoethyl]-5H-imidazo[2,1-a]isoindole;

5-(4-bromophenyl)-5-[2-(3,3-dimethylpiperidin-1-yl)-2-oxoethyl]-5H-imidazo[2,1-a]isoindole;

5-(4-bromophenyl)-5-[2-(3,4-dihydroisoquinolin-2(1H)-yl)-2-oxoethyl]-5H-imidazo[2,1-a]isoindole;

5-[2-(2-benzylpyrrolidin-1-yl)-2-oxoethyl]-5-(4-bromophenyl)-5H-imidazo[2,1-a]isoindole;

5-[2-(2-azaspiro[4.4]non-2-yl)-2-oxoethyl]-5-(4-bromophenyl)-5H-imidazo[2,1-a]isoindole;

5-(4-bromophenyl)-5-[2-oxo-2-(2-phenylpyrrolidin-1-yl)ethyl]-5H-imidazo[2,1-a]isoindole;

2-[5-(4-bromophenyl)-5H-imidazo[2,1-a]isoindol-5-yl]-N-(3-hydroxy-1,1-dimethylbutyl)acetamide;

2-[5-(4-bromophenyl)-5H-imidazo[2,1-a]isoindol-5-yl]-N-pyridin-2-ylacetamide;

2-[5-(4-bromophenyl)-5H-imidazo[2,1-a]isoindol-5-yl]-N-cyclohexyl-N-methylacetamide;

2-[5-(4-bromophenyl)-5H-imidazo[2,1-a]isoindol-5-yl]-N-ethyl-N-(1-methylethyl)acetamide;

5-(4-bromophenyl)-5-[2-(octahydroquinolin-1(2H)-yl)-2-oxoethyl]-5H-imidazo[2,1-a]isoindole;

5-(4-bromophenyl)-5-[2-(3,5-dimethylpiperidin-1-yl)-2-oxoethyl]-5H-imidazo[2,1-a]isoindole;

5-(4-bromophenyl)-5-(2-oxo-2-pyrrolidin-1-ylethyl)-5H-imidazo[2,1-a]isoindole;

5-(4-bromophenyl)-5-(3-oxo-3-piperidin-1-ylpropyl)-5H-imidazo[2,1-a]isoindole;

5-(4-bromophenyl)-5-(3-oxo-3-pyrrolidin-1-ylpropyl)-5H-imidazo[2,1-a]isoindole;

3-[5-(4-bromophenyl)-5H-imidazo[2,1-a]isoindol-5-yl]-N-cyclopropylpropanamide;

3-[5-(4-bromophenyl)-5H-imidazo[2,1-a]isoindol-5-yl]-N,N-diethylpropanamide;

5-(4-bromophenyl)-5-[3-(3,3-dimethylpiperidin-1-yl)-3-oxopropyl]-5H-imidazo[2,1-a]isoindole;

5-(4-bromophenyl)-5-{3-oxo-3-[4-(1H-pyrazol-4-yl)piperidin-1-yl]propyl}-5H-imidazo[2,1-a]isoindole;

5-(4-bromophenyl)-5-[3-oxo-3-(4-phenylpiperidin-1-yl)propyl]-5H-imidazo[2,1-a]isoindole;

5-(4-bromophenyl)-5-[3-oxo-3-(4-pyridin-4-ylpiperidin-1-yl)propyl]-5H-imidazo[2,1-a]isoindole;

5-(4-bromophenyl)-5-[3-(2-ethylpiperidin-1-yl)-3-oxopropyl]-5H-imidazo[2,1-a]isoindole;

5-(4-bromophenyl)-5-[3-oxo-3-(2-propylpiperidin-1-yl)propyl]-5H-imidazo[2,1-a]isoindole;

5-(4-bromophenyl)-5-[3-(3-methylpiperidin-1-yl)-3-oxopropyl]-5H-imidazo[2,1-a]isoindole;

5-(4-bromophenyl)-5-[3-(3,5-dimethylpiperidin-1-yl)-3-oxopropyl]-5H-imidazo[2,1-a]isoindole;

3-[5-(4-bromophenyl)-5H-imidazo[2,1-a]isoindol-5-yl]-N-cyclohexyl-N-(1-methylethyl)propanamide;

3-[5-(4-bromophenyl)-5H-imidazo[2,1-a]isoindol-5-yl]-N-cyclohexyl-N-methylpropanamide;

5-(3-azepan-1-yl-3-oxopropyl)-5-(4-bromophenyl)-5H-imidazo[2,1-a]isoindole;

3-[5-(4-bromophenyl)-5H-imidazo[2,1-a]isoindol-5-yl]-N,N-bis(1-methylethyl)propanamide;

3-[5-(4-bromophenyl)-5H-imidazo[2,1-a]isoindol-5-yl]-N,N-bis(2-methylpropyl)propanamide;

5-(4-bromophenyl)-5-[3-(4,4-dimethylpiperidin-1-yl)-3-oxopropyl]-5H-imidazo[2,1-a]isoindole;

5-(4-bromophenyl)-5-[3-(1,4-dioxa-8-azaspiro[4.5]dec-8-yl)-3-oxopropyl]-5H-imidazo[2,1-a]isoindole;

1-{3-[5-(4-bromophenyl)-5H-imidazo[2,1-a]isoindol-5-yl]propanoyl}piperidine-3-carboxamide;

5-[3-(1,4'-bipiperidin-1'-yl)-3-oxopropyl]-5-(4-bromophenyl)-5H-imidazo[2,1-a]isoindole;

5-(4-bromophenyl)-5-[3-oxo-3-(4-pyrrolidin-1-ylpiperidin-1-yl)propyl]-5H-imidazo[2,1-a]isoindole;

5-(4-bromophenyl)-5-{3-oxo-3-[3-(trifluoromethyl)piperidin-1-yl]propyl}-5H-imidazo[2,1-a]isoindole;

5-(4-bromophenyl)-5-[3-(octahydro-2H-pyrido[1,2-a]pyrazin-2-yl)-3-oxopropyl]-5H-imidazo[2,1-a]isoindole;

5-(4-bromophenyl)-5-{3-[4-(1-morpholin-4-ylethyl)piperidin-1-yl]-3-oxopropyl}-5H-imidazo[2,1-a]isoindole;

5-(4-bromophenyl)-5-{3-oxo-3-[2-(trifluoromethyl)piperidin-1-yl]propyl}-5H-imidazo[2,1-a]isoindole;

5-(4-bromophenyl)-5-{3-oxo-3-[4-(1-pyrrolidin-1-ylethyl)piperidin-1-yl]propyl}-5H-imidazo[2,1-a]isoindole;

3-[5-(4-bromophenyl)-5H-imidazo[2,1-a]isoindol-5-yl]-N-ethyl-N-(tetrahydrofuran-2-ylmethyl)propanamide;

5-(4-bromophenyl)-5-[3-oxo-3-(3-phenylpiperidin-1-yl)propyl]-5H-imidazo[2,1-a]isoindole;

5-(4-bromophenyl)-5-{3-oxo-3-[4-(trifluoromethyl)piperidin-1-yl]propyl}-5H-imidazo[2,1-a]isoindole;

(1-{3-[5-(4-bromophenyl)-5H-imidazo[2,1-a]isoindol-5-yl]propanoyl}piperidin-4-yl)(pyridin-3-yl)methanol;

5-(4-bromophenyl)-5-{3-[3-(morpholin-4-ylmethyl)piperidin-1-yl]-3-oxopropyl}-5H-imidazo[2,1-a]isoindole;

5-(4-bromophenyl)-5-{3-[4-(morpholin-4-ylmethyl)piperidin-1-yl]-3-oxopropyl}-5H-imidazo[2,1-a]isoindole;
5-(4-bromophenyl)-5-[3-(3-methoxypiperidin-1-yl)-3-oxopropyl]-5H-imidazo[2,1-a]isoindole;
5-(4-bromophenyl)-5-[3-(1,4-dioxa-7-azaspiro[4.5]dec-7-yl)-3-oxopropyl]-5H-imidazo[2,1-a]isoindole;
5-(4-bromophenyl)-5-[3-(3-fluoropiperidin-1-yl)-3-oxopropyl]-5H-imidazo[2,1-a]isoindole;
6-(1-{3-[5-(4-bromophenyl)-5H-imidazo[2,1-a]isoindol-5-yl]propanoyl}piperidin-4-yl)pyridin-2(1H)-one;
5-(4-bromophenyl)-5-[3-(4-cyclopropylpiperidin-1-yl)-3-oxopropyl]-5H-imidazo[2,1-a]isoindole;
5-(4-bromophenyl)-5-[3-(2,6-dimethylmorpholin-4-yl)-3-oxopropyl]-5H-imidazo[2,1-a]isoindole;
5-(4-bromophenyl)-5-[3-oxo-3-(2-phenylmorpholin-4-yl)propyl]-5H-imidazo[2,1-a]isoindole;
5-(4-bromophenyl)-5-[3-oxo-3-(2-pyridin-3-ylmorpholin-4-yl)propyl]-5H-imidazo[2,1-a]isoindole;
5-(4-bromophenyl)-5-[3-(3,3-difluoropiperidin-1-yl)-3-oxopropyl]-5H-imidazo[2,1-a]isoindole;
5-(4-bromophenyl)-5-{3-[(1S,4S)-2-oxa-5-azabicyclo[2.2.1]hept-5-yl]-3-oxopropyl}-5H-imidazo[2,1-a]isoindole;
5-(4-bromophenyl)-5-(3-morpholin-4-yl-3-oxopropyl)-5H-imidazo[2,1-a]isoindole;
5-(4-bromophenyl)-5-[3-(4,4-difluoropiperidin-1-yl)-3-oxopropyl]-5H-imidazo[2,1-a]isoindole;
5-(4-bromophenyl)-5-[3-(2-methylpyrrolidin-1-yl)-3-oxopropyl]-5H-imidazo[2,1-a]isoindole;
5-(4-bromophenyl)-5-{3-[2-(methoxymethyl)pyrrolidin-1-yl]-3-oxopropyl}-5H-imidazo[2,1-a]isoindole;
5-(4-bromophenyl)-5-{3-oxo-3-[3-(trifluoromethyl)pyrrolidin-1-yl]propyl}-5H-imidazo[2,1-a]isoindole;
5-(4-bromophenyl)-5-[3-(3-methylpyrrolidin-1-yl)-3-oxopropyl]-5H-imidazo[2,1-a]isoindole;
5-(4-bromophenyl)-5-[3-(3,3-difluoropyrrolidin-1-yl)-3-oxopropyl]-5H-imidazo[2,1-a]isoindole;
5-(4-bromophenyl)-5-[3-oxo-3-(2-phenylpyrrolidin-1-yl)propyl]-5H-imidazo[2,1-a]isoindole;
5-(4-bromophenyl)-5-[3-oxo-3-(3-phenylpyrrolidin-1-yl)propyl]-5H-imidazo[2,1-a]isoindole;
5-(4-bromophenyl)-5-[3-(4-fluoropiperidin-1-yl)-3-oxopropyl]-5H-imidazo[2,1-a]isoindole;
5-(4-bromophenyl)-5-[3-(2,5-dimethylpyrrolidin-1-yl)-3-oxopropyl]-5H-imidazo[2,1-a]isoindole;
5-(4-bromophenyl)-5-[3-(4,4-dimethyl-1,3-oxazolidin-3-yl)-3-oxopropyl]-5H-imidazo[2,1-]isoindole;
5-(4-bromophenyl)-5-[3-(2-methylpiperidin-1-yl)-3-oxopropyl]-5H-imidazo[2,1-a]isoindole;
5-(4-bromophenyl)-5-[3-(2,6-dimethylpiperidin-1-yl)-3-oxopropyl]-5H-imidazo[2,1-a]isoindole;
5-[3-(2-azabicyclo[2.2.1]hept-2-yl)-3-oxopropyl]-5-(4-bromophenyl)-5H-imidazo[2,1-a]isoindole;
3-[5-(4-bromophenyl)-5H-imidazo[2,1-a]isoindol-5-yl]-N-tert-butyl-N-methylpropanamide;
3-[5-(4-bromophenyl)-5H-imidazo[2,1-a]isoindol-5-yl]-N-tert-butyl-N-ethylpropanamide;
3-[5-(4-bromophenyl)-5H-imidazo[2,1-a]isoindol-5-yl]-N-tert-butyl-N-(2-methoxyethyl)propanamide;
3-[5-(4-bromophenyl)-5H-imidazo[2,1-a]isoindol-5-yl]-N-(dicyclopropylmethyl)propanamide;
3-[5-(4-bromophenyl)-5H-imidazo[2,1-a]isoindol-5-yl]-N,N-dimethylpropanamide;
3-[5-(4-bromophenyl)-5H-imidazo[2,1-a]isoindol-5-yl]-N,N-dipropylpropanamide;
3-[5-(4-bromophenyl)-5H-imidazo[2,1-a]isoindol-5-yl]-N,N-bis(2-methoxyethyl)propanamide;
3-[5-(4-bromophenyl)-5H-imidazo[2,1-a]isoindol-5-yl]-N,N-bis(1-methylpropyl)propanamide;
3-[5-(4-bromophenyl)-5H-imidazo[2,1-a]isoindol-5-yl]-N-ethyl-N-(1-methylethyl)propanamide;
5-{3-[(1s,4s)-7-azabicyclo[2.2.1]hept-7-yl]-3-oxopropyl}-5-(4-bromophenyl)-5H-imidazo[2,1-a]isoindole;
5-[3-(8-azabicyclo[3.2.1]oct-8-yl)-3-oxopropyl]-5-(4-bromophenyl)-5H-imidazo[2,1-a]isoindole;
3-[5-(4-chlorophenyl)-5H-imidazo[2,1-a]isoindol-5-yl]-N,N-diethylpropanamide;
5-(4-chlorophenyl)-5-[3-(3,3-dimethylpiperidin-1-yl)-3-oxopropyl]-5H-imidazo[2,1-a]isoindole;
5-(4-chlorophenyl)-5-[3-(2-ethylpiperidin-1-yl)-3-oxopropyl]-5H-imidazo[2,1-a]isoindole;
5-(4-chlorophenyl)-5-{3-oxo-3-[4-(thiophen-2-ylcarbonyl)piperazin-1-yl]propyl}-5H-imidazo[2,1-a]isoindole;
5-(4-chlorophenyl)-5-[3-(3-methylpiperidin-1-yl)-3-oxopropyl]-5H-imidazo[2,1-a]isoindole;
5-(4-chlorophenyl)-5-[3-(3,5-dimethylpiperidin-1-yl)-3-oxopropyl]-5H-imidazo[2,1-a]isoindole;
5-(3-azepan-1-yl-3-oxopropyl)-5-(4-chlorophenyl)-5H-imidazo[2,1-a]isoindole;
3-[5-(4-chlorophenyl)-5H-imidazo[2,1-a]isoindol-5-yl]-N,N-bis(1-methylethyl)propanamide;
1-{3-[5-(4-chlorophenyl)-5H-imidazo[2,1-a]isoindol-5-yl]propanoyl}piperidine-3-carboxamide;
5-(4-chlorophenyl)-5-{3-oxo-3-[3-(trifluoromethyl)piperidin-1-yl]propyl}-5H-imidazo[2,1-a]isoindole;
5-(4-chlorophenyl)-5-{3-oxo-3-[2-(trifluoromethyl)piperidin-1-yl]propyl}-5H-imidazo[2,1-a]isoindole;
5-(4-chlorophenyl)-5-{3-oxo-3-[4-(1-pyrrolidin-1-ylethyl)piperidin-1-yl]propyl}-5H-imidazo[2,1-a]isoindole;
5-(4-chlorophenyl)-5-[3-(2-methylpyrrolidin-1-yl)-3-oxopropyl]-5H-imidazo[2,1-a]isoindole;
5-(4-chlorophenyl)-5-{3-[2-(methoxymethyl)pyrrolidin-1-yl]-3-oxopropyl}-5H-imidazo[2,1-a]isoindole;
5-(4-chlorophenyl)-5-(3-oxo-3-piperidin-1-ylpropyl)-5H-imidazo[2,1-a]isoindole;
5-(4-chlorophenyl)-5-[3-(3,4-dihydro-1,5-naphthyridin-1(2H)-yl)-3-oxopropyl]-5H-imidazo[2,1-a]isoindole;
5-(4-chlorophenyl)-5-[3-(2,3-dihydro-1H-pyrrolo[2,3-b]pyridin-1-yl)-3-oxopropyl]-5H-imidazo[2,1-a]isoindole;
5-(4-chlorophenyl)-5-[3-(2,3-dihydro-1H-pyrrolo[2,3-c]pyridin-1-yl)-3-oxopropyl]-5H-imidazo[2,1-a]isoindole;
3-[5-(4-chlorophenyl)-5H-imidazo[2,1-a]isoindol-5-yl]-N-methyl-N-pyridin-4-ylpropanamide;
3-[5-(4-chlorophenyl)-5H-imidazo[2,1-a]isoindol-5-yl]-N-methyl-N-pyridin-2-ylpropanamide;
5-(4-chlorophenyl)-5-[3-(4,4-dimethyl-1,3-oxazolidin-3-yl)-3-oxopropyl]-5H-imidazo[2,1-a]isoindole;
5-(4-chlorophenyl)-5-[3-(2-methylpiperidin-1-yl)-3-oxopropyl]-5H-imidazo[2,1-a]isoindole;
5-(4-chlorophenyl)-5-[3-(2,6-dimethylpiperidin-1-yl)-3-oxopropyl]-5H-imidazo[2,1-a]isoindole;
5-[3-(2-azabicyclo[2.2.1]hept-2-yl)-3-oxopropyl]-5-(4-chlorophenyl)-5H-imidazo[2,1-a]isoindole;
N-tert-butyl-3-[5-(4-chlorophenyl)-5H-imidazo[2,1-a]isoindol-5-yl]-N-methylpropanamide;
N-tert-butyl-3-[5-(4-chlorophenyl)-5H-imidazo[2,1-a]isoindol-5-yl]-N-ethylpropanamide;

N-tert-butyl-3-[5-(4-chlorophenyl)-5H-imidazo[2,1-a] isoindol-5-yl]-N-(2-methoxyethyl)-propanamide;
3-[5-(4-chlorophenyl)-5H-imidazo[2,1-a]isoindol-5-yl]-N,N-dimethylpropanamide;
3-[5-(4-chlorophenyl)-5H-imidazo[2,1-a]isoindol-5-yl]-N,N-dipropylpropanamide;
3-[5-(4-chlorophenyl)-5H-imidazo[2,1-a]isoindol-5-yl]-N,N-bis(2-methoxyethyl)propanamide;
3-[5-(4-chlorophenyl)-5H-imidazo[2,1-a]isoindol-5-yl]-N,N-bis(1-methylpropyl)propanamide;
3-[5-(4-chlorophenyl)-5H-imidazo[2,1-a]isoindol-5-yl]-N-ethyl-N-(1-methylethyl)propanamide;
5-(3-azetidin-1-yl-3-oxopropyl)-5-(4-chlorophenyl)-5H-imidazo[2,1-a]isoindole;
5-{3-[(1s,4s)-7-azabicyclo[2.2.1]hept-7-yl]-3-oxopropyl}-5-(4-chlorophenyl)-5H-imidazo[2,1-a]isoindole;
5-[3-(8-azabicyclo[3.2.1]oct-8-yl)-3-oxopropyl]-5-(4-chlorophenyl)-5H-imidazo[2,1-a]isoindole;
5-(4-chlorophenyl)-5-[3-(2,5-dimethylpyrrolidin-1-yl)-3-oxopropyl]-5H-imidazo[2,1-a]isoindole;
5-(4-chlorophenyl)-5-[3-(2,5-dimethylpyrrolidin-1-yl)-3-oxopropyl]-7-methoxy-5H-imidazo[2,1-a]isoindole;
5-[3-(2,5-dimethylpyrrolidin-1-yl)-3-oxopropyl]-5-(4-fluorophenyl)-5H-imidazo[2,1-a]isoindole;
N,N-diethyl-3-[5-(4-fluorophenyl)-5H-imidazo[2,1-a] isoindol-5-yl]propanamide;
5-[3-(3,3-dimethylpiperidin-1-yl)-3-oxopropyl]-5-(4-fluorophenyl)-5H-imidazo[2,1-a]isoindole;
5-[3-(2-ethylpiperidin-1-yl)-3-oxopropyl]-5-(4-fluorophenyl)-5H-imidazo[2,1-a]isoindole;
5-(4-fluorophenyl)-5-{3-oxo-3-[4-(thiophen-2-ylcarbonyl)piperazin-1-yl]propyl}-5H-imidazo[2,1-a]isoindole;
5-(4-fluorophenyl)-5-[3-(3-methylpiperidin-1-yl)-3-oxopropyl]-5H-imidazo[2,1-a]isoindole;
5-[3-(3,5-dimethylpiperidin-1-yl)-3-oxopropyl]-5-(4-fluorophenyl)-5H-imidazo[2,1-a]isoindole;
5-(3-azepan-1-yl-3-oxopropyl)-5-(4-fluorophenyl)-5H-imidazo[2,1-a]isoindole;
3-[5-(4-fluorophenyl)-5H-imidazo[2,1-a]isoindol-5-yl]-N,N-bis(1-methylethyl)propanamide;
1-{3-[5-(4-fluorophenyl)-5H-imidazo[2,1-a]isoindol-5-yl]propanoyl}piperidine-3-carboxamide;
5-(4-fluorophenyl)-5-{3-oxo-3-[3-(trifluoromethyl)piperidin-1-yl]propyl}-5H-imidazo[2,1-a]isoindole;
5-(4-fluorophenyl)-5-{3-oxo-3-[2-(trifluoromethyl)piperidin-1-yl]propyl}-5H-imidazo[2,1-a]isoindole;
5-(4-fluorophenyl)-5-{3-oxo-3-[4-(1-pyrrolidin-1-ylethyl)piperidin-1-yl]propyl}-5H-imidazo[2,1-a]isoindole;
5-(4-fluorophenyl)-5-[3-(2-methylpyrrolidin-1-yl)-3-oxopropyl]-5H-imidazo[2,1-a]isoindole;
5-(4-fluorophenyl)-5-{3-[2-(methoxymethyl)pyrrolidin-1-yl]-3-oxopropyl}-5H-imidazo[2,1-a]isoindole;
5-(4-fluorophenyl)-5-(3-oxo-3-piperidin-1-ylpropyl)-5H-imidazo[2,1-a]isoindole;
5-(4-fluorophenyl)-5-[3-(2-methylpiperidin-1-yl)-3-oxopropyl]-5H-imidazo[2,1-a]isoindole;
5-[3-(2,6-dimethylpiperidin-1-yl)-3-oxopropyl]-5-(4-fluorophenyl)-5H-imidazo[2,1-a]isoindole;
5-[3-(2-azabicyclo[2.2.1]hept-2-yl)-3-oxopropyl]-5-(4-fluorophenyl)-5H-imidazo[2,1-a]isoindole;
N-tert-butyl-3-[5-(4-fluorophenyl)-5H-imidazo[2,1-a] isoindol-5-yl]-N-methylpropanamide;
N-tert-butyl-N-ethyl-3-[5-(4-fluorophenyl)-5H-imidazo [2,1-a]isoindol-5-yl]propanamide;
N-tert-butyl-3-[5-(4-fluorophenyl)-5H-imidazo[2,1-a] isoindol-5-yl]-N-(2-methoxyethyl)propanamide;
3-[5-(4-fluorophenyl)-5H-imidazo[2,1-a]isoindol-5-yl]-N,N-dipropylpropanamide;
3-[5-(4-fluorophenyl)-5H-imidazo[2,1-a]isoindol-5-yl]-N,N-bis(1-methylpropyl)propanamide;
N-ethyl-3-[5-(4-fluorophenyl)-5H-imidazo[2,1-a]isoindol-5-yl]-N-(1-methylethyl)propanamide;
5-{3-[(1s,4s)-7-azabicyclo[2.2.1]hept-7-yl]-3-oxopropyl}-5-(4-fluorophenyl)-5H-imidazo[2,1-a]isoindole;
5-[3-(8-azabicyclo[3.2.1]oct-8-yl)-3-oxopropyl]-5-(4-fluorophenyl)-5H-imidazo[2,1-a]isoindole;
4-{5-[3-(2,5-dimethylpyrrolidin-1-yl)-3-oxopropyl]-5H-imidazo[2,1-a]isoindol-5-yl}benzonitrile;
5-(4-bromophenyl)-5-{3-oxo-3-[4-(pyrrolidin-1-ylmethyl)piperidin-1-yl]propyl}-5H-imidazo[2,1-a]isoindole;
5-(4-chlorophenyl)-7-methoxy-5-{3-oxo-3-[4-(1-pyrrolidin-1-ylethyl)piperidin-1-yl]propyl}-5H-imidazo[2,1-a]isoindole;
5-(4-bromophenyl)-5-[4-(2,5-dimethylpyrrolidin-1-yl)-4-oxobutyl]-5H-imidazo[2,1-a]isoindole;
4-[5-(4-bromophenyl)-5H-imidazo[2,1-a]isoindol-5-yl]-N,N-bis(1-methylethyl)butanamide;
4-[5-(4-bromophenyl)-5H-imidazo[2,1-a]isoindol-5-yl]-N-ethyl-N-methylbutanamide;
5-(4-bromophenyl)-5-(4-oxo-4-piperidin-1-ylbutyl)-5H-imidazo[2,1-a]isoindole;
5-(4-bromophenyl)-5-{4-oxo-4-[4-(1-pyrrolidin-1-ylethyl)piperidin-1-yl]butyl}-5H-imidazo[2,1-a]isoindole;
(1-{3-[5-(4-bromophenyl)-5H-imidazo[2,1-a]isoindol-5-yl]propanoyl}piperidin-4-yl)methanol;
5-(4-bromophenyl)-5-{3-[(2R,5R)-2,5-dimethylpyrrolidin-1-yl]-3-oxopropyl}-5H-imidazo[2,1-a]isoindole;
3-[5-(4-bromophenyl)-5H-imidazo[2,1-a]isoindol-5-yl]-N-methyl-N-(1-methylcyclopentyl)-propanamide;
5-(4-bromophenyl)-5-[3-oxo-3-(2-propylpyrrolidin-1-yl) propyl]-5H-imidazo[2,1-a]isoindole;
3-[5-(4-bromophenyl)-5H-imidazo[2,1-a]isoindol-5-yl]-N-methyl-N-(1-methylpiperidin-4-yl)propanamide;
N-benzyl-3-[5-(4-bromophenyl)-5H-imidazo[2,1-a]isoindol-5-yl]-N-ethylpropanamide;
3-[5-(4-bromophenyl)-5H-imidazo[2,1-a]isoindol-5-yl]-N-(2,4-dimethylcyclopentyl)-N-methylpropanamide;
(1-{3-[5-(4-bromophenyl)-5H-imidazo[2,1-a]isoindol-5-yl]propanoyl}piperidin-4-yl)(pyridin-2-yl)methanol;
1'-{3-[5-(4-bromophenyl)-5H-imidazo[2,1-a]isoindol-5-yl]propanoyl}-3H-spiro[2-benzofuran-1,4'-piperidin]-3-one;
5-(4-bromophenyl)-5-{3-[4-(5-methyl-1,3,4-oxadiazol-2-yl)piperidin-1-yl]-3-oxopropyl}-5H-imidazo[2,1-a]isoindole;
5-(4-bromophenyl)-5-(3-{3-[(2-methyl-1H-imidazol-1-yl)methyl]piperidin-1-yl}-3-oxopropyl)-5H-imidazo [2,1-a]isoindole;
5-(4-bromophenyl)-5-{3-[4-(3-methyl-1H-pyrazol-5-yl) piperidin-1-yl]-3-oxopropyl}-5H-imidazo[2,1-a]isoindole;
5-(4-bromophenyl)-5-{3-oxo-3-[4-(1H-pyrazol-1-ylmethyl)piperidin-1-yl]propyl}-5H-imidazo[2,1-a]isoindole;
5-(4-bromophenyl)-5-{3-[4-(cyclopentylmethyl)piperazin-1-yl]-3-oxopropyl}-5H-imidazo[2,1-a]isoindole;
2-(4-{3-[5-(4-bromophenyl)-5H-imidazo[2,1-a]isoindol-5-yl]propanoyl}piperazin-1-yl)cyclohexanol;

5-{3-[4-(1-azabicyclo[2.2.2]oct-3-yl)piperazin-1-yl]-3-oxopropyl}-5-(4-bromophenyl)-5H-imidazo[2,1-a]isoindole;

5-(4-bromophenyl)-5-{3-oxo-3-[4-(2-pyrrolidin-1-yl-ethyl)piperazin-1-yl]propyl}-5H-imidazo[2,1-a]isoindole;

5-(4-bromophenyl)-5-(3-{4-[(2-methyl-1,3-thiazol-4-yl)methyl]piperazin-1-yl}-3-oxopropyl)-5H-imidazo[2,1-a]isoindole;

5-[3-(4-benzylpiperazin-1-yl)-3-oxopropyl]-5-(4-bromophenyl)-5H-imidazo[2,1-a]isoindole;

3-[5-(4-bromophenyl)-5H-imidazo[2,1-a]isoindol-5-yl]-N-ethyl-N-(2-methoxyethyl)propanamide;

3-[5-(4-chlorophenyl)-7-methoxy-5H-imidazo[2,1-a]isoindol-5-yl]-N,N-diethylpropanamide; and 3-[5-(4-chlorophenyl)-7-methoxy-5H-imidazo[2,1-a]isoindol-5-yl]-N,N-dipropylpropanamide;

or a pharmaceutically acceptable salt thereof.

4. A pharmaceutical composition which comprises an inert carrier and a compound of claim 1 or a pharmaceutically acceptable salt thereof.

\* \* \* \* \*